(12) United States Patent
Shokat

(10) Patent No.: US 6,521,417 B1
(45) Date of Patent: Feb. 18, 2003

(54) ENGINEERED PROTEIN KINASES WHICH CAN UTILIZE MODIFIED NUCLEOTIDE TRIPHOSPHATE SUBSTRATES

(75) Inventor: Kevan M. Shokat, San Francisco, CA (US)

(73) Assignee: Princeton University, Princeton, NJ (US)

(*) Notice: Subject to any disclaimer, the term of this patent is extended or adjusted under 35 U.S.C. 154(b) by 0 days.

(21) Appl. No.: 09/568,466

(22) Filed: May 10, 2000

Related U.S. Application Data

(60) Division of application No. 09/367,065, filed as application No. PCT/US98/02522 on Feb. 9, 1998, now Pat. No. 6,390,821, which is a continuation-in-part of application No. 08/797,522, filed on Feb. 7, 1997, now abandoned.
(60) Provisional application No. 60/046,727, filed on May 16, 1997, now abandoned.

(51) Int. Cl.[7] ................................................. C12Q 1/48
(52) U.S. Cl. ........................................ 435/15; 435/194
(58) Field of Search .................................. 435/15, 194

(56) References Cited

U.S. PATENT DOCUMENTS

| | | | |
|---|---|---|---|
| 5,352,660 A | 10/1994 | Pawson | 514/12 |
| 5,443,962 A | 8/1995 | Draetta et al. | 435/29 |
| 5,593,997 A | 1/1997 | Dow et al. | 514/258 |
| 5,731,343 A | 3/1998 | Feng et al. | 514/450 |
| 5,800,992 A | 9/1998 | Fodor et al. | 435/6 |
| 5,965,352 A | 10/1999 | Stoughton et al. | 435/4 |
| 6,019,966 A | 2/2000 | Coleman et al. | 424/94.5 |
| 6,100,254 A | 8/2000 | Budde et al. | 514/221 |
| 6,162,613 A | 12/2000 | Su et al. | 435/15 |
| 6,251,911 B1 | 6/2001 | Bold et al. | 514/258 |
| 6,383,790 B1 | 5/2002 | Shokat | 435/194 |
| 6,390,821 B1 | 5/2002 | Shokat | 434/194 |

FOREIGN PATENT DOCUMENTS

| | | |
|---|---|---|
| WO | WO 99/42592 | 8/1999 |
| WO | WO 01/07659 A2 | 2/2001 |

OTHER PUBLICATIONS

Belshaw et al., Rational Design of Orthogonal Receptor–Ligand Combinations, Angw. Chem. Int. Ed. Engl. 34:2129–2132 (1995).
Bishop et al., Design of Allele–specific Inhibitors to Probe Protein Kinase Signaling, Current Biology 8:257–266 (1998).
Bolen et al., The Src Family of Tyrosine Protein Kinases in Hemopoietic Signal Transduction, FASEB J. 6:3403–3409 (1992).
Brown et al., Regulation, Substrates and Functions of Src, Biochem. Biophys. Acta, 12387:121–149 (1996).
Brugge et al., Identification of a Transformation–Specific Antigen Induced by an Avian Sarcoma Virus, Nature, 269:346–348 (1977).
Cohen et al., Modular Binding Domains in Signal Transduction Proteins, Cell 80:237–248 (1995).
Faltynek et al., Damnacanthal is a Highly Potent, Selective Inhibitor of $p56^{lck}$ Tyrosine Kinase Activity, Biochemistry, 34:12404–12410 (1995).
Hanke et al., Discovery of a Novel, Potent and Src Family–Selective Tyrosine Kinase Inhibitor, J. Biol. Chem. 271:695–701 (1996).
Hunter et al., A Thousand and One Protein Kinases, Cell 50:823–829 (1987).
Hunter et al., Protein Kinases and Phosphatases: The Yin and Yang of Protein Phosphorylation and Signaling, Cell, 80:225–236 (1995).
Hwang et al., A Mutation that Alters the Nucleotide Specificity of Elongation Factor Tu, a GTP Regulatory Protein, J. Biol. Chem. 262:13081–13085 (1987).
Liu et al., Engineering Src Family Protein Kinases with Unnatural Nucleotide Specificity, Chemistry & Biology, 5:91–101 (1998).
Mayer et al., Point Mutations in the abl SH2 Domain Coordinately Impair Phosphotyrosine Binding in vitro, Mol. Cell. Biol. 12:609–618 (1992).
Mayer et al., Mutagenic Analysis of the Roles of SH2 and SH3 Domains in Regulation of the Abl Tyrosine Kinase, Mol. Cell. Biol. 14:2883–2894 (1994).
Shah et al., Engineering Unnatural Nucleotide Specificity for Rous Sarcoma Virus Tyrosine Kinase to Uniquely Label its Direct Substrates, Proc. Natl. Acad. Sci. USA 94:3565–3570 (1997).
Taylor et al., The Cell Cycle and c–Src, Curr. Opin. Genet. Dev. 3:26–34 (1993).

(List continued on next page.)

*Primary Examiner*—Nashaat T. Nashed
(74) *Attorney, Agent, or Firm*—Morgan, Lewis & Bockius LLP

(57) ABSTRACT

Engineered protein kinases which can utilize modified nucleotide triphosphate substrates that are not as readily utilized by the wild-type forms of those enzymes, and methods of making and using them are disclosed. Modified nucleotide triphosphate substrates and methods of making and using them are disclosed. Methods are disclosed for using such engineered kinases and such modified substrates to identify which protein substrates the kinases act upon, to measure the extent of such action, and to determine if test compounds can modulate such action. Engineered forms of multi-substrate enzymes which covalently attach part or all of at least one (donor) substrate to at least one other (recipient) substrate, which engineered forms will accept modified substrates that are not as readily utilized by the wild-type forms of those enzymes are disclosed. Methods for making and using such engineered enzymes are disclosed. Modified substrates and methods of making and using them are disclosed. Methods are disclosed for using such engineered enzymes and such modified substrates to identify the recipient substrates the enzymes act upon, to measure the extent of such action, and to measure whether test compounds modulate such action.

8 Claims, 24 Drawing Sheets

OTHER PUBLICATIONS

Waksman et al., Crystal Structure of the Phosphotyrosine Recognition Domain SH2 of v–src Complexed with Tyrosine–Phosphorylated Peptides, Nature 358:646–653 (1992).

Waksman et al., Binding of a High Affinity Phosphotyrosyl Peptic to the Src SH2 Domain: Crystal Structures of the Complexed and Peptide–free Forms, Cell 72:779–790 (1993).

Weijland et al., Toward a Model for the Interaction Between Elongation Factor Tu and the Ribosome, Science 259:1311–1314 (1993).

Yu et al., Solution Structure of the SH3 Domain of Src and Identification of its Ligand–Binding Site, Science 258:1665–1668 (1992).

Xu et al., Substrate Specificities of the Insulin and Insulin–like Growth Factor 1 Receptor Tyrosine Kinase Catalytic Domains, J. Biol. Chem. 270:29825–29830 (1995).

Bishop et al. (Jan. 1999) Generation of monospecific nanomolar tyrosine kinase inhibitors via a chemical genetic approach, J. Am. Chem. Soc. 121:627–631 (American Chemical Society, Easton, PA, USA).

Bishop et al. (May–Jun. 1999) Acquisition of inhibitor–sensitive protein kinases through protein design, Pharmacol. Ther. 82:337–346 (Oxford, Elmsford, NY, USA: Pergamon Press).

Bishop et al. (Sep. 2000) A chemical switch for inhibitor–sensitive alleles of any protein kinase, Nature 407:395–401 (London, United Kingdom: Nature Publishing Group).

Cicchetti et al. (1992) Identification of a protein that binds to the SH3 region of Abl and is similar to Bcr and GAP–rho, Science 257:803–806 (Washington, DC, USA: American Association for the Advancement of Science).

Eck et al. (1993) Recognition of a high–affinity phosphotyrosyl peptide by the Src homology–2 domain of p56$^{lck}$, Nature 362:87–91 (London, United Kingdom: Nature Publishing Group).

Eiseman et al. (1992) Engagement of the high–affinity IgE receptor activates src protein–related tyrosine kinases, Nature 355;78–80 (London, United Kingdom: Nature Publishing Group).

Erpel et al. (1995) Src family protein tyrosine kinases and cellular signal transduction pathways, Curr. Opin. Cell Biol. 7:176–182 (Philadelphia, PA, USA: Current Science).

Hanks et al. (1991) Protein kinase catalytic domain sequence database: Identification of conserved features of primary structure and classification of family members, Methods in Enzymology, 200:38–81 (New York, NY, USA: Academic Press).

Jove et al. (1987) Cell transformation by the viral src oncogene, Ann. Rev. Cell. Biol. 3:31–56 (Palo Alto, CA, USA: Annual Reviews, Inc.).

Kamps et al. (1988) Most of the substrates of oncogenic viral tyrosine protein kinases can be phosphorylated by cellular tyrosine kinases in normal cells, Oncogene Res. 3:105–115 (New York, NY, USA: Harwood Academic Publishers).

Kipreos et al. (1992) Cell cycle–regulated binding of c–abl tyrosine kinase to DNA, Science 256:382–385 (Washington, DC, USA: American Association for the Advancement of Science).

Koyama et al. (1993) Structure of the P13K SH3 domain and analysis of the SH3 Family, Cell 72:945–952 (Cambridge, MA, USA: Cell Press).

Lander et al. (Feb. 2001) Initial sequencing and analysis of the human genome, Nature 409:860–941 (London, United Kingdom: Nature Publishing Group).

Liu et al. (Aug. 1999) Structural basis for selective inhibition of Src family kinases by $PP_1$, Chem. & Biol. 6: 671–678 (Oxford, United Kingdom: Elsevier Science, Ltd.).

Liu et al. (Aug. 1998) A molecular gate which controls unnatural ATP analogue recognition by the tyrosine kinase v–Src, Bioorg. Med. Chem. 6:1219–1226 (Oxford, NY, USA: Pergamon Press).

Michael et al. (1995) Site–directed mutagenesis of Herpes Simplex Virus type 1 thymidine kinase opposes the importance of amino acid positions 251, 321 and 348 for selective recognition of substrate analogs, Biochem. Biophys. Res. Commun. 209:966–973 (Orlando, FL, USA: Elsevier Sciences).

Mustelin, T. (1994) T Cell antigen receptor signaling: three families of tyrosine kinases and a phosphatase, Immunity 1:351–356 (Cambridge, MA, USA: Cell Press).

Pawson, T. (1995) Protein modules and signalling networks, Nature 373:573–580 (London, United Kingdom: Nature Publishing Group).

Renshaw et al. (1992) Oncogenic v–Abl tyrosine kinase can inhibit or stimulate growth, depending on the cell context, EMBO J. 11:3941–3951 (Oxford, United Kingdom: European Molecular Biology Organization by IRL Press).

Sawyers et al. (1994) The nuclear tyrosine kinase c–Abl negatively regulates cell growth, Cell 77:121–131 (Cambridge, MA, USA: Cell Press).

Songyang et al. (1995) Catalytic specificity of protein–tyrosine kinases is critical for selective signalling, Nature 373:536–539 (London, United Kingdom: Nature Publishing Group).

Ullrich et al. (1990) Signal transduction by receptors with tyrosine kinase activity, Cell 61:203–212 (Cambridge, MA, USA: Cell Press).

Velazquez et al. (1992) A protein tyrosine kinase in the interferon alpha/beta signaling pathway, Cell 70:313–320 (Cambridge, MA, USA: Cell Press).

Venter et al. (Feb. 2001) The sequence of the human genome, Science 291:1304–1351 (Washington, DC, USA: American Association for the Advancement of Science).

International Preliminary Examination Report from PCT/US00/19912 (mailed Jan. 22, 2002).

International Search Report from PCT/US00/19912 (mailed Jan. 25, 2001).

Fig. 5A
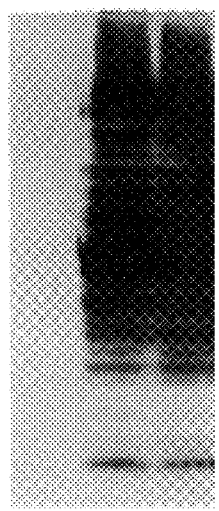
1 2 3
Fig. 5B
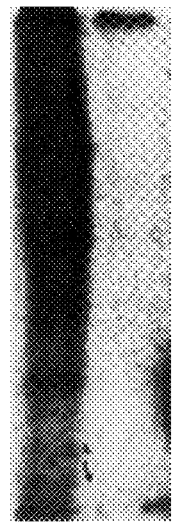
1 2
Fig. 5C
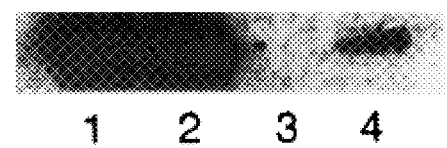
← autophosphorylated kinase
1 2 3 4
Figure 5

Fig. 7A
[γ-³²P] ATP
I338A   I338S
Fig. 7C
[γ-³²P] N⁶-cyclopentyl ATP
I338A   I338S
Fig. 7B
[γ-³²P] ATP
I338A   I338G
Fig. 7D
[γ-³²P] N⁶-cyclopentyl ATP
I338A   I338G
Figure 7

Fig. 10A
Damnacanthal
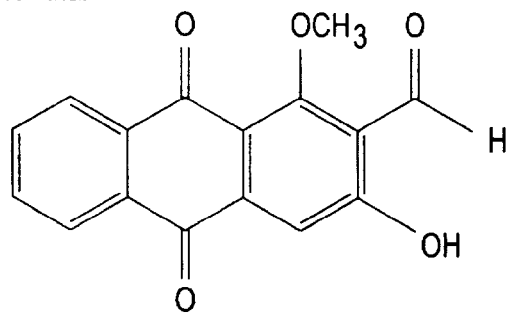
|      | IC$_{50}$ ($\mu$M) |
|------|------|
| lck  | 0.10 |
| fyn  | 2.09 |
| src  | 0.68 |
| erbB2 | 3.5 |
Fig. 10B
PP1
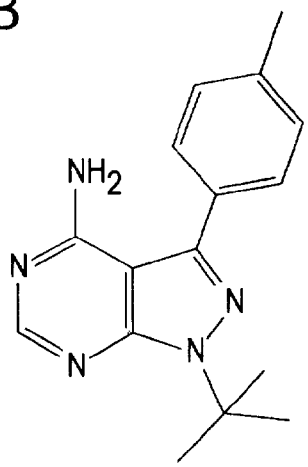
|       | IC$_{50}$ ($\mu$M) |
|-------|-------|
| lck   | 0.005 |
| fyn   | 0.006 |
| src   | 0.17  |
| hck   | 0.020 |
| zap-70 | >100 |
| JAK2  | >50   |
| EGFR  | 0.25  |
Fig. 10C
CGP 57148
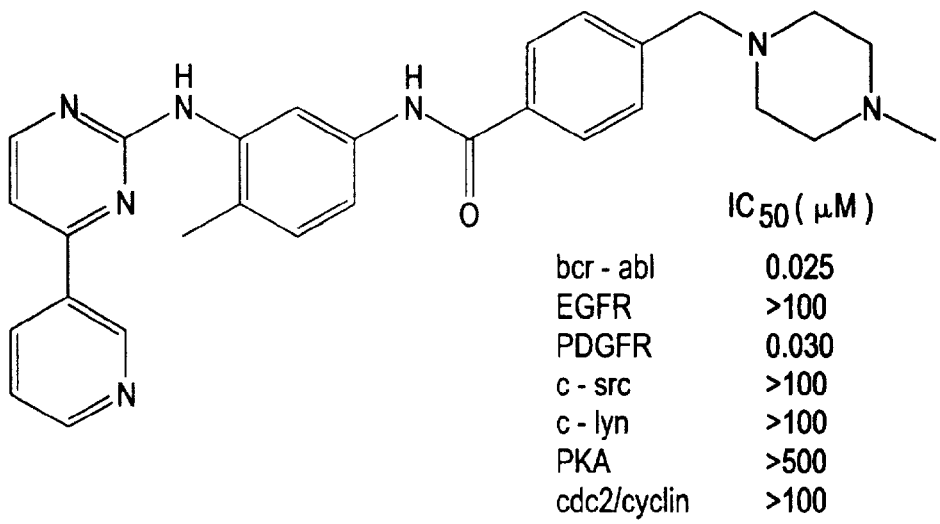
|       | IC$_{50}$ ($\mu$M) |
|-------|-------|
| bcr-abl | 0.025 |
| EGFR    | >100  |
| PDGFR   | 0.030 |
| c-src   | >100  |
| c-lyn   | >100  |
| PKA     | >500  |
| cdc2/cyclin | >100 |
Figure 10

Fig. 11A
N-4 Acyl Analogues
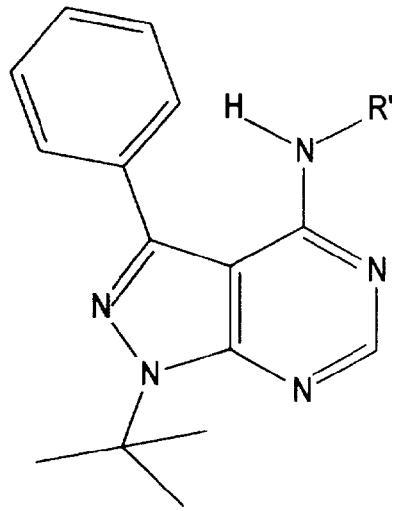
Fig. 11B
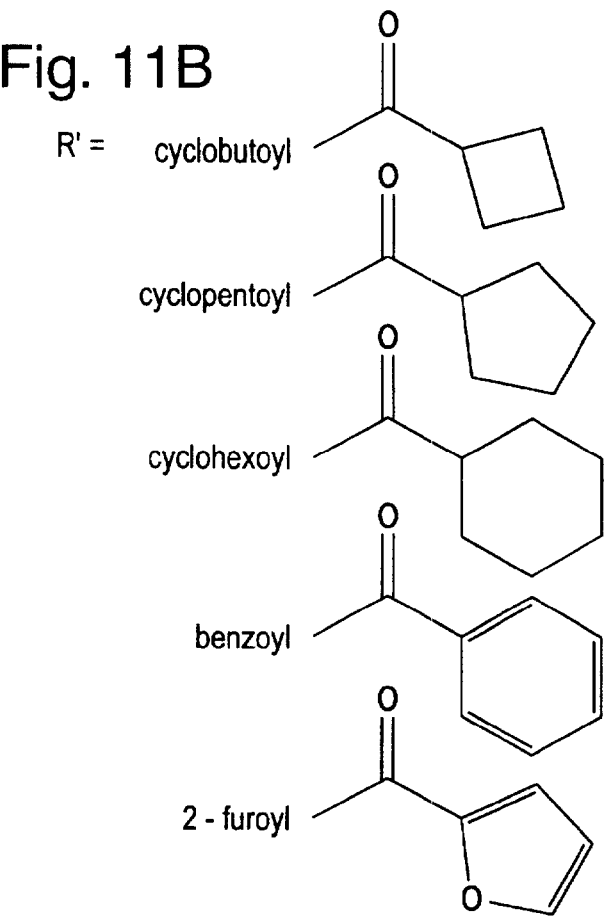
R' = cyclobutoyl
cyclopentoyl
cyclohexoyl
benzoyl
2 - furoyl
Fig. 11C
In vitro Inhibition Data
| | IC$_{50}$ ($\mu$M) | | |
|---|---|---|---|
| R' = | WT fyn | WT src | I338G src |
| H | 0.08 | 35 | <1 |
| cyclobutoyl | | >>400 | 12 |
| cyclopentoyl | 400 | >>400 | 5 |
| cyclohexoyl | 50 | >>400 | 20 |
| benzoyl | >400 | >>400 | 50 |
| 2 - furoyl | | >>400 | 150 |
Figure 11

Fig. 12A
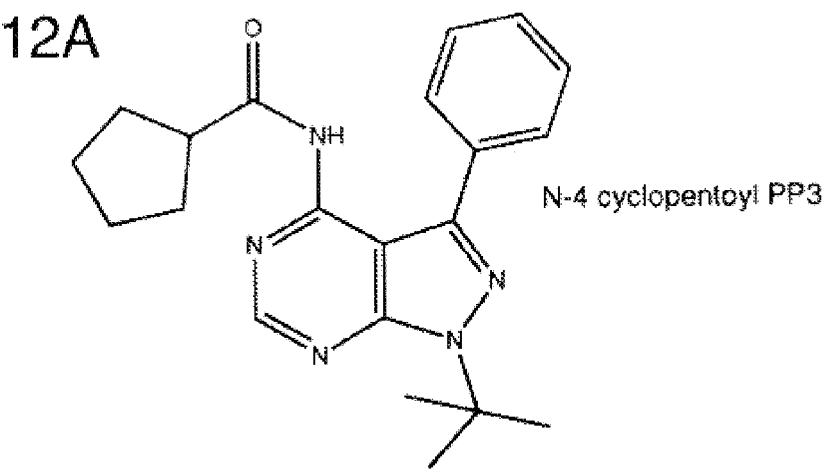
Fig. 12B
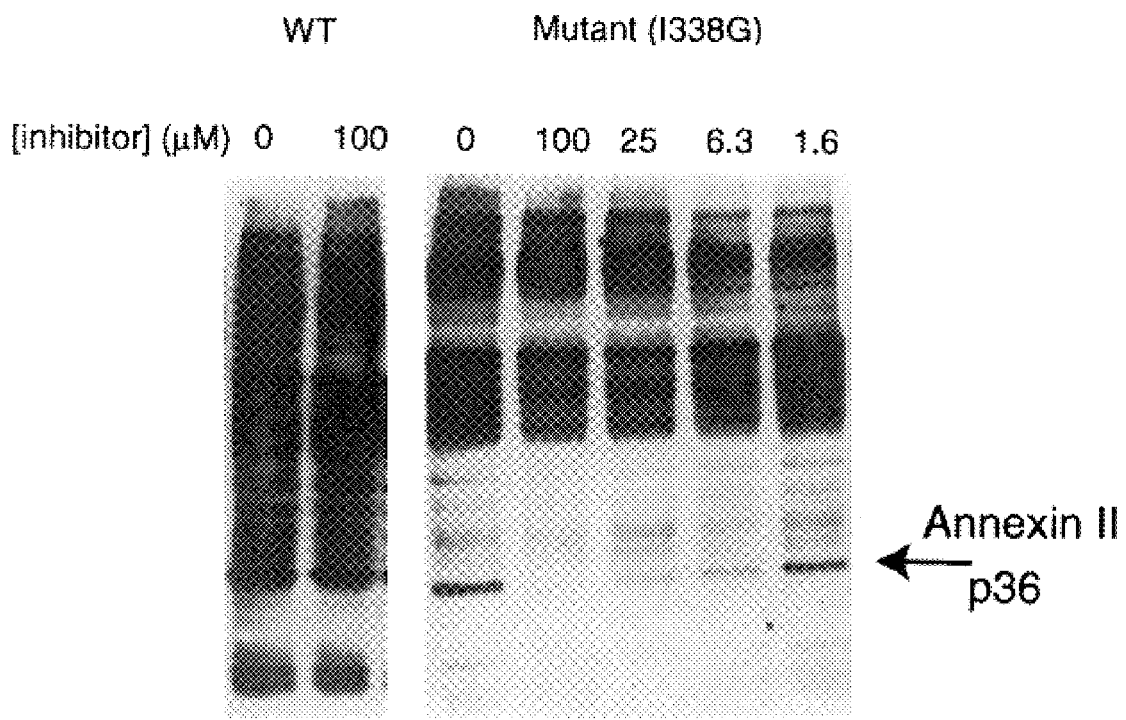
Figure 12

IC$_{50}$ (µM)

| Molecule | WT XD4 | 1338G XD4 | WT Fyn | T339G Fyn | WT Abl | T120A Abl |
|---|---|---|---|---|---|---|
|  | 35 | 0.13 | 0.05 | | | <<10 |
|  | | 200 | >300 | | | |
|  | | 300 | >300 | | | |
|  | | >300 | >300 | | | |
|  | >300 | 75 | >300 | 100 | | >10 |
|  | >300 | 250 | >300 | 26 | | >10 |
|  | >300 | 85 | >300 | 63 | | >10 |
|  | | | | | | |
|  | | | | | | |

| | | | | | | |
|---|---|---|---|---|---|---|
|  | | | | | | |
|  | | | | | | |
|  | >300 | 12 | 6.5 | 5 | | |
|  | >300 | 19 | 80 | 9 | | |
|  | >300 | 20 | 50 | 5 | | |
|  | >300 | 150 | 15 | 19 | | |
|  | >300 | 10 | 300 | 11 | | (10 |
|  | >300 | 10 | 300 | 6 | | (10 |
|  | | 1.2 | | | | <10 |
|  | | 0.63 | | | | |

| | | | | | | |
|---|---|---|---|---|---|---|
|  | | (0.411 | | | | 1.8 |
|  | >300 | 0.43 | 300 | 0.83 | 300 | (10 |
|  | | | | | | |
|  | | | | | | |
|  | | | | | | >10 |
|  | 100 | (0.05 | 0.1 | | | |
|  | | >100 | >300 | | | |
|  | | | 2 | | | |
|  | | | 7 | | | |
|  | | | | | | |

| | | | | | | |
|---|---|---|---|---|---|---|
|  | >1000 | 0.510 | 0.4 | | <<6.5 | |
|  | >300 | >10 | >300 | | | |
|  | >300 | >10 | >300 | | | |
|  | >300 | >10 | >300 | | | |
|  | >300 | >10 | >300 | | | |
|  | >300 | >10 | >300 | | | |
|  | >300 | >10 | >300 | | | |
|  | >300 | >10 | >300 | | | |
|  | >300 | >10 | >300 | | | |
|  | >300 | >10 | >300 | | | |

| | | | | | | |
|---|---|---|---|---|---|---|
|  | >300 | >10 | >300 | | | |
|  | | | | | | |
|  | <10 | 2.5 | <<10 | | | |
|  | >300 | >10 | >300 | | | |
|  | >300 | >10 | >300 | | | |
|  | >300 | >10 | >300 | | | |
|  | >300 | >10 | >300 | | | |
|  | >300 | >10 | >300 | | | |
|  | >300 | >10 | >300 | | | |

Fig. 15A
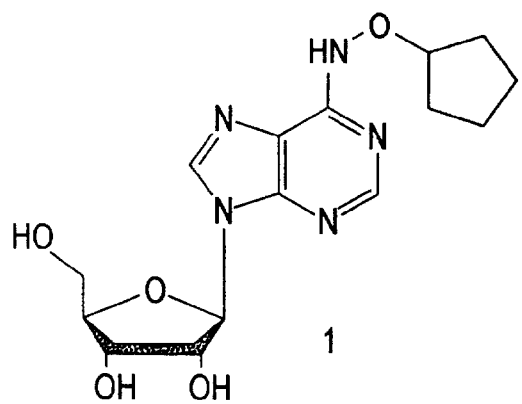
Fig. 15B
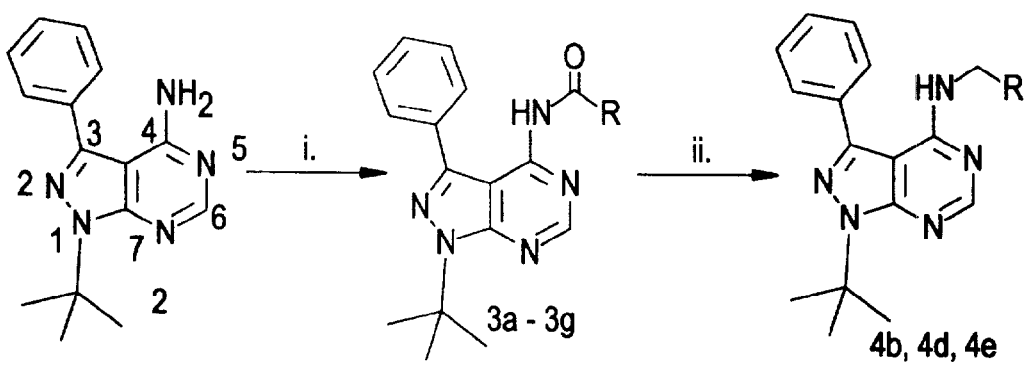
| Cmpd | R= | Cmpd | R= |
|------|-----|------|-----|
| 3a | cyclobutyl | 4b | cyclopentyl |
| 3b | cyclopentyl | 4d | 2 - furyl |
| 3c | cyclohexyl | 4e | phenyl |
| 3d | 2 - furyl | | |
| 3e | phenyl | | |
| 3f | p - methylphenyl | | |
| 3g | p-tert-butylphenyl | | |
Figure 15

Fig. 16A
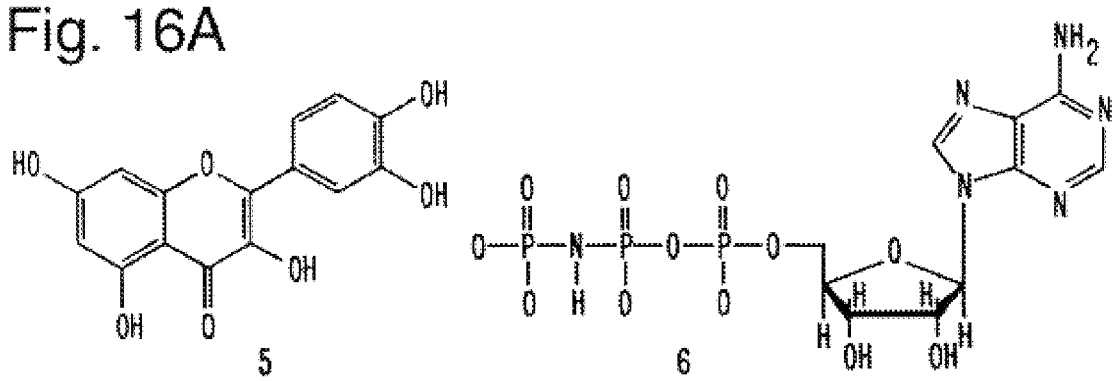
Fig. 16B
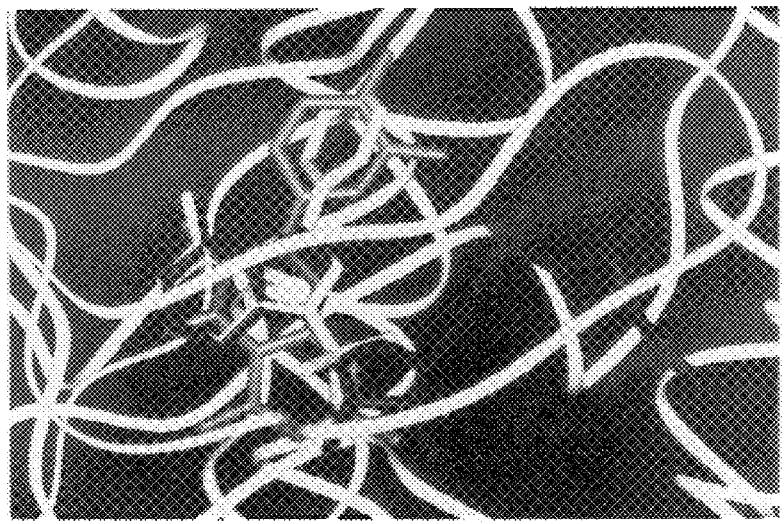
Fig. 16C
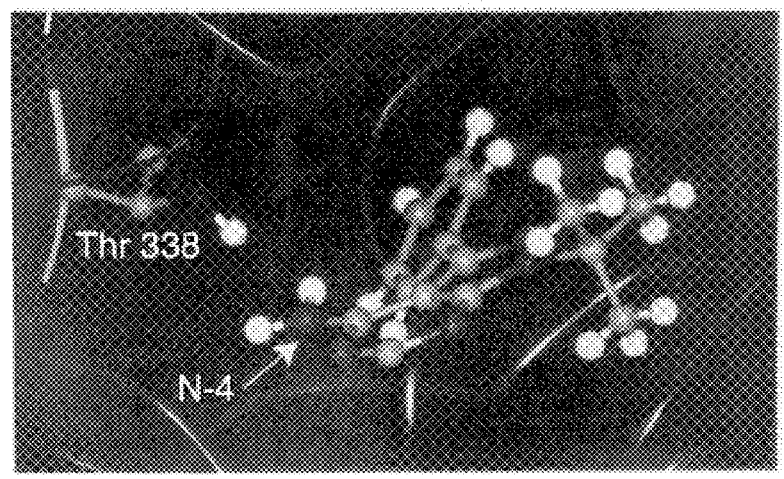
Figure 16

SEQUENCE LISTING

```
<160> NUMBER OF SEQ ID NOS: 20

<210> SEQ ID NO 1
<211> LENGTH: 27
<212> TYPE: PRT
<213> ORGANISM: Homo sapiens
<220> FEATURE:
<223> OTHER INFORMATION: ATP binding domain of PKA, residues 99-125

<400> SEQUENCE: 1

Asn Phe Pro Phe Leu Val Lys Leu Glu Phe Ser Phe Lys Asp Asn Ser
 1               5                  10                  15

Asn Leu Tyr Met Val Met Glu Tyr Val Pro Gly
            20                  25

<210> SEQ ID NO 2
<211> LENGTH: 27
<212> TYPE: PRT
<213> ORGANISM: Rous sarcoma virus
<220> FEATURE:
<223> OTHER INFORMATION: ATP binding domain of CDK2, residues 59-85

<400> SEQUENCE: 2

Asn His Pro Asn Ile Val Lys Leu Leu Asp Val Ile His Thr Glu Asn
 1               5                  10                  15

Lys Leu Tyr Leu Val Phe Glu Phe Leu His Gln
            20                  25

<210> SEQ ID NO 3
<211> LENGTH: 26
<212> TYPE: PRT
<213> ORGANISM: Rous sarcoma virus
```

-continued

```
<220> FEATURE:
<223> OTHER INFORMATION: ATP binding domain of v-Src, residues 318-343

<400> SEQUENCE: 3

Arg His Glu Lys Leu Val Gln Leu Tyr Ala Val Val Ser Glu Glu Pro
 1               5                  10                  15

Ile Tyr Ile Val Ile Glu Tyr Met Ser Lys
            20                  25

<210> SEQ ID NO 4
<211> LENGTH: 30
<212> TYPE: DNA
<213> ORGANISM: Rous sarcoma virus
<220> FEATURE:
<223> OTHER INFORMATION: PCR primer

<400> SEQUENCE: 4
tttggatcca tggggagtag caagagcaag                                      30

<210> SEQ ID NO 5
<211> LENGTH: 30
<212> TYPE: DNA
<213> ORGANISM: Rous sarcoma virus
<220> FEATURE:
<223> OTHER INFORMATION: PCR primer

<400> SEQUENCE: 5
tttgaattcc tactcagcga cctccaacac                                      30

<210> SEQ ID NO 6
<211> LENGTH: 26
<212> TYPE: DNA
<213> ORGANISM: Rous sarcoma virus
<220> FEATURE:
<223> OTHER INFORMATION: PCR primer

<400> SEQUENCE: 6
tgagaagctg gctcaactgt acgcag                                          26

<210> SEQ ID NO 7
<211> LENGTH: 26
<212> TYPE: DNA
<213> ORGANISM: Rous sarcoma virus
<220> FEATURE:
<223> OTHER INFORMATION: PCR primer

<400> SEQUENCE: 7
ctgcgtacag ttgagccagc ttctca                                          26

<210> SEQ ID NO 8
<211> LENGTH: 24
<212> TYPE: DNA
<213> ORGANISM: Rous sarcoma virus
<220> FEATURE:
<223> OTHER INFORMATION: PCR primer

<400> SEQUENCE: 8
ctacatcgtc gctgagtaca tgag                                            24

<210> SEQ ID NO 9
<211> LENGTH: 24
<212> TYPE: DNA
<213> ORGANISM: Rous sarcoma virus
<220> FEATURE:
<223> OTHER INFORMATION: PCR primer
```

-continued

```
<400> SEQUENCE: 9
ctcatgtact cagcgacgat gtag                                          24

<210> SEQ ID NO 10
<211> LENGTH: 26
<212> TYPE: PRT
<213> ORGANISM: Artificial Sequence
<220> FEATURE:
<223> OTHER INFORMATION: Description of Artificial Sequence:  Mutant
      v-Src ATP-binding domain, I338G

<400> SEQUENCE: 10

Arg His Glu Lys Leu Val Gln Leu Tyr Ala Val Val Ser Glu Glu Pro
 1               5                  10                  15

Ile Tyr Ile Val Gly Glu Tyr Met Ser Lys
            20                  25

<210> SEQ ID NO 11
<211> LENGTH: 26
<212> TYPE: PRT
<213> ORGANISM: Artificial Sequence
<220> FEATURE:
<223> OTHER INFORMATION: Description of Artificial Sequence:  Mutant
      v-Src ATP-binding domain, I338A

<400> SEQUENCE: 11

Arg His Glu Lys Leu Val Gln Leu Tyr Ala Val Val Ser Glu Glu Pro
 1               5                  10                  15

Ile Tyr Ile Val Ala Glu Tyr Met Ser Lys
            20                  25

<210> SEQ ID NO 12
<211> LENGTH: 26
<212> TYPE: PRT
<213> ORGANISM: Artificial Sequence
<220> FEATURE:
<223> OTHER INFORMATION: Description of Artificial Sequence:  Mutant
      v-Src ATP-binding domain, V323A,I338A

<400> SEQUENCE: 12

Arg His Glu Lys Leu Ala Gln Leu Tyr Ala Val Val Ser Glu Glu Pro
 1               5                  10                  15

Ile Tyr Ile Val Ala Glu Tyr Met Ser Lys
            20                  25

<210> SEQ ID NO 13
<211> LENGTH: 26
<212> TYPE: PRT
<213> ORGANISM: Artificial Sequence
<220> FEATURE:
<223> OTHER INFORMATION: Description of Artificial Sequence:  Mutant
      v-Src ATP-binding domain, V323A

<400> SEQUENCE: 13

Arg His Glu Lys Leu Ala Gln Leu Tyr Ala Val Val Ser Glu Glu Pro
 1               5                  10                  15

Ile Tyr Ile Val Ile Glu Tyr Met Ser Lys
            20                  25

<210> SEQ ID NO 14
<211> LENGTH: 26
<212> TYPE: PRT
<213> ORGANISM: Artificial Sequence
<220> FEATURE:
<223> OTHER INFORMATION: Description of Artificial Sequence: Mutant
``` v-Src ATP-binding domain, I338S

<400> SEQUENCE: 14

Arg His Glu Lys Leu Val Gln Leu Tyr Ala Val Val Ser Glu Glu Pro
 1               5                  10                  15

Ile Tyr Ile Val Ser Glu Tyr Met Ser Lys
            20                  25

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence:  Example
      sequence for enzyme modification

<400> SEQUENCE: 15

Asp Met Phe Arg Asp Lys Glu
 1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence:  Example
      sequence for enzyme modification

<400> SEQUENCE: 16

Asp Met Ile Arg Glu Lys Asp
 1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence:  Optimized
      enzyme inhibitor for Src kinases

<400> SEQUENCE: 17

Ile Tyr Gly Glu Phe Lys Lys Lys
 1               5

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence:  Optimized
      enzyme inhibitor for Abl

<400> SEQUENCE: 18

Glu Ala Ile Tyr Ala Ala Pro Phe Ala Lys Lys Lys
 1               5                  10

<210> SEQ ID NO 19
<211> LENGTH: 26
<212> TYPE: PRT
<213> ORGANISM: Homo sapiens
<220> FEATURE:
<223> OTHER INFORMATION: ATP binding domain of Fyn, residues 319-344

<400> SEQUENCE: 19

Lys His Asp Lys Leu Val Gln Leu Tyr Ala Val Val Ser Glu Glu Pro
 1               5                  10                  15

```
Ile Tyr Ile Val Thr Glu Tyr Met Ser Lys
            20                  25

<210> SEQ ID NO 20
<211> LENGTH: 26
<212> TYPE: PRT
<213> ORGANISM: Artificial Sequence
<220> FEATURE:
<223> OTHER INFORMATION: Description of Artificial Sequence:  Mutant Fyn
      ATP binding domain, T339G

<400> SEQUENCE: 20

Lys His Asp Lys Leu Val Gln Leu Tyr Ala Val Val Ser Glu Glu Pro
  1               5                  10                  15

Ile Tyr Ile Val Gly Glu Tyr Met Ser Lys
            20                  25
```

ENGINEERED PROTEIN KINASES WHICH CAN UTILIZE MODIFIED NUCLEOTIDE TRIPHOSPHATE SUBSTRATES

This is a divisional application of U.S. application Ser. No. 09/367,065, filed on Nov. 17, 1999, now U.S. Pat. No. 6,390,821, issued May 21, 2002, which is a U.S. National Phase Application of International Application PCT/US98/02522 filed Feb. 9, 1998, which is a continuation-in-part of U.S. application Ser. No. 08/797,522 filed Feb. 7, 1997 (now abandoned) and which claims benefit to U.S. Provisional Application No. 60/046,727, filed May 16, 1997, now abandoned.

The U.S. Government has a paid-up license in this invention and the right in limited circumstances to require the patent owner to license others, as provided for by the terms of NSF Grant No. MCB9506929 and DHHS NCI Grant No. R01CA70331-01.

I. FIELD OF THE INVENTION

The present invention is in the field of biotechnology. More specifically, the invention is in a field often referred to as enzyme engineering, in which through genetic alterations or other means, the amino acid sequences of enzymes of interest are changed in order to alter or improve their catalytic properties. The embodiments of the invention which are described below involve methods in the fields of genetic engineering and enzymology, and more particularly, to the design of protein kinases and other multi-substrate enzymes, including inhibitable such enzymes, and to related materials, techniques and uses.

II. BACKGROUND OF THE INVENTION

It is only logical that cell-to-cell communications in a multicellular organism must be fast, and that they must be able to allow cells to respond to one another in diverse and complex ways. Typically, the intracellular signals used are molecules called "ligands" and a given ligand can bind to a particular type of receptor on the surface of those cells that are to receive that signal. But this simple ligand binding alone is not enough to provide for the complex responses that the receiving cells may need to make. Cells therefore amplify and add complexity to this signal through complex, often cascading mechanisms leading to the rapid modulation of catalytic activities inside the cell, which in turn can produce complex, and sometimes dramatic, intracellular responses. This process as a whole, from initial ligand binding to completion of the intracellular response, is called "signal transduction." Signal transduction is often accomplished by the activation of intracellular enzymes that can act upon other enzymes and change their catalytic activity. This may lead to increases or decreases in the activity certain metabolic pathways, or may lead to even large intracellular changes, for example, the initiation of specific patterns of gene expression. The ability of one enzyme to alter the activity of other enzymes generally indicates that the enzyme is involved in cellular signal transduction.

The most common covalent modification used in signal transduction process is phosphorylation, which results in the alteration of the activity of those enzymes which become phosphorylated. This phosphorylation is catalyzed by enzymes known as protein kinases, which are often simply referred to as "kinases."

Several key features of the kinases make them ideally suited as signaling proteins. One is that they often have overlapping target substrate specificities, which allows "cross-talk" among different signaling pathways, thus allowing for the integration of different signals (1). This is thought to be a result of the need for each kinase to phosphorylate several substrates before a response is elicited, which in turn provides for many types of diverse signaling outcomes. For example, a given kinase may in one instance transmit a growth inhibitory signal and in another instance transmit a growth promoting signal, depending on the structure of the extracellular ligand that has bound to the cell surface (2).

A second key feature is that the kinases are organized into several modular functional regions, or "domains" (3). One domain known as "SH3" is a proline-rich region of 55–70 amino acids in length, and another, known as "SH2" is a phosphotyrosine binding region of about 100 amino acids in length. These two domains are believed to be involved in recognizing and binding to the protein substrates. The third domain, "SH1" is comprised of about 270 amino acids, and is the domain which is responsible for catalysis. It also contains the binding site for the nucleoside triphosphate which is used as energy source and phosphate donor (3). Other domains, including myristylation and palmitylation sites, along with SH2 and SH3, are responsible for assembling multiprotein complexes which guide the catalytic domain to the correct targets (3,22,23). Molecular recognition by the various domains has been studied using by x-ray diffraction and by using NMR methods (24–28).

These domains appear to have been mixed and matched through evolution to produce the large protein kinase "family." As many as 1000 kinases are thought to be encoded in the mammalian genome (4), and over 250 kinases have already been identified. The large number of kinases and the large number of phosphorylation-modulated enzymes that are known to exist inside cells allow for rapid signal amplification and multiple points of regulation.

A third key feature of the kinases is their speed. The kinetics of phosphorylation and dephosphorylation is extremely rapid in many cells (on a millisecond time scale), providing for rapid responses and short recovery times, which in turn makes repeated signal transmission possible (5).

These features of the kinases have apparently led them to be used in a vast array of different intracellular signal transduction mechanisms. For example, growth factors, transcription factors, hormones, cell cycle regulatory proteins, and many other classes of cellular regulators utilize tyrosine kinases in their signaling cascades (12,13). Tyrosine kinases catalytically attach a phosphate to one or more tyrosine residues on their protein substrates. The tyrosine kinases include proteins with many diverse functions including the cell cycle control element c-abl (14–16), epidermal growth factor receptor which contains a cytoplasmic tyrosine kinase domain (12), c-src, a nonreceptor tyrosine kinase involved in many immune cell functions (13), and Tyk2, a cytoplasmic tyrosine kinase which is involved in phosphorylation of the p91 protein which is translocated to the nucleus upon receptor stimulation and functions as a transcription factor (17). The serine/threonine kinases make up much if not all of the remainder of the kinase family; these catalytically phosphorylate serine and threonine residues in their protein substrates, and they have similarly diverse roles. They share homology in the 270 amino acid catalytic domain with tyrosine kinases. As such, although the discussion which follows focuses more particularly on the tyrosine kinases, that discussion is generally applicable to the serine/threonine kinases as well.

Unfortunately, the very features which make kinases so useful in signal transduction, and which has made them evolve to become central to almost every cellular function, also makes them extremely difficult, if not impossible, to study and understand. Their overlapping protein specificities, their structural and catalytic similarities, their large number, and their great speed make the specific identification of their in vivo protein substrates extremely difficult, if not impossible, using current genetic and biochemical techniques. This is today the main obstacle to deciphering the signaling cascades involved in tyrosine kinase-mediated signal transduction (4,6–8).

Efforts to dissect the involvement of specific tyrosine kinases in signal transduction cascades have been frustrated by their apparent lack of protein substrate specificity in vitro and in vivo (4,8). The catalytic domains of tyrosine kinases possess little or no inherent protein substrate specificity, as demonstrated by domain swapping experiments (18–23). The catalytic domain from one tyrosine kinase can be substituted into a different tyrosine kinase with little change in the protein substrate specificity of the latter (22).

The poor in vitro specificity of kinases also makes it difficult, if not impossible, to extrapolate what the in vivo function of given kinases might be. An isolated tyrosine kinase of interest will often phosphorylate many test protein substrates with equal efficiency (29). This apparently poor substrate specificity is also found in vivo; for example, many genetic approaches, such as gene knock out experiments, give no interpretable phenotype due to compensation by other cellular tyrosine kinases (30,31).

Another complication is that many tyrosine kinases have been proposed to phosphorylate downstream and upstream proteins which are themselves tyrosine kinases; although this appears to make complex positive feedback loops possible, it also makes dissecting the cascade even more difficult (1).

One important avenue for deciphering the role and understanding the function of enzymes, both in vitro and in vivo, is the use of specific enzyme inhibitors. If one or more compound can be found that will inhibit the enzyme, the inhibitor can be used to modulate the enzyme's activity, and the effects of that decrease can be observed. Such approaches have been instrumental in deciphering many of the pathways of intermediary metabolism, and have also been important in learning about enzyme kinetics and determining catalytic mechanisms.

In addition, such inhibitors are among the most important pharmaceutical compounds known. For example, aspirin (acetylsalicylic acid) is such an inhibitor. It inhibits an enzyme that catalyzes the first step in prostaglandin synthesis, thus inhibiting the formation of prostaglandins, which are involved in producing pain (72). Traditional drug discovery can be characterized as the design and modification of compounds designed specifically to bind to and inactivate a disease-causing protein; the relative success of such an effort depends upon the selectivity of the drug for the target protein and its lack of inhibition of non-disease associated enzymes with similar enzyme activities.

Such approaches would appear to be promising ways to develop treatments for cancer, since many human cancers are caused by disregulation of a normal protein (e.g., when a proto-oncogene is converted to an oncogene through a gene translocation). And since kinases are key regulators, they have turned out to be very common proto-oncogenes, and thus ideal drug design targets.

The process of designing selective inhibitors is relatively simple in cases where few similar enzymes are present in the target organism, for example in cases where inhibitors of a protein unique to bacteria can be targeted. But unfortunately, the similarities between the kinases and their large number has almost completely frustrated the discovery and design of specific inhibitors, and has blocked most hopes of developing specific pharmaceutical treatments aimed at the proto-oncogene level. It is expected that the vast majority of candidate inhibitors will inhibit multiple kinases, even though they may have initially been identified as inhibiting a particular, purified kinase.

This is not to say, however, that inhibitors with at least some degree of kinase specificity cannot be found. Several natural products have been identified which are relatively specific for particular kinase families, but attempts to derive general rules about kinase inhibition based on these has failed. Furthermore, as the following examples show, specificity in most cases is quite limited. For example, the compound Damnacanthal was reported to be a "highly potent, selective inhibitor" of the kinase p56lck (73); as shown in FIG. 10A, this compound has an inhibition constant ($IC_{50}$) for that kinase which is almost seven times lower than for the kinase src (the $IC_{50}$ is the concentration of inhibitor which must be added to reduce catalytic activity by 50%). The compound PPI (FIG. 10B) has a binding affinity for the kinase lck which is very strong ($IC_{50}$=0.005 $\mu$M); but unfortunately, the inhibition of other kinases of the src family is very similar. It inhibits the kinase fyn with an almost identical $IC_{50}$, 0.006 $\mu$M, and has only about a 4-fold higher $IC_{50}$ for the kinase hck ($IC_{50}$=0.020 $\mu$M). The compound CGP 57148 (FIG. 10C) has been reported to be "semi-selective" for the kinases abl ($IC_{50}$=0.025 $\mu$M) and PDGFR ($IC_{50}$=0.030 $\mu$M) (74). Nevertheless, considering the vast number of kinases and their relative cellular importance, and also considering that the above-described inhibitors have only been reported in the last two years, it appears that success in discovering or designing selective kinase inhibitors has been remarkably limited.

These difficulties described above have implications well beyond the mere frustration of scientists; they have frustrated efforts to decipher the kinase cascades and the function of individual kinases in those cascades and other cellular mechanisms. Such an understanding of kinase activity and function may be essential before certain human diseases can be effectively treated, prevented or cured. For example, it has been known for over thirty years that the oncogene bcr-abl is a protein kinase that is responsible for chronic myelogenous leukemia; but the physiological substrates that it acts upon to cause oncogenesis, which may be important drug design targets, have yet to be definitively identified (11). On the bright side, despite this shortcoming, the above-described inhibitor CGP 57148 is reportedly now undergoing clinical trials for use in treating myelogenous leukemia, even though the substrates it may block phosphorylation of in vivo are not known.

The medical significance of these difficulties is further illustrated by the Rous sarcoma virus (RSV), which has become an important model system for studying the role of kinases in oncogenesis. RSV transformation of fibroblasts is controlled by a single viral gene product, the protein tyrosine kinase v-src (32). It is the rapid time course and the dramatic morphological changes during RSV fibroblast transformation that have made RSV a paradigm for studies of oncogene activity in all cells. The origin (33), regulation (3,8,34,35), and structure (25,27,36) of v-Src have been extensively studied and are well understood (8,37,38). But central questions about this intensely studied kinase remains unanswered: what are its direct cellular substrates? Does inhibition of its catalytic activity effectively inhibit, or even reverse, transformation? Would such inhibition be an effective therapy for or prophylactic against RSV transformation? Unfortunately, as discussed above, the answers to these questions are not forthcoming, largely because the number of cellular kinases is enormous (it is estimated that 2% of the mammalian genome encodes protein kinases (4)) and because tyrosine kinases display overlapping substrate specificities (8,39) and share catalytic domains, making the design of specific inhibitors enormously difficult.

The expression of v-Src in fibroblasts results in the tyrosine phosphorylation of over fifty cellular proteins (37). These same substrates are also phosphorylated by other kinases in untransformed fibroblasts (40). Even the most sophisticated biochemical and genetic techniques, including anti-phosphotyrosine protein blots of transformed fibroblasts, transfection of fibroblasts with transformation-defective v-Src mutants, temperature-sensitive v-Src mutants, gene knock-out studies of cellular Src host-range dependent Src mutants, anti-v-Src immunoprecipitation, and use of kinase specific inhibitors, have not led to the unambiguous identification of direct substrates for v-Src (see reference (38) for a comprehensive review). But this situation is not unique; in fact, the direct substrates for the majority of cellular kinases remain unidentified (8). Furthermore, as discussed above, there also are remarkably few compounds known to selectively inhibit individual kinases, or even groups of related kinases.

Although the forgoing difficulties are daunting, new methods of rational drug design and combinatorial organic synthesis make the design or discovery of kinase-specific inhibitors feasible given sufficient resources. However, because the kinase networks are highly degenerate and interconnected in unknown ways, there is considerable uncertainty with regard to many diseases which kinases should be targeted for inhibition. Moreover, it is by no means clear that a specific inhibitor of a given kinase will have any effect on the disease, either in vitro or in vivo. Because kinases can be highly promiscuous, there is a significant chance that inhibiting one kinase will simply force another kinase to "take its place." Therefore, there is a need for a simple and direct way to determine the biochemical and cellular effects of inhibiting a given kinase, before herculean efforts are undertaken to design or discover specific inhibitors.

From the forgoing, it is clear that there has been a long felt but unsatisfied need for ways to identify which cellular proteins are acted upon by individual protein kinases. Such a method would ideally also allow for the quantitative measurement of relative activity of a given kinase on its protein substrates, which could be used, for example, to detect how or whether actual or potential drug compounds might modulate kinase activity. In addition, there has also been a need for specific inhibitors of individual kinases or kinase families, which could be used to identify protein substrates (by looking for which proteins are not phosphorylated or are more weakly phosphorylated in the presence of the inhibitor), to study the biochemical and phenotypic effects of rapidly down-regulating a given kinase's activity, for use as drugs to treat kinase-mediated diseases, and to confirm that tedious efforts to design or develop more traditional inhibitor drugs would be worthwhile. As is described in considerable detail below, the present invention for the first time provides a method for the highly specific inhibition of individual kinases, which have been engineered to bind the inhibitor more readily than the wild-type form of that kinase or other, non-engineered kinases. The invention also provides for the engineered kinases and the inhibitors to which they are adapted.

Moreover, as will become apparent, this method is even more broadly applicable, as it would provide similar advantages for the study of other enzymes which, like the kinases, covalently attach part of at least one substrate to at least one other substrate.

The present invention involves the engineering of kinases and other multi-substrate enzymes such that they can become bound by inhibitors which are not as readily bound by their wild-type forms. Modified substrates and mutant enzymes that can bind them have been used to study an elongation factor (41) and a receptor for cyclophilin A (42). However, prior to the present invention, it was not known how, or even if, multi-substrates enzymes which covalently attach part or all of a donor substrate onto a recipient substrate could be engineered to bind to an inhibitor, yet still retain at least some catalytic activity and at least some specificity for the recipient substrate in the absence of the inhibitor. The present invention is that this can be done, as explained below; and this invention for the first time opens the door to the selective inhibition of individual kinases, which are not only important tools for understanding of the kinase cascades and other complex catalytic cellular mechanisms, but also may provide avenues for therapeutic intervention in diseases where those mechanisms come into play.

III. SUMMARY OF THE INVENTION

The present invention provides a solution to the above-described problems by providing materials and methods by which a single protein kinase can be specifically inhibited, without the simultaneous inhibition of other protein kinases.

In a first aspect, the present invention involves the engineering of kinases and other multi-substrate enzymes such that they can utilize modified substrates which are not as readily used by their wild-type forms. The invention further provides such chemically modified nucleotide triphosphate substrates, methods of making them, and methods of using them. The methods of the present invention include methods for using the modified substrates along with the engineered kinases to identify which protein substrates the kinases act upon, to measure the extent of such action, and to determine if test compounds can modulate such action.

In a further aspect, the invention provides engineered protein kinases which can bind inhibitors that are not as readily bound by the wild-type forms of those enzymes. Methods of making and using all such engineered kinases are also provided. The invention further provides such inhibitors, methods of making them, and methods of using them. The methods of the present invention include methods for using the inhibitors along with the engineered kinases to identify which protein substrates the kinases act upon, to measure the kinetics of such action, and to determine the biochemical and cellular effects of such inhibition. They also relate to the use of such inhibitors and engineered kinases to elucidate which kinases may be involved in disease; these kinases can then become the subject of efforts to design or discover more traditional specific inhibitors of their wild-type forms, which may prove to be valuable in treating the kinase-related disease or disorder.

Furthermore, methods are provided for inserting the engineered kinase into cells or whole animals, preferably in place of the corresponding wild-type kinase, and then using the inhibitor to which it has been adapted as a tool for study of the disease kinase relationship, and ultimately, as a drug for the treatment of the disease.

The present invention also more generally relates to engineered forms of multi-substrate enzymes which covalently attach part or all of at least one (donor) substrate to at least one other (recipient) substrate. These engineered forms will accept modified substrates and inhibitors that are not as readily bound by the wild-type forms of those enzymes.

The invention also relates to methods for making and using such engineered enzymes, as well as the modified donor substrates. The methods of the present invention include methods for using the modified substrates and inhibitors along with the engineered enzymes to identify which substrates the enzymes act upon, to measure the kinetics of such action, and in the instance of the modified substrates, to determine the recipient substrates to which part or all of the donor substrate becomes attached, to measure the extent of such action, and to identify and measure the extent of modulation thereof by test compounds.

In the instance of inhibitors, the methods seek to determine the biochemical and cellular effects of such inhibition. The methods also extend to the use of such inhibitors and engineered enzymes to elucidate which enzymes may be involved in disease; these enzymes can then become the subject of efforts to design or discover specific inhibitors of their wild-type forms, which may prove to be valuable in treating the enzyme-related disease or disorder. Furthermore, methods are provided for inserting the engineered enzyme into cells or whole animals, preferably in place of the corresponding wild-type enzyme, and then using the inhibitor to which it has been adapted as a tool for study of the disease-enzyme relationship, and ultimately, as a drug for the treatment of the disease.

According to the present invention, through enzyme engineering a structural distinction can be made between the nucleotide binding site of a protein kinase of interest, and the nucleotide binding sites of other kinases. This distinction allows the engineered kinase to use a nucleotide triphosphate or an inhibitor that is not as readily bound by the wild-type form of that kinase, or by other kinases. In a preferred embodiment with respect to the inhibitor, the inhibitor used is one that is "orthogonal" to the "natural" nucleotide triphosphate substrate for that kinase, or is orthogonal to a less specific inhibitor (e.g., one which is readily bound by the wild-type form of that kinase). The term "orthogonal" as further discussed below, means that the substrate or inhibitor is similar in structure (including those that are geometrically similar but not chemically similar, as described below), but differs in a way that limits its ability to bind to the wild-type form.

An engineered kinase made according to the present invention will be able to use an orthogonal nucleotide triphosphate substrate that is not as readily used by other, nonengineered kinases present in cells. Preferably, it will be able to use an orthogonal nucleotide triphosphate that is not substantially used by other kinases; and most preferably, it will be able to use an orthogonal nucleotide triphosphate substrate that can not be used at all by other kinases. By labeling the phosphate on the orthogonal substrate, e.g., by using radioactive phosphorous ($^{32}P$), and then adding that labeled substrate to permiabilized cells or cell extracts, the protein substrates of the engineered kinase will become labeled, whereas the protein substrates of other kinases will be at least labeled to a lesser degree; preferably, the protein substrates of the other kinases will not be substantially labeled, and most preferably, they will not be labeled at all.

The detailed description and examples provided below describe the use of this strategy to uniquely tag the direct substrates of the prototypical tyrosine kinase v-Src. Through protein engineering a chemical difference has been made in the amino acid sequence which imparts a new structural distinction between the nucleotide binding site of the modified v-Src and that of all other kinases. The v-Src kinase Applicant has engineered recognizes an ATP analog (A*TP), $N^6$(cyclopentyl)ATP, which is orthogonal to the nucleotide substrate of wild-type kinases. The generation of a v-Src mutant with specificity for an orthogonal A*TP substrate allows for the direct substrates of v-Src to be uniquely radiolabeled using [γ-$^{32}P$] $N^6$(cyclopentyl)ATP, because it is able to serve as substrate to the engineered v-Src kinase, but is not substantially able to serve as substrate for other cellular kinases.

The detailed description and examples provided below describe the use of this strategy to uniquely identify the direct substrates of the prototypical tyrosine kinase, v-Src. Through protein engineering a chemical difference has been made in the amino acid sequence which imparts a new structural distinction between the nucleotide binding site of the modified v-Src and that of all other kinases. The engineered v-Src kinases that have been made and presented herein bind to an orthogonal analog of the more general kinase inhibitor PP3: the compound $N^4$ cyclopentyl PP3. The generation of a v-Src mutant with specificity for such an inhibitor allows for the mutant to be inhibited, whereas other kinases in the same test system are not substantially inhibited, not even the wild-type form of that same kinase.

As is apparent from the forgoing, it is one object of the present invention to provide a mutant protein kinase which accepts an orthogonal nucleotide triphosphate analog as a phosphate donor substrate.

Another object of the present invention to provide a nucleotide sequence which encodes such a mutant protein kinase; and it is a further object to provide a method for producing such a nucleic acid sequence.

It is also an object of the invention to provide methods for producing such a mutant protein kinase, for example, by expressing such a nucleic acid sequence.

It is also an object of the present invention to provide such orthogonal nucleotide triphosphates and methods for their synthesis, including $N^6$(cyclopentyl)ATP, $N^6$(cyclopentyloxy)ATP, $N^6$(cyclohexyl)ATP, $N^6$(cyclohexyloxy)ATP, $N^6$(benzyl)ATP, $N^6$(benzyloxy)ATP, $N^6$(pyrolidino)ATP and $N^6$(piperidino)ATP (27).

It is yet another object of the invention to provide a method for determining whether a test compound positively or negatively modulates the activity of a protein kinase with respect to one or more protein substrates.

More particularly, and in accordance with the further aspect of the invention, it is a primary object provide a mutant protein kinase which binds to and is inhibited by an inhibitor, which inhibitor less readily binds to or inhibits the corresponding wild-type kinase.

A further object of the present invention is to provide a nucleotide sequence which encodes such a mutant protein kinase; and it is a further object to provide a method for producing such a nucleic acid sequence.

It is also an object of the invention to provide methods for producing such a mutant protein kinase, for example, by expressing such a nucleic acid sequence.

It is another object of the present invention to provide such inhibitors, such as the compound $N^4$(cyclopentoyl) PP3, and methods for their synthesis.

Another object is to provide a method for determining what are the substrates for a given protein kinase.

It is yet another object of the invention to provide a method for determining whether specific inhibition of a particular kinase produces a biochemical or phenotypic effect in a test system such as a cell-free extracts, cell cultures, or living multicellular organisms.

It is a further object of the invention to provide a method to determine whether inhibition of a particular kinase might have therapeutic value in treating disease.

It is yet another object to provide methods for the study of the activity, kinetics, and catalytic mechanisms of a kinase by studying the inhibition of the corresponding mutant of the present invention.

A further object is to provide a methods of preventing and treating kinase-mediated diseases by introducing an inhibitor-adapted mutant kinase of the present invention into a diseased organism, and preferably diminishing or, most preferably, depleting the organism of the wild-type enzyme; and then administering the inhibitor to regulate the activity of the now disease-mediating mutant kinase so as to diminish or eliminate the cause or symptoms of the disease.

Based upon the forgoing and the detailed description of the present invention provided below, one of ordinary skill in the art will readily recognize that the present invention can be used more generally to study multi-substrate enzymes which covalently transfer a donor substrate or portion thereof to a recipient substrate, as do the kinases. Such applications of the present invention are also further described in the detailed description which follows.

Accordingly, it is yet a further object of the present invention to provide a mutant multi-substrate enzyme which binds to an inhibitor, which inhibitor is less readily bound to the wild-type enzyme or to other enzymes with similar activity.

It is another object of the invention to provide a nucleotide sequence which encodes such a mutant multi-substrate enzyme; and it is a further object to provide a method for producing such a nucleic acid sequence.

It is also an object of the invention to provide methods for producing such a mutant multi-substrate enzyme, for example, by expressing such a nucleic acid sequence.

It is also an object of the present invention to provide such inhibitors and methods for their synthesis.

Another object is to provide a method for determining what are the substrates for a given multi-substrate enzyme.

It is yet another object of the invention to provide a method for determining whether specific inhibition of a particular multi-substrate enzyme produces a biochemical or phenotypic effect in a test system such as a cell-free extract, cell culture, or living multicellular organism.

It is a further object of the invention to provide a method to determine whether inhibition of a particular multi-substrate enzyme might have therapeutic value in treating disease.

It is yet another object to provide methods for the study of the activity, kinetics, and catalytic mechanisms of a multi-substrate enzyme by studying the inhibition of the corresponding mutant of the present invention.

A further object is to provide a methods of preventing and treating multi-substrate enzyme-mediated diseases by introducing an inhibitor-adapted multi-substrate enzyme of the present invention into a diseased organism, and preferably diminishing or, most preferably, depleting the organism of the wild-type enzyme; and then administering the inhibitor to regulate the now disease-mediating mutant enzyme so as to diminish or eliminate the cause or symptoms of the disease.

These and other objects of the present invention will, from the detailed description, examples and claims set forth below, become apparent to those of ordinary skill in the art.

IV. BRIEF DESCRIPTION OF THE FIGURES

Figure 4:
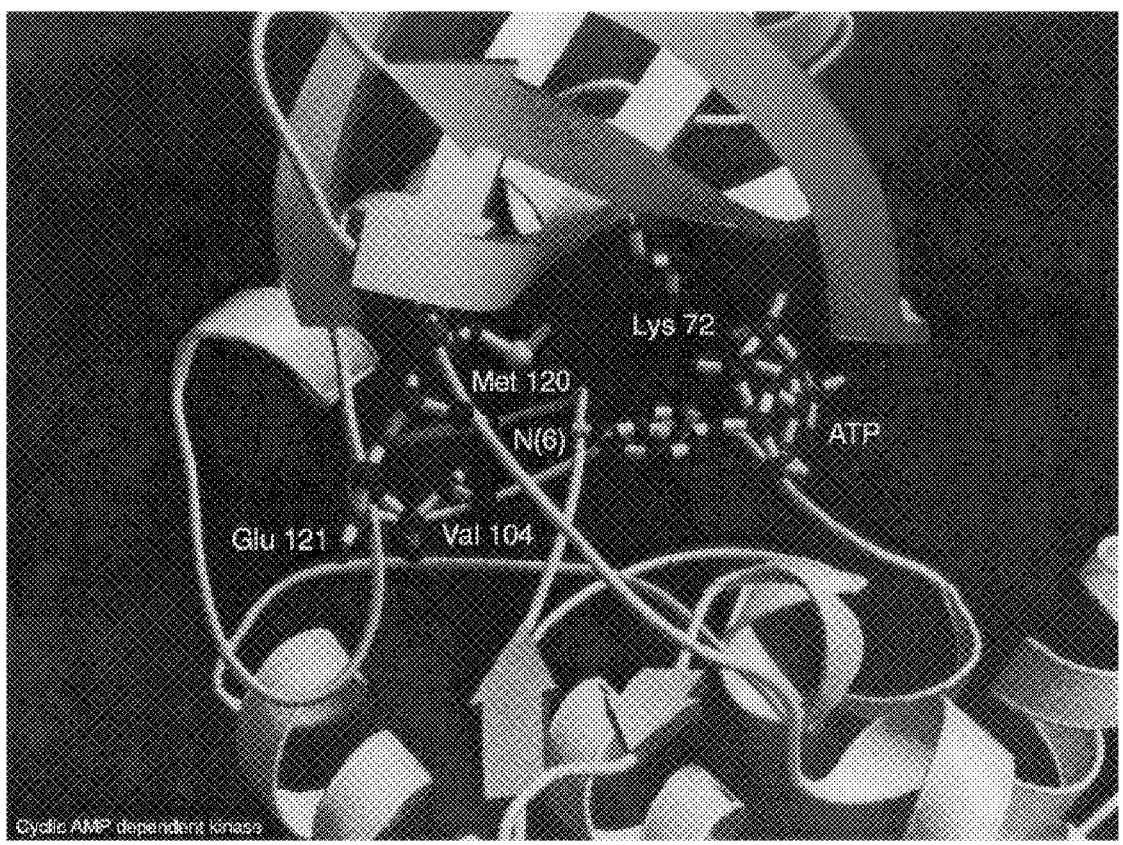
Figure 6:
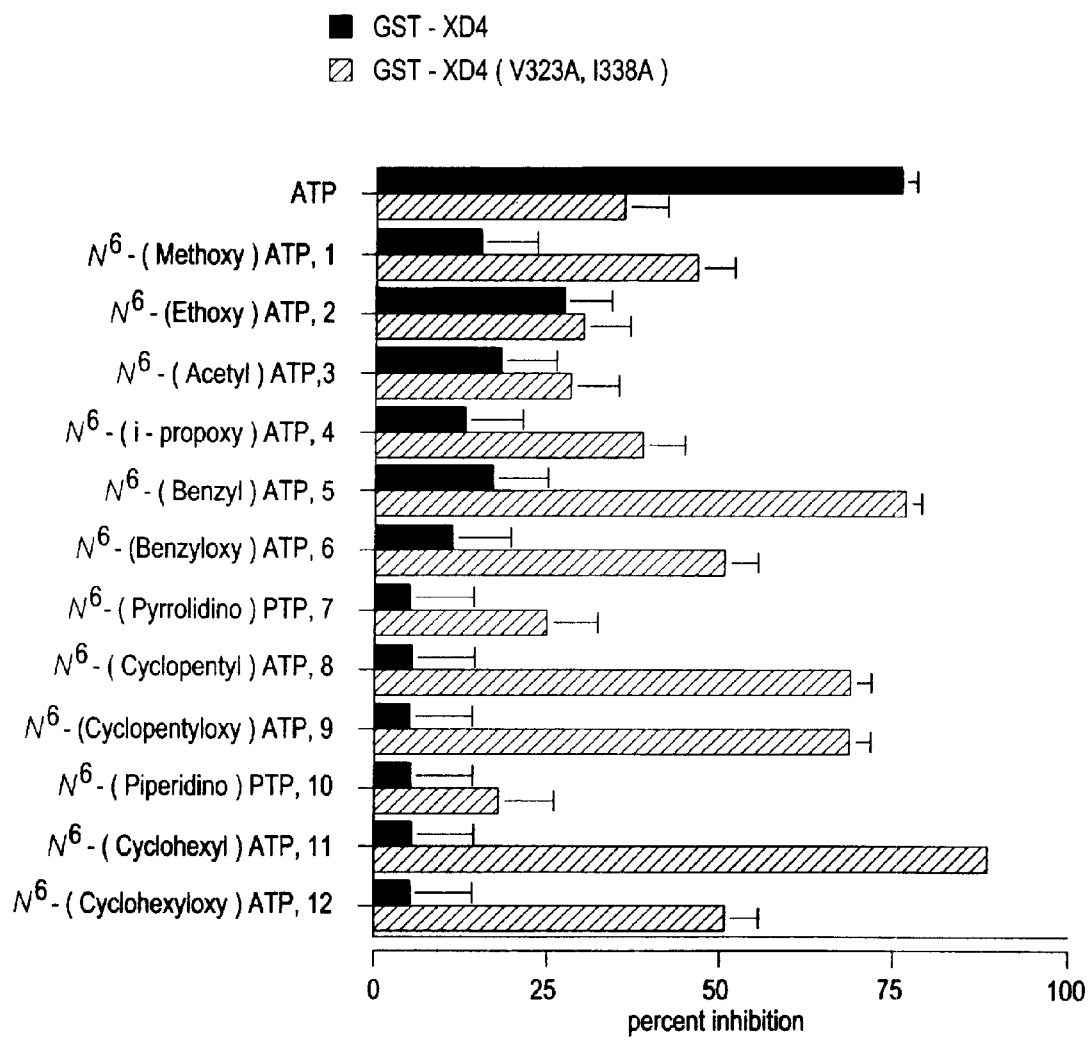
Figure 8:
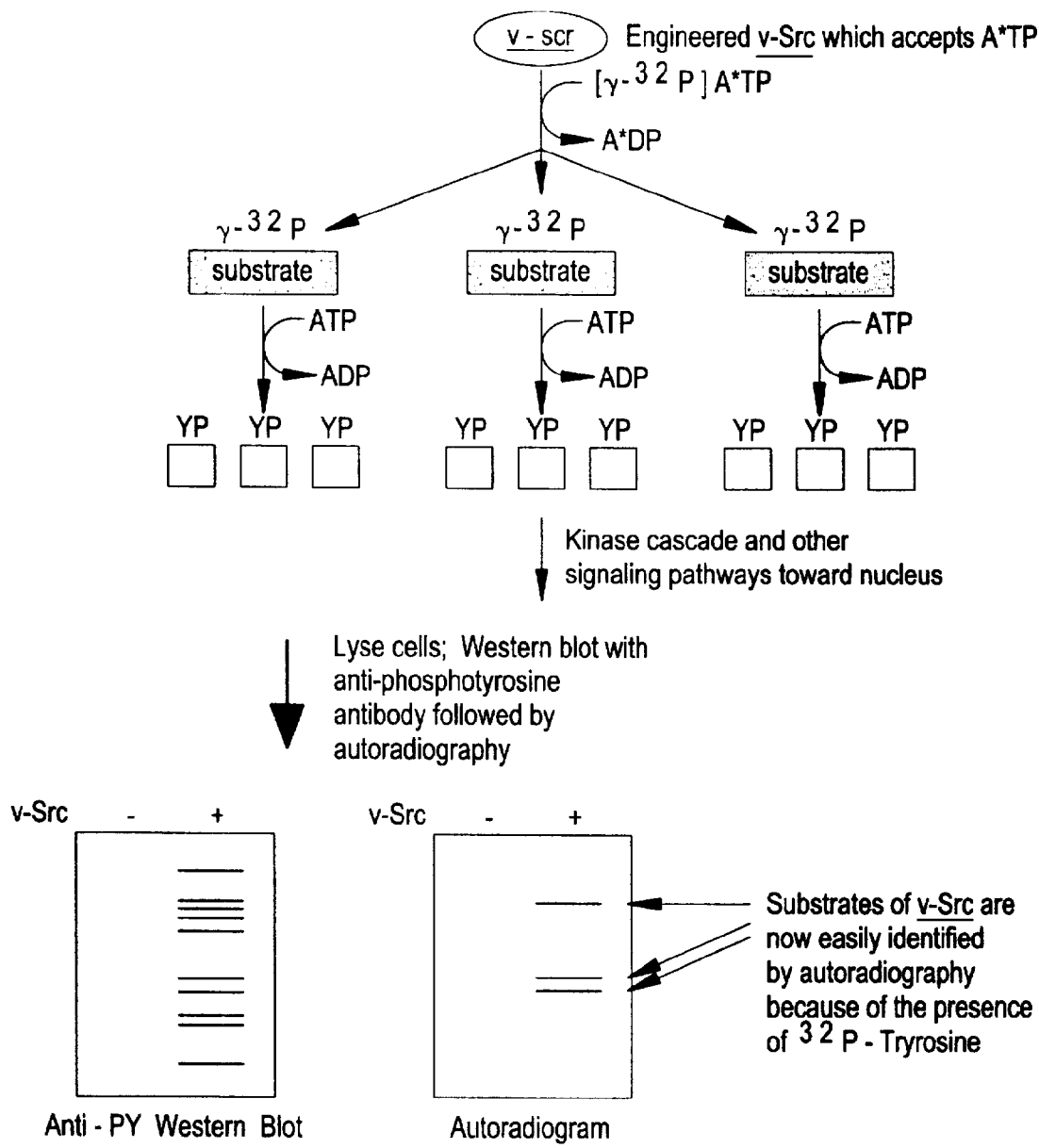
Figure 9:
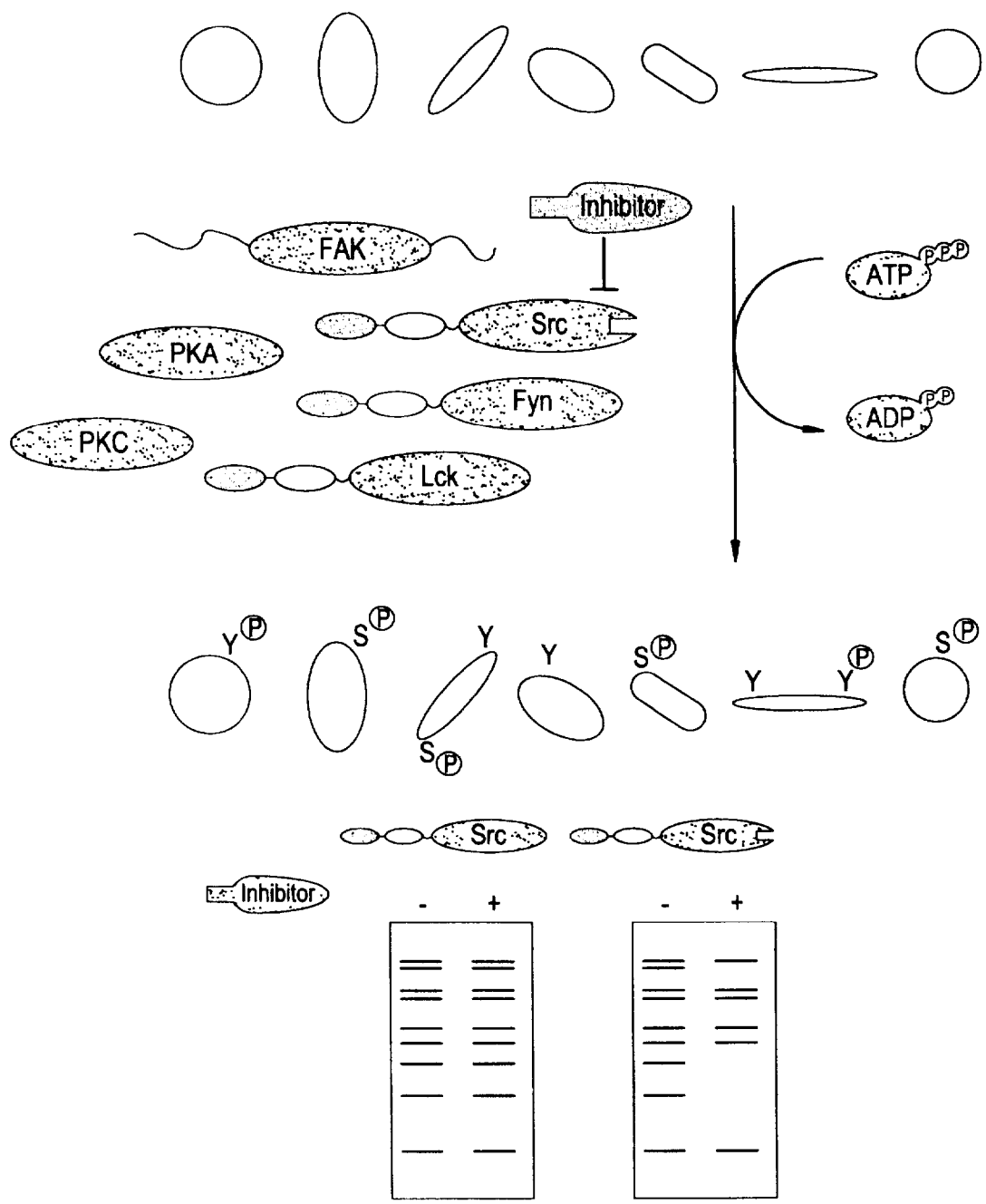
Figure 13A:
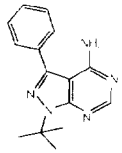
Figure 13A:
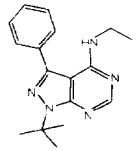
Figure 13A:
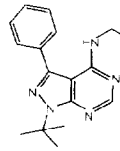
Figure 13A:
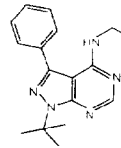
Figure 13A:
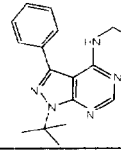
Figure 13A:
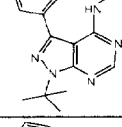
Figure 13A:
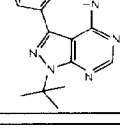
Figure 13A:
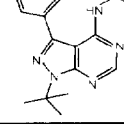
Figure 13A:
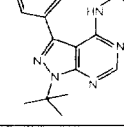
Figure 13B:
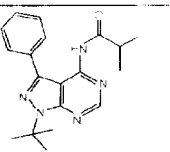
Figure 13B:
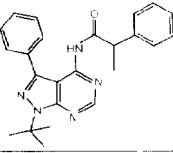
Figure 13B:
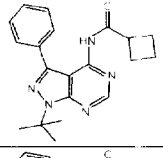
Figure 13B:
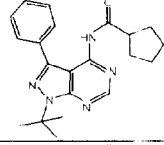
Figure 13B:
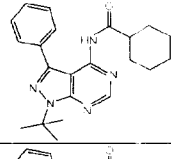
Figure 13B:
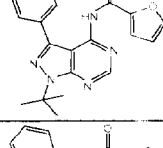
Figure 13B:
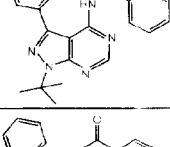
Figure 13B:
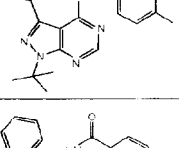
Figure 13B:
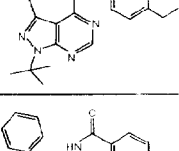
Figure 13B:
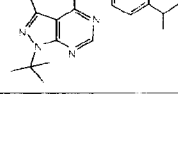
Figure 13C:
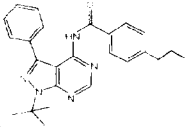
Figure 13C:
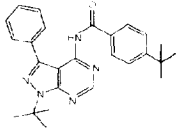
Figure 13C:
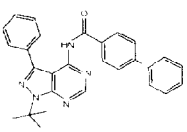
Figure 13C:
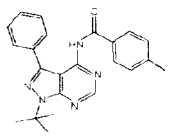
Figure 13C:
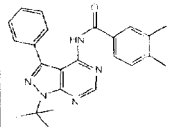
Figure 13C:
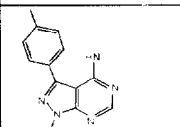
Figure 13C:
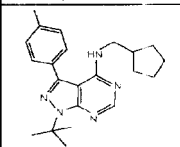
Figure 13C:
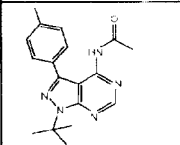
Figure 13C:
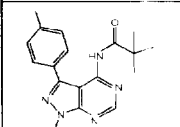
Figure 13C:
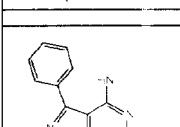
Figure 13D:
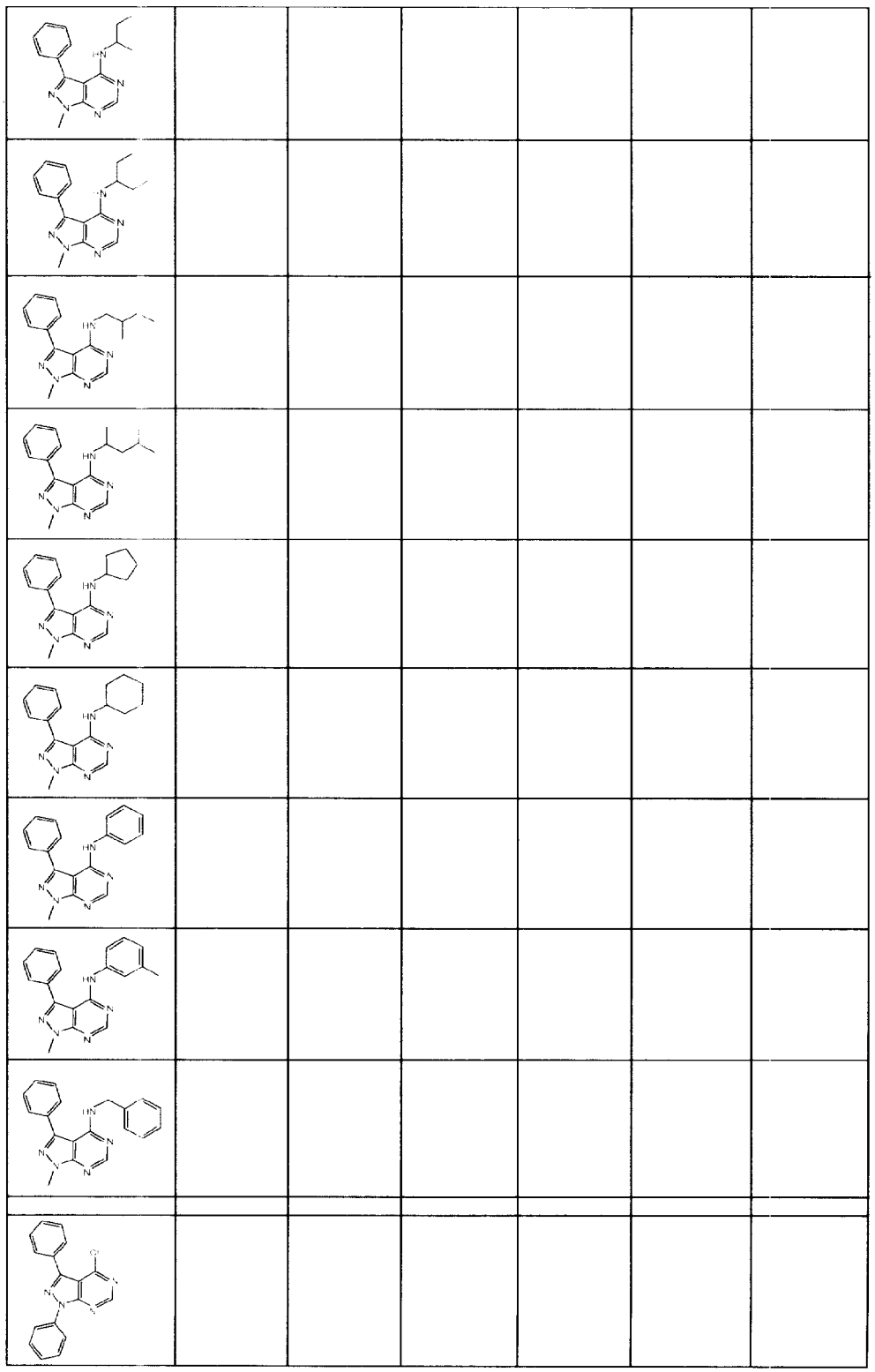
Figure 13E:
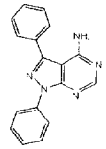
Figure 13E:
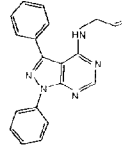
Figure 13E:
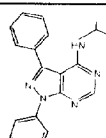
Figure 13E:
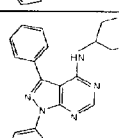
Figure 13E:
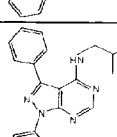
Figure 13E:
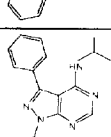
Figure 13E:
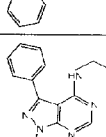
Figure 13E:
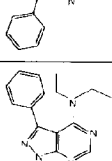
Figure 13E:
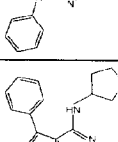
Figure 13E:
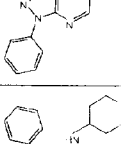
Figure 13F:
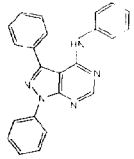
Figure 13F:
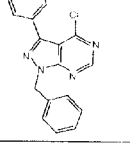
Figure 13F:
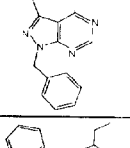
Figure 13F:
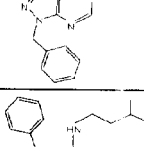
Figure 13F:
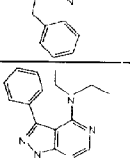
Figure 13F:
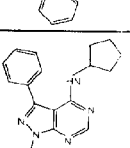
Figure 13F:
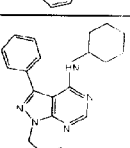
Figure 13F:
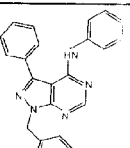
Figure 13F:

FIG. 4 provides a close-up view of the X-ray model showing the ATP binding domain in cAMP dependent protein kinase (1ATP);

FIGS. 5A–C shows (A) an anti-phosphotyrosine blot of cell lysates expressing XD4 and GST-XD4 (V323A, I338A) (SEQ ID NO: 12), (B) an autoradiogram showing levels of phosphorylation when cell lysates are provided only radiolabeled ATP or only radiolabeled $N^6$(cyclopentyl)ATP, and (C) an autoradiogram showing autophosphorylation of GST XD4 and GST-XD4 (V323A, I338A) (SEQ ID NO: 12) by radiolabeled ATP and radiolabeled $N^6$(cyclopentyl)ATP (A*TP(8));

FIG. 6 is a bar chart showing the relative degree to which ATP and each of the twelve ATP analogs inhibits GST-XD4 (SEQ ID NO: 3) and GST-XD4 (V323A, I338A) (SEQ ID NO: 12) catalyzed phosphorylation by radiolabeled ATP;

FIGS. 7A–D show autoradiograms indicating the levels of autophosphorylation by several v-Src position 338 single mutants (SEQ ID NOS: 10, 11 and 14) when provided with either radiolabeled ATP and radiolabeled $N^6$(cyclopentyl) ATP as phosphate donor substrate;

FIG. 8 is a schematic diagram of a method of the present invention for determining which phosphorylated substrates in cells were phosphorylated by a particular kinase, here v-Src;

FIG. 9 is a schematic diagram of how an engineered kinase of the present invention can be inhibited by an inhibitor of the present invention, even in the presence of other kinases, and can be used to reveal the kinase's protein substrates;

FIGS. 10A–C show the chemical structures for three known kinase inhibitors, Damnacanthal (10A), PPI (10B) and CGP 57148 (10C), along with summaries of their inhibition constants ($IC_{50}$) for several kinases;

FIG. 11A shows the core structure of adenosine and PP3; and

FIG. 11B shows the structures of several bulky substitutents which can be added to $N^4$ nitrogen of PP3 to produce the inhibitor candidate compounds whose $IC_{50}$ values are listed in Table 1; FIG. 11C shows in vitro inhibition data.

Figure 14:
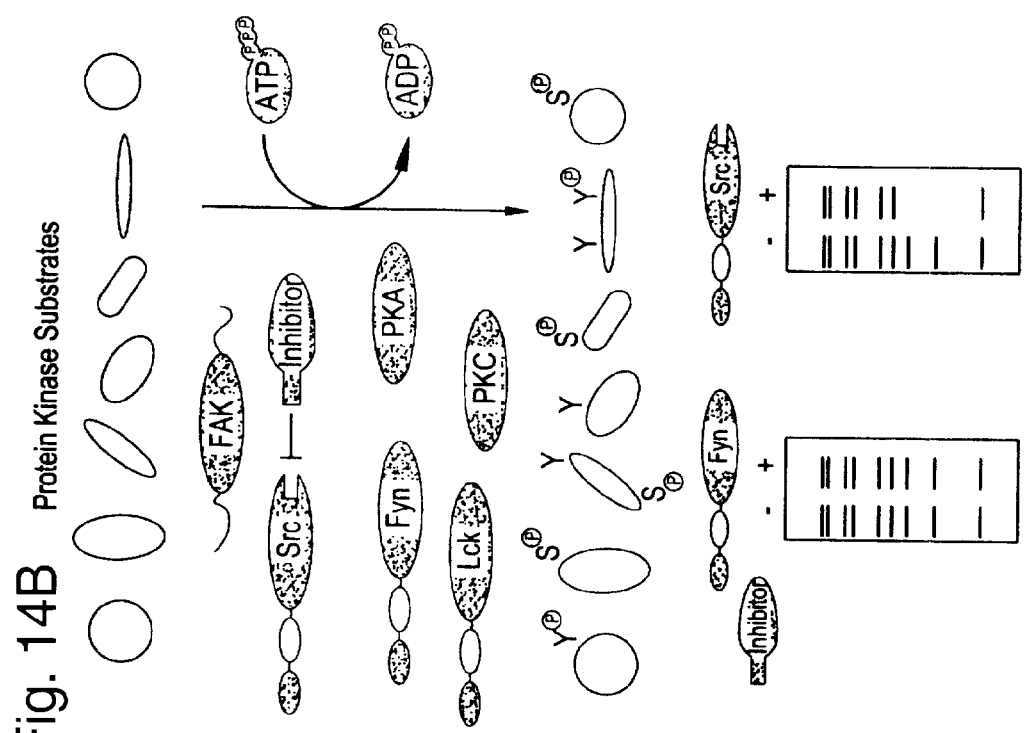
Figure 14:
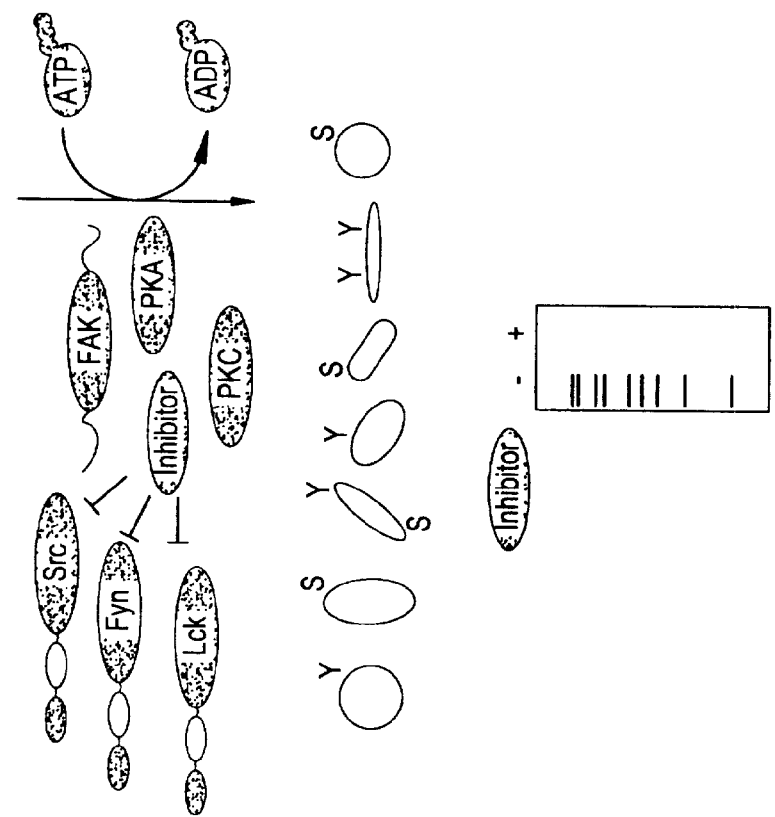

FIGS. 12A and B. FIG. 12A shows the chemical structure of $N^4$ cyclopentoyl PP3, and FIG. 12B shows autoradiograms of electrophoresed proteins which have become radiolabeled in the presence of $N^4$ cyclopentoyl PP3 in the presence of either wild-type v-Src (SEQ ID NO: 3) or the mutant (I338G) (SEQ ID NO: 10);

FIGS. 13A–F is a chart presenting additional inhibitor analogs prepared and tested in accordance with the present invention;

FIG. 14A is a schematic representation of the specificity problems associated with using small molecule protein kinase inhibitors to deconvolute cell signaling. Kinase catalytic domains are highly conserved. Thus, the majority of potent inhibitors block the activity of closely related kinases and broadly down regulate pathways mediated by kinase activity.

FIG. 14B is a schematic representation of the approach toward selective protein kinase inhibition described here. A space creating mutation is introduced into the ATP binding site of the kinase of choice (Src). This mutation creates an active site pocket (notch) in Src which can be uniquely recognized by a rationally designed small molecule inhibitor. This inhibitor contains a bulky chemical group (bump) which makes it orthogonal to wild type protein kinases. Design of the complementary kinase/inhibitor pair allows for highly selective inhibition of the target kinase in the context of a whole cell.

FIG. 15A—Structure of $N^6$ cyclopentyloxyadenosine (1). B. Synthesis of pyrazolo[3,4-d]pyrimidine inhibitor analogues. (2) was synthesized according to Hanefeld et al. (76), (I) RCOCl (10 equiv.), pyridine, 5° C., one hour; then warm to 22° C., eleven hours; (ii) LiAlH$_4$ (3.0 equiv.), dry THF under argon, 0° C., thirty minutes; then heat to reflux for thirty minutes. All compounds were characterized by $^1$H NMR (300 MHz) and high resolution mass spectrometry (EI).

FIG. 16A—Chemical structures of quercetin (5) and AMP PNP (6). B. Predicted binding orientation of (2) in src family kinase active sites. The crystal structures of Hck bound to AMP PNP and Hck bound to quercetin were superimposed according to the Hck protein backbone. The structure of (2) was subsequently docked into the kinase active site by superimposing the pyrazolo[3,4-d]pyrimidine ring system of (2) onto the adenine ring of AMP PNP. C. Predicted close contact between $N^4$ of (2) and the side chain of residue 338 in src family kinases. Molecule (2) has been docked into the ATP binding site of the Src family kinase, Hck, as in FIG. 16B. The atoms of the threonine 338 side chain, (2) and the Hck backbone are shown. The methyl hydrogens of the threonine side chain are not shown. Images were generated using the program InsightII.

Figure 17:
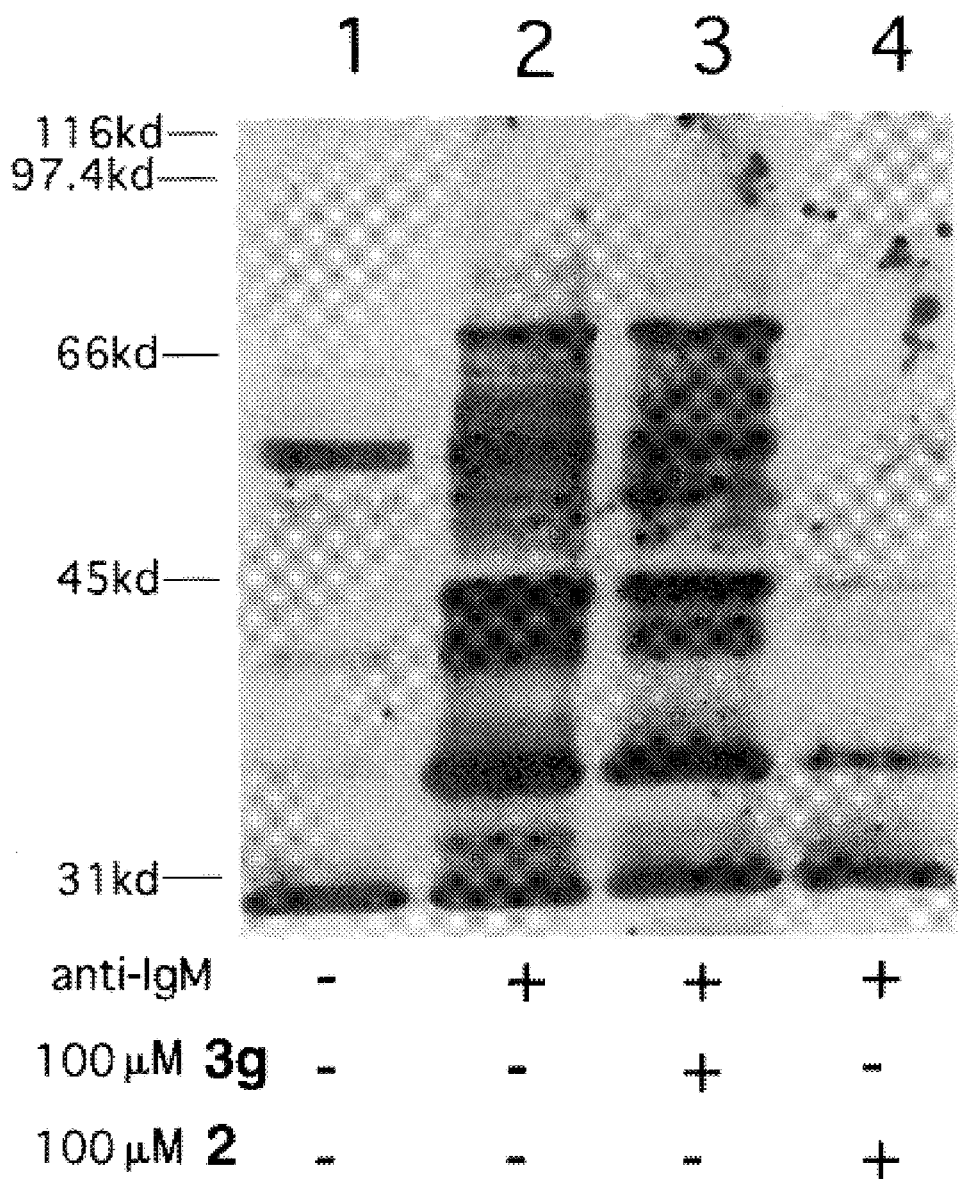

FIG. 17—Inhibitor analogue (3 g) does not inhibit B cell receptor mediated tyrosine phosphorylation. Murine spleen cells were incubated with 1.1% DMSO (lanes 1–2), 100 μM (3 g) in 1.1% DMSO (lane 3), or 100 μM (2) in 1.1% DMSO (lane 4). B cell stimulation (lanes 2–4) was initiated by the addition of 10 mg/ml goat anti-mouse IgM. Cellular proteins were resolved by 10% PAGE, transferred to nitrocellulose, and immunoblotted with a monoclonal antibody for phosphotyrosine (4G10).

Figure 18:
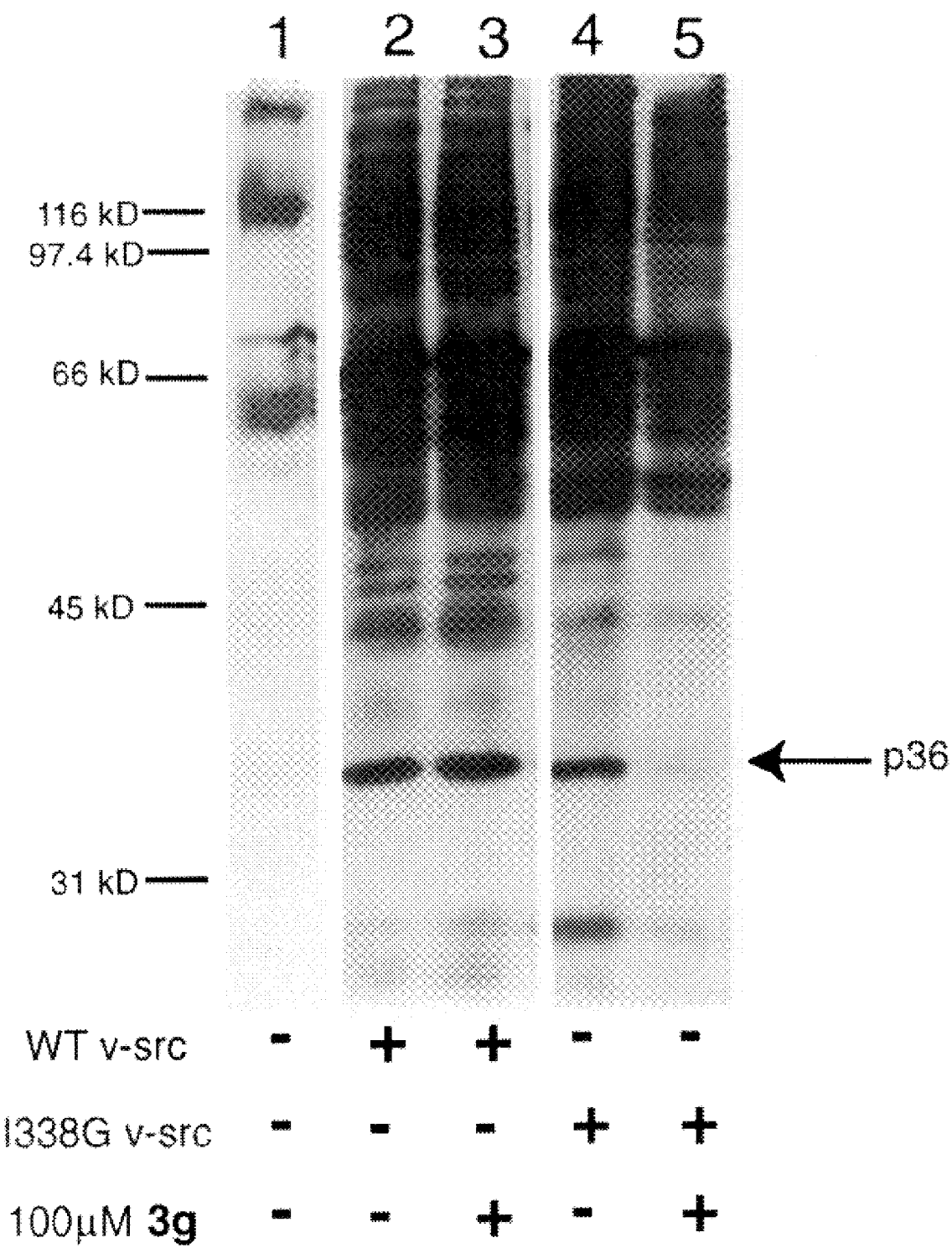

FIG. 18—Inhibitor (3 g) blocks p36 phosphorylation in I338G v-Src but not WT v-Src transformed NIH3T3 fibroblasts. Non-transformed NIH3T3 cells (lane 1), WT v-Src transformed NIH3T3 cells (lanes 2–3), and I338G v-Src transformed NIH-3T3 cells (lanes 4–5) were incubated with 1.1% DMSO (lanes 1, 2 and 4) or 100 μM (3 g) in 1.1% DMSO (lanes 3 and 5). After twelve hours, the cells were lysed. Phosphorylation levels were determined as described herein.

Figure 19:
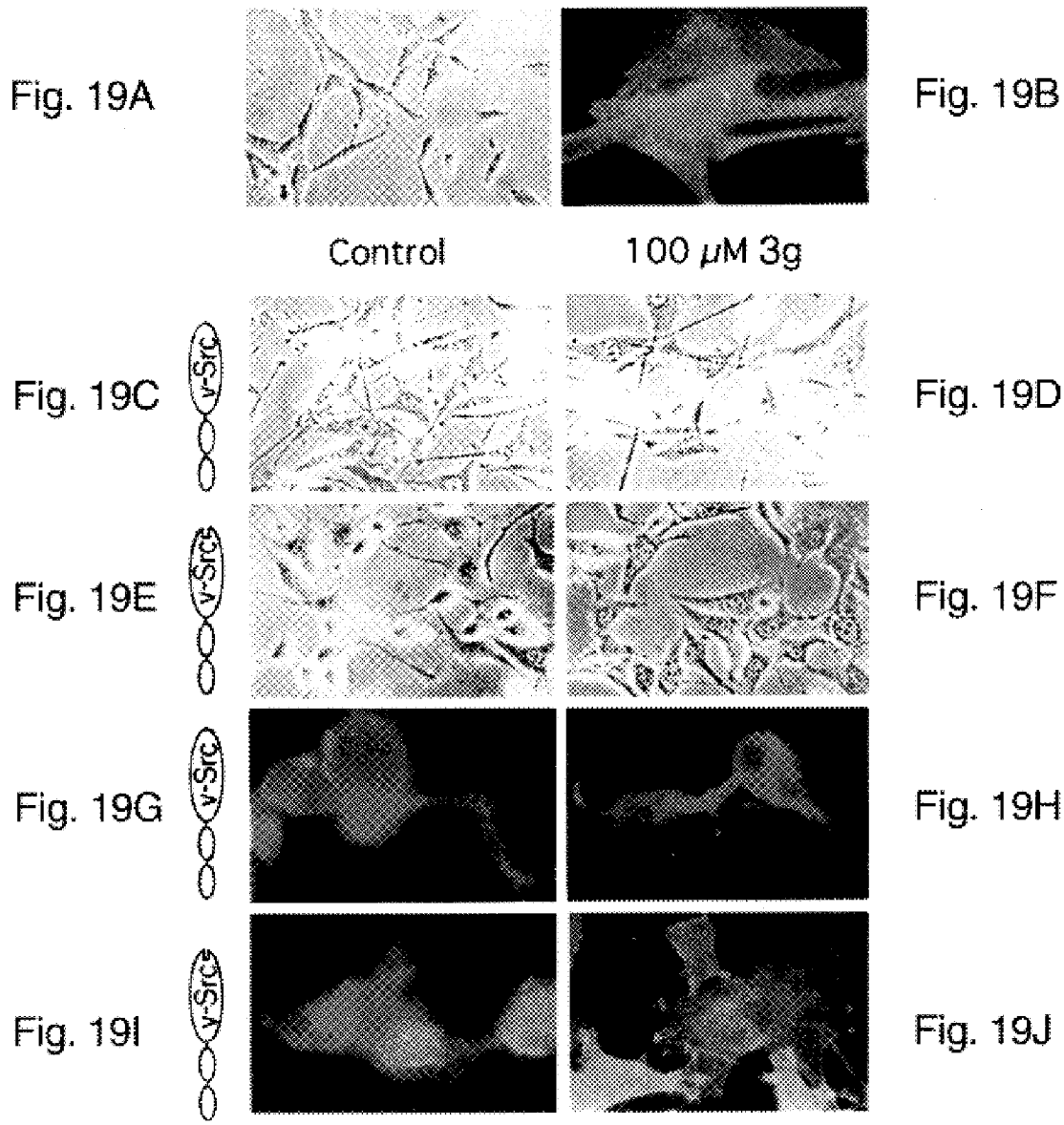

FIGS. 19 A–J. I338G v-Src transformed fibroblasts selectively acquire a flattened morphology and selectively regain actin stress fibers upon incubation with (3 g). Non-transformed (a–b), WT v-Src transformed (c, d, g, h) and I338G v-Src transformed (e, f, i,j) NIH-3T3 fibroblasts were treated with either 1.1% DMSO (a–c, e, g, i) or 100 μM (3 g) in 1.1% DMSO (d, f, h, j). After 48 hours cells were photographed (a, c–f), stained with phalloidin-FITC, and visualized (b, g–j) by fluorescence microscopy.

V. DETAILED DESCRIPTION OF THE INVENTION

Inhibition of Engineered Kinases

FIG. 9 shows a schematic representation of an experiment to identify kinase substrates below which uses the invention for discovery of the substrates of a Src protein kinase. The ovals at the top of the figure represent protein kinase substrates which become phosphorylated by the protein kinases adjacent to the arrow. The protein kinases containing several ovals connected by lines are members of the "Src-Family" of protein kinases (Src, Fyn, Lck). One kinase (Src) contains a notch cut out which represents the I338G mutation (SEQ ID NO: 10) which creates an extra space in the adenine binding pocket of this kinase. The symbol above this kinase represents the orthogonal inhibitor which contains a protrusion which complements the mutation in the Src I338G kinase (SEQ ID NO: 10), resulting in its unique inhibition. The kinase with a large round oval and two protruding stings is the F-Actin Dependent protein kinase (FAK). The protein kinases with only an oval are members of the serine or threonine specific protein kinase family. The ovals below the arrow containing small P's represent the phosphorylated (P) substrates after action by the protein kinases. The simulated gels at the bottom of the figure represent the expected results if cells expressing either all wild-type kinases (on left) or one mutant kinase (Src-I338G) (SEQ ID NO: 10) in place of wild-type Src are treated with the orthogonal inhibitor. The inhibitor should have no effect on the phosphoproteins present in the cells which do not express the mutant Src kinase (identical pattern in the gel on the left) and several phosphoproteins should be absent following treatment of the mutant expressing cells with the inhibitor (gel on the right).

The Inhibitors

FIGS. 11A and 11B show the structures of a variety of bulky substituents which, when added to either $N^4$ of PP3 or to $N^6$ of adenosine diphosphate, or to $N^6$ of adenosine monophosphate, or to $N^6$ of adenosine (specifically $N^6$ cyclopentyloxy adenosine) to produce inhibitors of the mutant kinase v-Src (T120G), which is an engineered kinase of the present invention; the synthesis and inhibition constants for these inhibitors are discussed in Example 12 below.

Such inhibitors may be useful in studies directed towards developing other useful mutants of this and other kinases, and for the several methods described elsewhere herein. However, the scope of the present invention is not limited to the use of these particular inhibitors, and those of ordinary skill in the art will recognize that many other possible structures could be substituted for or supplement those described herein.

For example, different, simpler, and even more complex aliphatic or aromatic groups could be added to the $N^6$ position of ADP or to the $N^4$ position of PP3. In addition, the inhibitors of the present invention are not limited to modifications of nucleotides at the $N^6$ position or modifications of PP3 at the $N^4$ position. Chemical means to modify various positions on such compounds are known, and any of the resulting derivatives would be within the scope of the present invention; it is even possible to make changes or substitutions in their ring structures. Exemplary variants are presented herein, and particular reference is made to FIG. 13 where both analogs and data relating to their activity is set forth. Of course, the use of such inhibitors may require that different positions in the protein sequence of the kinase be modified in order to make an engineered kinase that will bind to them, but such different modifications are well within the scope of the present invention.

In addition, it is important to note that the inhibitors of the present invention are not limited to ADP and PP3 derivatives. For example, it should be possible to utilize derivatives of other natural nucleotide phosphate donor substrate as such inhibitors. For studying some kinases, different analog bases may in fact be preferred. For example, it is known that some kinases utilize GTP as phosphate donor substrate and energy source; to make inhibitors for engineered forms of such kinases, analogs of guanosine diphosphate would be suitable. Furthermore, it is well known that related compounds (e.g., other bases) and compounds chemically unrelated to the natural substrate can sometimes nevertheless bind to an active site, and can (but for the purposes of this invention need not), be acted upon or act upon other substrates through chemical catalysis by the enzyme. Sometimes they participate in the catalyzed reaction in the same way as the natural substrate, sometimes in different ways. Such compounds and their derivatives would be suitable starting points for the design of inhibitors that are orthogonal to them, and which would be within the scope of the present invention. Similarly, other known kinase inhibitors can be used as a starting point for synthesis of inhibitors of the present invention, such as those whose structures appear in FIG. 10. Of course, even derivatives of inhibitors that are currently unknown would, once identified, be suitable core structures for the design of inhibitors of the present invention, as illustrated herein and made a part hereof.

Furthermore, the inhibitors of the present invention are not limited to those made by chemical synthetic means, but also include compounds which may be found in nature, and which can serve that role, some of which are discussed above. In addition, those of ordinary skill in the art will appreciate that there are other variations besides those set forth here, and that these are all within the scope of the present invention.

The inhibitors that are candidates for use in accordance with the present invention can conveniently be screened to determine the extent to which they are accepted by wild-type kinases, using a screening procedure such as that set forth in Example 13 below, or by a screening procedure involving the use of a cell or cells which are rich in protein kinase activity as set forth in Example 9 herein. By such an assay, one can determine whether each inhibitor is bound by wild-type kinases to a lesser degree than the engineered kinases, or preferably, if the wild-type kinases do not substantially bind to that inhibitor, or most preferably, do not bind the inhibitor at all. For those substrates that are least less readily bound, it may be worthwhile to try to engineer the kinase of interest so that it will more readily bind to them. Of course, one could make the engineered kinase first and then assay it along side the wild-type enzyme to determine whether it uses a given orthogonal substrate better than the wild-type kinase; this was the approach used in Example 13. However, under most circumstances, pre-screening as described above will be preferred. Of course, other assay approaches will be apparent to those in the field, and the use of such assays would be within the scope of the present invention.

The Engineered Kinases

There are several criteria that should be satisfied in reengineering a kinase in order to uniquely tag its authentic substrates in the presence of wild type tyrosine and serine/threonine kinases. The engineered kinase should: (1) accept an ATP analog (A*TP) that is utilized less readily by wild-type protein kinases; preferably, accept an A*TP that is not substantially utilized by wild-type kinases; and most preferably, accept an A*TP that is not utilized by wild-type kinases at all; (2) preferably, use the A*TP analog with high catalytic efficiency; and (3) preferably, have reduced catalytic efficiency for the natural nucleotide substrate (ATP) so that in the presence of cellular levels of ATP (1–2 mM) the mutated kinase would preferentially utilize A*TP as the phosphodonor. If such engineered kinases are to be used to study the protein substrate specificity of the wild-type kinase, then these criteria must be met without substantially altering the protein target specificity of the kinase.

Likewise several criteria should be satisfied in reengineering a kinase in order that it will be inhibited by the inhibitors of the present invention. The engineered kinase should: (1) bind to an inhibitor which is bound less readily by wild-type protein kinases; preferably, the inhibitor will not substantially bind to wild-type kinases; and most preferably, will not bind at all to wild type kinases; (2) preferably, the engineered kinase will bind the inhibitor with high affinity (i.e., low $IC_{50}$). It is not generally of particular importance whether the inhibitor binds to the wild-type form of the kinase that corresponds to the engineered kinase, as such binding and the resulting inhibition would augment that of the engineered kinase. However, it is most likely that the wild-type form of that kinase will not bind the inhibitor any better than other wild-type kinases. If an inhibitable engineered kinase is to be used to study the protein substrate specificity of the wild-type kinase, or to replace the wild-type form of that kinase through gene therapy or other means, as further discussed below, then a further concern is that the above-described criteria must preferably be met without substantially altering the protein target specificity of the engineered kinase when compared with the corresponding wild-type form.

When viewed from the perspective of the state of the art when the present invention was made, it was not predictable whether it would be possible to satisfy all of these criteria simultaneously; in fact, it was doubtful, because the ATP binding site that is engineered is very close to the second substrate binding site, i. e., the peptide binding site. However, as shown by the examples below, all of these criteria, including the preferred criteria, were in fact met simultaneously when Applicant made the described v-Src mutants, provided them with $N^6$(cyclopentyl)ATP and inhibited them using $N^4$(cyclopentyl)PP3.

Example 1 describes the twelve ATP analogs which were used in the studies on mutant v-Src, which are described in the further examples which follow. These orthogonal ATP analogs may be useful in studies directed towards developing other useful mutants of this and other kinases, and for the several methods described elsewhere herein. However, the scope of the present invention is not limited to the use of these particular ATP analogs, and those of ordinary skill in the art will recognize that many other possible orthogonal substrates could be substituted for or supplement those described herein. For example, different and even more complex aliphatic or aromatic groups could be added to the $N^6$ position of ATP. In addition, the orthogonal substrates of the present invention are not limited to modifications of nucleotides at the $N^6$ position. Chemical means to modify various positions on adenosine are known, and any of these would be within the scope of the present invention; and it is even possible to make changes or substitutions in the ring structures of nucleotides. Of course, the use of such orthogonal substrates may require that different positions in the protein sequence of the kinase be modified in order to make an engineered kinase that will bind to them, but such different modifications are well within the scope of the present invention.

In addition, it is important to note that the orthogonal substrates of the present invention are not limited to ATP derivatives. For studying different kinases different analog bases may in fact be preferred. For example, it is known that some kinases utilize GTP as phosphate donor substrate and energy source; for studies of such kinases, analogs of guanosine triphosphate would be preferred. It is well known that compounds chemically unrelated to the natural substrate can sometimes nevertheless bind to an active site, and can even be acted upon or act upon other substrates through chemical catalysis by the enzyme. Sometimes they participate in the catalyzed reaction in the same way as the natural substrate, sometimes in different ways. Such compounds and their derivatives would also be within the scope of the terms "natural substrate" and "orthogonal substrate" as used herein.

Furthermore, the orthogonal substrates of the present invention are not limited to those made by chemical synthetic means, but also include compounds which may be found in nature, and which can serve that role. Those of ordinary skill in the art will appreciate that there are other variations besides those set forth here, and that these are all within the scope of the present invention.

The orthogonal nucleotides that are candidates for use in accordance with the present invention can conveniently be screened to determine the extent to which they are accepted by wild-type kinases, using a screening procedure such as that set forth in Example 2 below. By such an assay, one can determine whether each orthogonal substrate is accepted by wild-type kinases to a lesser degree than the normal substrate for such kinases, or preferably, do not substantially accept that substrate, or most preferably, do not accept it at all. For those substrates that are least less readily accepted, it may be worthwhile to try to engineer the kinase of interest so that it will more readily accept them. Of course, one could make the engineered kinase first and then assay it along side the wild-type enzyme to determine whether it uses a given orthogonal substrate better than the wild-type kinase. However, under most circumstances, pre-screening such as is described in Example 2 will be preferred. Of course, other assay approaches will be apparent to those in the field, and the use of such assays would be within the scope of the present invention.

The design of an engineered v-Src is described in Example 3 below. As is described, the engineered form was designed by reference to the crystal structures of other kinases which have domains that are homologous to those found in most if not all kinases. As will be seen, the example mutant kinases described herein have been constructed as fragments of protein kinases, rather than as containing the entire sequences; but it was found there is no substantial difference in performance when the entire sequence is used. Of course, the concepts and the practicalities are the same whether fragments or whole kinases are used, and both are within the scope of the present invention. As such, the term "kinase" should be viewed as including the whole enzyme or a fragment of one, including when interpreting the claims.

Using this approach, it is possible to design similar mutants of virtually any other kinase. The method for doing this comprises the steps of: (a) identifying, from the crystal structure of an identical or homologous enzyme bound to its phosphate donor substrate or to a known kinase inhibitor (which may be non-specific for kinases, specific for kinases generally but not for that kinase, or specific for that kinase), one or more amino acids other than glycine which are close enough to a substituent on the bound phosphate donor substrate or inhibitor that they would sterically restrict entry of a bulky substituent attached to that substituent in a putative orthagonal inhibitor; and (b) mutating a nucleotide sequence which encodes the wild-type protein kinase such that the nucleotide triplets encoding one or more of the identified amino acids, are converted to nucleotide triplets that encode amino acids having side chains that are sterically less bulky than the identified amino acids.

The above-described method uses steric restriction of entry or exclusion as the criteria for deciding which amino acid(s) to change, and how to change them. However, the present invention is not so limited. It is also possible to engineer a kinase to change its ability to bind to an orthogonal substrate by considering other factors, such as hydrophobicity, hydrophilicity, ionic binding or repulsion, hydrogen bonding, forming covalent bonds between the enzyme and electrophilic groups on orthogonal substrates, etc.

The study of protein kinases using the present invention will be greatly facilitated by the vast knowledge regarding the domain structure of many different kinases, and their generally homologous sequences. The Protein Kinase Fact Book (Hardie & Hanks, (1995) Academic Press, San Diego) provides protein sequence data for the three functional domains in literally hundreds of protein kinases, and this along with sequence information available in the primary literature, should greatly facilitate the further application of the present invention to the kinases. Similar information is available regarding other multi-substrate enzymes, which should facilitate their study and use according to the present invention.

Although the preferred method of the present invention involves the rational design of substrate analogs and mutant protein kinases, both could alternatively be made by use of methods known as combinatorial methods. There are many combinatorial methods of synthesizing organic compounds. Using one such method, one could synthesize nucleoside analogs on resin beads using sequential chemical steps, and then release them from the resin prior to phosphorylation to make the nucleotide triphosphates. After using such a method to make a collection or library of putative orthogonal substrates for mutants of v-Src kinase, other protein kinase, or other multi-substrate enzymes, the collection or library could be screened for particularly favorable binding or catalytic properties. This may allow for the more thorough search of structural, conformational, and electronic features of such putative orthogonal substrates. Moreover, it is often found that when larger numbers of analogs of a given substrate are investigated, and unexpectedly efficient substrate or inhibitor can be found. Furthermore, sometimes the compounds which are the most desirable would not have been chosen if only well understood parameters were used to specifically design the best compound.

There are also many combinatorial methods known in the art for making protein mutants. These include "error prone" polymerase chain reaction (PCR), "sexual" PCR or PCR using primers with random nucleotides at fixed positions in the protein sequence. Other sequence randomization methods might include using chemical mutagens of cDNA or plasmid DNA, or MutD type strains of bacteria, which are known to introduce mutations randomly in proteins that they express. It would be possible to carry out the present invention by exploiting such methods for making randomly mutated protein kinases or other multi-substrate enzymes, and then screening for one with particularly high activity with a particular orthogonal substrate, or with some or all of the putative orthogonal substrates made using combinatorial synthesis, as described in the paragraph above. The assay methods described in the examples below would be suitable for this purpose, and those in the art would be readily able to design alternative approaches.

These methods and other methods which are or may be developed to explore protein sequence space and the structural space of small organic molecules might be particularly useful for the technological application described here, where one is changing or altering both the protein and the putative inhibitor in order to find the best possible non-natural (i.e., orthogonal) fit. The use of any of these or any of the other methods described herein would be within the scope of the present invention.

The synthesis of one engineered kinase is described in Example 4. The focus of this effort was on amino acid side chains that were within about 4 Å of the $N^6$ of ATP; but there is nothing magical about that distance. Residues with side chains that are within about 1 Å, 2 Å, 3 Å, 4 Å, 5 Å, 6 Å, 7 Å, 8 Å, 9 Å, 10 Å or lesser, greater or intermediate distances should also be considered as targets for modification. Amino acids with side chains that are within about 3 Å to about 6 Å would be preferred targets. Generally those amino acids with the closer side chains will be preferred over those with more distant side chains, as they would be expected to cause the greatest steric or other interference with the orthogonal substituent on the inhibitor; and those with the very closest side chains would be the most preferred.

Of course, there are many other ways to modify and express genetic sequences today than those used in the examples, such as site-directed mutagenesis, and one can expect that other methods will be developed in the future. The use of any or all of these would be within the scope of the present invention. In addition, although the use of genetic engineering is today probably the preferred method to prepare such mutants, it is not the only way. For example, one could design an engineered kinase and then synthesize that protein by known methods of chemical peptide synthesis. Or, it may be possible to chemically modify a given enzyme in a specific location such that one or more side chain changes in size, hydrophobicity, or other characteristic, such that it can more readily utilize an orthogonal substrate. The use of all such methods are within the scope of the invention.

Example 7 describes testing which could be done to determine whether the engineered kinase had retained its protein substrate specificity. It is preferred that the wild-type protein substrate specificity be substantially retained if, as in the examples, the goal is to use the engineered kinase to study what substrates the kinase acts upon and to what degree it does so, or it is to be used to replace or supplement the corresponding wild-type kinase in vivo, e.g., through genetic engineering. However, although for such purposes it is important that the kinase still recognize the same substrates as the wild type, it is not critical that it do so with the same kinetics; i.e., if it does so slower or faster, or to a greater or lesser degree, the engineered kinase may still have substantial value for such purposes. If the engineered kinase does not recognize the same protein substrates as the wild-type enzyme, it may have less value in studying the wild-type enzyme, but may still have substantial value in studying protein phosphorylation and kinases in general, and would still be within the scope of the invention.

Of course, the particular assays used in Example 7, although useful, need not be used. Those of skill in the art will readily be able to develop or adopt other assays that can provide comparable information.

Once a mutant kinase has been made which accepts a given orthogonal substrate analog, or which is inhibited by a given inhibitor, it can be characterized using classical enzyme kinetic analysis, as illustrated in Examples 5 and 6. Also, as shown in Example 8, one can study the degree to which the mutant can utilize or be inhibited by the analog, and whether the analog is a "dead" (i.e., wholly ineffective) inhibitor for the wild-type enzyme. Of course, the methods used in the examples are not the only ways these studies can be done, and those of skill in the art can easily design alternate approaches.

As illustrated in Example 10, it is not necessary to make multiple amino acid substitutions to provide a mutant that will be inhibited by an inhibitor of the present invention. It may only be necessary to make a single amino acid change, as is the case with the mutants GST-XD4 (I338A) (SEQ ID NO: 11) and GST-XD4 (I338G) (SEQ ID NO: 10).

Assay to Identify Kinase Substrates

A very simple embodiment of the present invention would be as follows. First, the orthogonal inhibitor is added to two samples of the cell of interest which either express an added gene for the engineered kinase or express the normal copy of the kinase of interest. The inhibitor can be added before, after, or during the activation of a signaling cascade (such as permeabilized cells, cell extracts, or cells that are naturally permeable to them). Then a method which allows detection of all phosphorylated proteins in a cell or cell fraction, e.g., by using radioactive phosphorous [$\gamma$-$^{32}$P] ATP or by using monoclonal antibodies specific for phosphorylated amino acids is used to reveal the result of specifically inhibition of the kinase of interest. In the cells expressing the normal copy of the kinase of interest, the protein substrates of the native kinase will become labeled, even in the presence of the inhibitor, whereas the protein substrates of the engineered kinase will at least be labeled to a lesser degree; preferably, the protein substrates of the engineered kinases will not be substantially labeled, and most preferably, they will not be labeled at all.

It is also preferable if the wild-type kinase corresponding to the mutant has been removed from the cells, e.g., by "knock-out" of the cellular gene(s) for it. If the labeled proteins of such an assay are examined in tandem with control samples containing the wild-type kinase but not the mutant kinase, certain bands will be diminished in intensity in the mutant-treated sample relative to the control. Preferably, the difference in intensity will be high; most preferably, there will be bands which are missing in the mutant-containing samples treated with the inhibitor. This would indicate that the wild-type form of that kinase phosphorylates those differentially labeled proteins; when the kinase is inhibited, those bands do not get labeled.

Example 10 provides one example of a method of using a mutant kinase of the present invention, along with its orthogonal substrate analog or its inhibitor, as the case may be, to detect which are the intracellular protein substrates for that protein kinase. Developing such a test was a primary goal of the research that led to the present invention.

Generally, the method described in Example 10 and in FIG. 8 would appear to be generally applicable; however, there are many other possible approaches that could be used, once a mutant that accepts an orthogonal substrate analog or inhibitor has been prepared. The natural phosphate donor substrate is first prepared to contain a labeled moiety on the terminal phosphate, for example, by replacing the phosphate with [$\gamma$-$^{32}$P] phosphate. This substrate, along with the analog or inhibitor, is then added to a sample of lysed cells, cell extracts, permiabilized cells, or cells which are naturally permeable to the orthogonal nucleotide triphosphate substrate analog or to the inhibitor, and which express the mutant kinase, or to which the mutant kinase has been exogenously added (e.g., by microinjection). After incubation under conditions that will allow the mutant kinase to become inhibited, and/or to phosphorylate its protein substrates to the extent not inhibited, the labeled products are then extracted and analyzed in comparison with those produced by a control sample, which was treated substantially the same way, but without the addition of the analog or inhibitor, respectively. Methods for the detection of labeled proteins are well known, and include both quantitative and qualitative methods. In addition, all methods for characterizing and identifying proteins can be used to determine with specificity what the protein substrates are, and what their functions are. Ultimately, it should be possible to develop an understanding of what protein substrates each of the various protein kinases act upon, and reveal in great detail the mysteries of cellular signal transduction.

Once one or more cellular protein substrate has been identified, similar assays can be used to identify drugs or other compounds that can modulate the activity of a given protein kinase on one or more substrates. For example, one could add small amounts of solutions of a variety of such compounds to test samples containing cell-free extract, mutant kinase, along with a labeled orthogonal substrate analog and/or inhibitor. The labeled proteins can then be identified, e.g., by gel electrophoresis followed by autoradiography, and compared with a duplicate test sample treated the same way, but to which no drug or other compound was added.

If a protein is not labeled in a sample having an added compound plus substrate analog and/or inhibitor that does get labeled in a sample treated with the analog and/or the inhibitor, this indicates that the added compound has caused the kinase to phosphorylate a protein that it does not act on in the absence of the compound, i.e., the compound upwardly modulates the activity of the kinase for that protein. Alternatively, if a labeled protein appears in a test sample to which the compound or drug was added, but does not appear in a test sample not having the compound or drug added, this indicates that the added compound has prevented the kinase from phosphorylating a protein that it does act on in the absence of the compound, i.e., the compound downwardly modulates the activity of the kinase for that protein substrate.

Furthermore, if quantitative measurements are made for each labeled protein, e.g., by scanning autoradiograms and integrating the data, more subtle effect on kinase activity can be detected. For example, it may be found that a protein is more fully or less fully phosphorylated in the presence or absence of a given compound (i.e., has been less dramatically modulated). It can also be expected that some compounds will upwardly modulate kinase activity for some proteins and downwardly modulate activity for others at the same time.

Use in Screening for Drug Design Target Kinases

As mentioned above, because kinases play key roles in various diseases, it is of great interest to develop inhibitors which can specifically inhibit a single wild-type kinase or group of wild-type kinases. By down-modulating the activity of these diseases involved kinases, it should be possible to reduce the disease symptoms, or even cure the disease.

However, the great difficulty which has been experienced in making such inhibitors of wild-type kinases, as briefly described above, limits the potential of that approach. The primary difficulty is finding inhibitors which are specific, and do not inhibit other kinases than the intended target. The reasons for such non-specificity are (i) the nucleotide triphosphate binding sites of kinases are highly conserved in evolution, and (ii) many kinases are "degenerate" that is, they have sufficiently similar activities and specificities that they can substitute for other kinases that because of gene deletion or other reason are absent or diminished in concentration in the cells. The problem of binding site similarities can in many instances be overcome, e.g., by careful rational inhibitor design, or by selection of inhibitors from combinatorial libraries on the basis of specificity. However, efforts to do so with a kinase that is truly degenerate with another kinase will likely be unfruitful; either all of the co-degenerate kinases will be inhibited by even the best candidate compounds, or even if the target is inhibited, it will be impossible to tell, because a degenerate kinase will "take over" the activity of the inhibited one.

Because of this, there is a need for a way to screen kinases to determine which wild-type kinases are degenerate, and thus probably poor candidates for specific inhibition, and which are not degenerate, and therefore preferred candidates for specific inhibition. The present invention provides such a method. The present invention provides a means to generate a specific, unique kinase inhibitor for any kinase of interest, by making a mutant of the kinase that is specifically designed to be inhibited by candidate inhibitors selected, and then studying the effects of that inhibition.

One way to accomplish this is to test cells or cell extracts in vitro. For example, one could add ATP to such a sample which has one kind of label (the "first label") on the terminal phosphate, and add the specific inhibitor which is differently labeled (the "second label") at the terminal phosphate. The decrease in appearance of the second label on a given protein substrate (e.g., as viewed by gel electrophoresis) indicates specific inhibition of the mutant kinase; and appearance of the first label on that same substrate indicates that the other kinases have taken over that phosphorylation role, the degree of which is shown by the relative degree of such labeling. If it turns out that the engineered kinase is specifically inhibited, and other kinases do not take over phosphorylation of the substrates of the engineered kinase when it is inhibited, or at least do not completely take over, then that kinase is not degenerate, or at least not completely so; it is thus probably not a good candidate for development of a specific inhibitor of the wild-type for use as a drug to treat the disease it relates to. However, if inhibition of the mutant kinase with an inhibitor of the present invention is not compensated for by the other kinases, then it is a preferred candidate for the development of an inhibitor of the wild-type kinase.

Another, preferred method of such screening would be to produce animal models for the disease of interest, and then "knock out" the wild-type gene, and then, by genetic engineering, insert into the genome a gene encoding a mutant kinase of the present invention "knock-in". Then, an inhibitor of the present invention, preferably one which has been shown in vitro to inhibit the mutant, can be used to down-regulate the mutant kinase. If down regulation leads to a decrease in the symptoms or morbidity of the disease in the model animal, or eliminates the disease, then that kinase is a preferred candidate for the development of a specific inhibitor of the wild-type form.

Gene Therapy Applications

The mutant kinases and inhibitors of the present invention can also be used directly to treat diseases in humans and animals. Just as described above for the animal model systems, gene substitution could be used on patients with diseases which are mediated by those kinases. The wild-type gene for one or more such wild-type kinase would be deleted, e.g., by "knock-out" methods known in the art, and then specifically inhibitable mutants of those one or more kinases would be added to the animal's genome, e.g., by "knock-in" or gene therapy methods which are known in the art. Then, the inhibitor could be used as a drug to down-modulate those one or more mutant kinases, such that the disease is ameliorated to at least some degree, but the degree of activity of those kinases which may be found to be necessary for normal cellular function could be maintained. Of course, the kinases could also be essentially "turned off" by strong inhibition, if that proved to be therapeutically effective. Furthermore, if it is found that the disease is greatly improved or cured by a period of down-regulation or being turned off, then administration of the inhibitor could be discontinued, and the disease well might not return or exacerbate. If not, then inhibition could be discontinued on a long term or even permanent basis, and the mutants could be left to function in the place of the wild-type kinase for the remainder of that patient's life. Since the specific inhibitors of the present invention are not present in the environment, the mutant kinases should behave just like the wild-type (except to the extent that the engineering may have changed their activity or kinetics). And if the disease should recur or flare up again in the future, the patient could again be treated with the inhibitor, without the need to repeat the gene exchange.

Other Multi-Substrate Enzymes

As mentioned above, the present invention is not limited to mutant kinases, orthogonal inhibitors, and their synthesis and use. The present invention will work just as well for other multi-substrate enzymes which covalently transfer part or all of one substrate, here called the donor, to another substrate, here called the recipient; and there are surely more such enzymes yet to be discovered. In any such instance, one of skill in the art who has studied the present specification will well appreciate the applicability of the present invention to such enzymes. The tasks at hand in such an instance are quite similar to those described in detail here for the kinases. First, it is necessary to identify what the donor substrate is, and/or to identify compounds which can inhibit that kinase, even if it is not specific for that kinase.

Second, it is necessary to consider where a bulky substitutent might be added to the substrate or the inhibitor such that it will not bind as readily to the wild-type kinase, or preferably will not bind substantially to the wild-type kinase, and preferably, will not bind at all. Of course, it is not really necessary, in the case of kinases or in other multi-substrate enzymes as described above, to be restrictive with respect to which analogs of these to make; one can make a variety of them, even including some that seem unlikely to be ideal, and determine by screening which one or ones are the best. Further guidance regarding how to do this can be gained from the examples below. The inhibition assay, the results of which are shown in FIG. 6, is a non-limiting example of an assay particularly well suited to such screening.

The third step is to engineer the kinase such that one or more amino acid in the three-dimensional location where the bulky group would be expected to be if the analog did bind are replaced with amino acids having less bulky side chains, thus "making room" for the bulky moiety of the inhibitor. Steps two and three can, of course, be carried out in the reverse order.

For example, transferase enzymes would be most interesting candidates for study using the present invention. One could, following the teachings provided herein, prepare mutant transferases which will accept orthogonal inhibitors, and these could be used together in order to identify the direct substrates of one particular transferase in a large family of homologous transferases, by the methods described above for the kinases. The family of methyltransferases would be of clear interest, and could quite easily be studied using the methods provided herein. These enzymes all use the same nucleotide based cofactor, S-adenosylmethionine (AdoMet), as a methyl ($CH_3$) group donor. The different members of the family can transfer the methyl group of AdoMet to a wide variety of cellular components such as proteins (in which case the methyl group is added to arginine, aspartate, and glutamate side chains), DNA (in which case the methyl group is added to the $C^5$ position of cytosine, or the $N^7$ of guanine), to components of cell membrane components such as phospholipids, and also to a number of small amine containing hormones. Many new targets are also being identified for this diverse family of enzymes. The present invention provides the opportunity to decipher the tremendously complex cellular mechanisms that these enzymes are carrying out.

For example, one could synthesize a set of AdoMet analogs that contain additional bulky hydrophobic groups at the $N^6$ position, or at other ring positions, which would make the analogs orthogonal, and thus not be accepted as readily by wild-type methyltransferases as is the natural substrate; and the structure in the region of the transferred methyl group might be altered such that the methyl group is more chemically resistant to transfer; or, for example, S-adenosylcysteine might be used as the starting compound instead. Using the crystal structures of DNA methyltransferase M. HhaI and the catechol methyltransferase catechol O-methyl-transferase (COMT), one can identify those amino acids in the adenine binding pocket which are candidates for mutation as Applicant has done for the protein kinases; and one of ordinary skill in the art should readily be able to identify a set of residues to mutate in order to accommodate the bulky hydrophobic groups of one or more of the orthogonal substrates.

For example, one might mutate large hydrophobic groups to smaller alanine or glycine residues, or replace hydrogen bonding amino acids with others that compliment the orthogonal purine analogs of AdoMet. Of course, a myriad of other possible mutations may work as well, and all would be within the scope of the present invention. In addition, from sequence alignments and crystal structures of methyltransferases, it is known that they have a common catalytic domain structure (70); so this approach is not limited to M. HhaI and COMT, but should be equally applicable to other methyl transferases.

After a methyltransferase mutant is identified which accepts an orthogonal inhibitor, radiolabeled AdoMet can then be synthesized which contains a C-14 labeled methyl group attached to the sulfur atom of AdoMet. When this radiolabeled analog is added to cells expressing one mutant methyltransferase, the direct substrates (e.g., protein or DNA, or polyamines) of all methyltransferases in the sample will be specifically radiolabeled with the $C^{14}$ methyl group.

But when this is done in the presence of the orthogonal inhibitor, the specific substrates for the methyltransferase of interest will be less labeled in comparison to the sample not containing the inhibitor; preferably, they will not be substantially labeled, and most preferably, will not be labeled at all. In this way, or through the use of other methods described herein for the study of the kinases, direct substrates of methyltransferases can be identified which are important in cancer, embryonic development, chemotaxis of polymorphonuclear leukocytes, or in neurological disorders. In addition, the methods of the present invention can then be used to determining whether compounds can be identified that modulate the activity of the enzyme. The several other aspects of the present invention, although perhaps not described here, could also be applied to the methyl transferases, and also to other multi-substrate enzymes.

The forgoing discussion of the application of the present invention to the methyl transferases is not intended to limit the scope of the present invention, but to illustrate of the applicability of the present invention to multi-substrate enzymes other than the protein kinases. As will be appreciated by those in the art, the present invention could be applied similarly to other multi-substrate enzymes using similar approaches.

Terms

As is generally the case in biotechnology, the description of the present invention herein has required the use of a substantial number of terms of art. Although it is not practical to do so exhaustively, definitions for some of these terms are provided here for ease of reference. Definitions for other terms also appear elsewhere herein, and those are not repeated here. It is important to note that it is not intended that the terms defined here or elsewhere herein be given a meaning other than that which those skilled in the art would understand them to have when used in the field, and it is therefore urged that other sources also be consulted in interpreting the meaning of these terms and those defined elsewhere herein. However, the definitions provided here and elsewhere herein should always be considered in determining the intended scope and meaning of the defined terms.

The term "orthogonal" is used here to mean a compound that is similar, structurally and/or geometrically, to the natural substrate for a given enzyme, or to an inhibitor of the wild-type form of the enzyme, but has differences in chemical structure which make that compound less able to bind to the wild-type form of the enzyme than is the natural substrate. By "natural" substrate Applicant means that substrate which is utilized by the wild-type form of that enzyme. The orthogonal inhibitors of the present invention may be referred to in different ways herein; for example, sometimes they are referred to as "modified substrates" or "modified inhibitors" or "analogs" or "derivatives" just as "substrates" or "inhibitors" and perhaps by other terms as well. However, in each instance, the same meaning is intended. Of course, the meaning of "orthogonal" and its synonyms are further explained in the descriptions of the invention provided above.

The putative orthogonal substrates and inhibitors of the embodiments of the invention described herein were made by adding bulky substituents to an atom on the natural substrate or known kinase inhibitor, respectively. However, the present invention is not so limited. For example, it is possible to make an orthogonal substrate that is smaller than a known inhibitor or the natural substrate, e.g., by preparing an analog that is missing one or more atoms or substituents that are present in the natural substrate. With such putative orthogonal substrates or inhibitors, one could mutate the enzyme to contain one or more amino acids having more bulky side chains than those found in the wild-type amino acid sequence, so that when the orthogonal substrate or inhibitor binds, those more bulky amino acid side chains fill or partially fill the extra space created by the missing atoms or substituents. In this way, it would be expected that the mutant would bind to and/or be inhibited by the orthogonal substrate or inhibitor, but would not substantially utilize the normal substrate, because the added bulky amino acids present a steric hindrance to its binding. Such an approach would allow for highly selective control of the resulting mutant.

It is important to keep in mind that even though the substrates and inhibitors of the examples herein are of the non-competitive type, this should not be viewed as a limitation of the scope of the present invention. Many different types of enzyme substrates and inhibitors are known, e.g., competitive, non-competitive, uncompetitive, "suicide" inhibitors, etc. Competitive inhibitors compete with a substrate for its binding site; but since the inhibitor cannot participate in the catalytic reaction which that enzyme carries out, it slows down catalysis. Non-competitive inhibitors bind to the active site, but then become covalently or ionically bound to the protein structure of the enzyme, such that they cannot come off. Thus, they inhibit catalysis by taking molecules of enzyme out of the reaction altogether. More detailed descriptions of these and other competitive mechanisms can be found in a variety of sources (e.g., (72)). By applying the understanding of the art regarding such mechanisms to the design of inhibitors of the present invention, all such types of inhibitors could be made.

For example, an analog which can bind, but not react, would provide a competitive inhibition, and an analog which becomes covalently attached to the enzyme upon binding, would be a non-competitive inhibitor, i.e., a poison. All such types of inhibitors are within the scope of the present invention.

The term "homologous to" has been used to describe how information about how to modify one enzyme can be deduced from information regarding the three-dimensional structure of other, related enzymes. As those in the field well know, a part of one enzyme which is "homologous" to part of a second enzyme has a protein sequence which is related to that of the second enzyme. This relationship is that they have a number of amino acids in the same relative location to one another. For example, the imaginary sequence Asp-Met-Phe-Arg-Asp-Lys-Glu (SEQ ID NO: 15) and the imaginary sequence Asp Met-Ile-Arg-Glu-Lys-Asp (SEQ ID NO: 16) have four amino acids in the same relative location, and three which are different, and they would be said to have homologous sequences. Note that the three amino acids that are different between the chains are "conservative" differences, in that the substitutions in the second sequence relative to the first are with amino acids that have similar functionalities on their side chains. For example, Glu and Arg both have aliphatic side chains terminated in carboxylic acid groups, and both Phe and Ile are hydrophobic. Although this is often the case with homologous protein sequences, it need not be the case, and these two imaginary sequences would still be considered homologous even if the differences were not conservative.

Whether a particular sequence or domain is homologous to another cannot be stated with any particularity, e.g., by using percentages, as there is no such absolute yardstick; one must leave it to the art to define which sequences are and are not considered "homologous." Reference (71) gives a good overview of which domains of the known kinases are considered by the art to be "homologous" In addition, although the art may not generally agree, it is intended here that sequences that are identical to one another also be considered to be "homologous" to one another.

The term "domain" is also one well known in the art, and it refers to a region in a protein which has been identified as having a particular functionality. For example, the three domains in protein kinases have been discussed elsewhere herein, and their functional roles have been discussed. Often, as is the case with the kinases, different enzymes of the same family will have the same number of domains with each serving the same function, and they are often (but probably not always) arranged in the same order along the protein sequence. Interestingly, as is the case for the kinases, one enzyme may have a different length of protein sequence between its domains than does another. However, since the domains of two related enzymes are generally (but probably not always) homologous to one another, this does not generally hamper the identification of corresponding domains.

In describing the broader aspects of the present invention, the term "multi-substrate" is used. This is intended to mean enzymes which bind two or more substrates. Those multi-substrate enzymes of most interest here are those which catalytically attach at least part of one substrate to at least one other substrate. The kinases and the transferases are but two families of such multi-substrate enzymes, and those of skill in the art will readily recognize that there are other such enzymes and enzyme families.

The term "recognize" is sometimes used here to describe the ability of a substrate to specifically bind to the active site on an enzyme. This simply refers to the fact that an enzyme's substrate (or sometimes substrate derivatives or even completely different compounds that mimic the substrate) can contact and bind to the enzyme's active site, but other compounds will not. This concept is well known in the art. Enzymologists often say that the enzyme has an affinity for its substrate, or that the substrate has an affinity for the enzyme. They also say that an enzyme has "substrate specificity" These all really describe the same phenomenon.

A related term is the term "bind." An inhibitor generally binds, or sticks to, an active site through one or more hydrophobic, hydrophilic, hydrogen, and/or ionic bonds, or, in the case of non-competitive inhibitors, through covalent bonds.

Although the complex understanding in the art regarding inhibitor binding and the reasons for inhibition may be of interest, such an understanding is not essential to understanding the present invention. It is sufficient to simply note that binding by an inhibitor causes inhibition of the catalytic reaction.

The terms "mutant" and "engineered form" when used to describe the enzymes of the present invention, simply mean that they have sequences that have a different amino acid at one or more position when compared to the sequence of the wild-type enzyme. In describing such mutants, two letters separated by a number indicate the amino acid mutations made. The letters are single-letter amino acid codes, and the numbers are the amino acid residue positions in the intact, wild-type enzyme. For example, GST XD4 (SEQ ID NO: 3) is a fusion protein containing a fragment, XD4, that has the same sequence as a specific part of the wild-type v-Src. In the designation GST-XD4 (V323A, I338A) (SEQ ID NO: 12), the valine in the sequence of v-Src fragment XD4 that represents position 323 in the complete wild type v-Src sequence has been replaced by alanine, and the isoleucine in the XD4 fragment that represents position 338 in the complete wild type v-Src sequence has also been replaced with alanine.

As described in the examples below, using the present invention Applicant has designed, made and demonstrated the utility of a v-Src kinase which shows high specificity for a synthetic inhibitor while maintaining its wild-type specificity for tyrosine containing peptides and proteins, thus satisfying Applicant's initial research goals. By exploiting the highly conserved nature of the ATP binding site across the kinase superfamily and the availability of structural information from other protein kinases, Applicant was able to engineer novel inhibition specificity for v-Src without any detailed structural information about v-Src itself. That Applicant used an unrelated kinase as a blueprint for designing orthogonal ATP analogs to tag the direct cellular substrates of v-src and have prepared inhibitors from like origins demonstrates that this approach should work for other kinases as well.

EXAMPLES

The following examples are provided to describe and illustrate the present invention. As such, they should not be construed to limit the scope of the invention. Those in the art will well appreciate that many other embodiments also fall within the scope of the invention, as it is described hereinabove and in the claims.

Example 1

Synthesis of ATP Analogs

Figure 2:
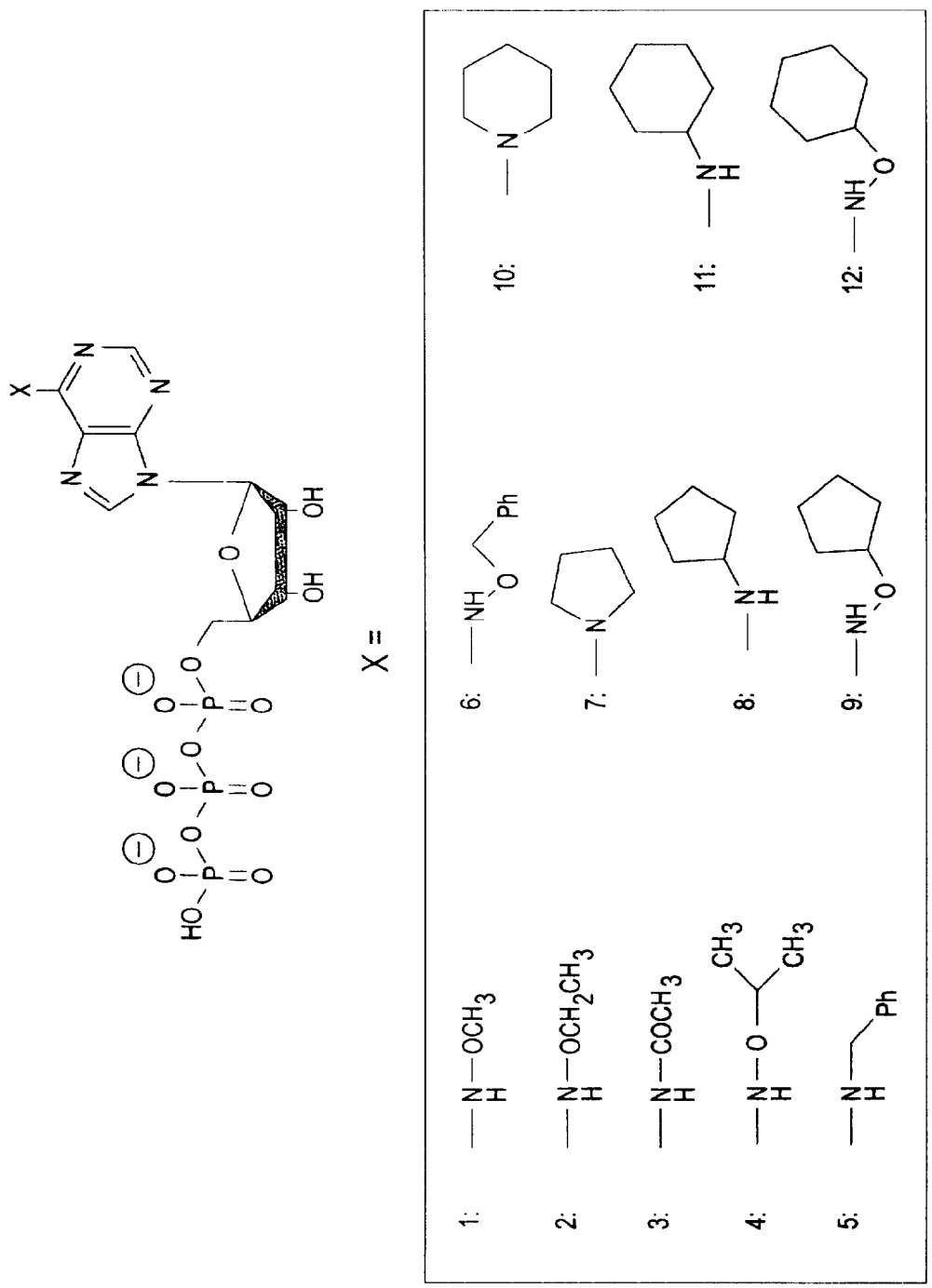
FIG. 2 is a schematic representation of adenosine triphosphate (ATP), with an "X" bound to the $N^6$ position; and in the box below, schematic representations are provided for the twelve side chains that take the place of "X" in each of the orthogonal ATP analogs described in the examples (which are always referred to by the numbers 1–12 set forth in bold typeface)

Twelve different orthogonal ATP analogs were synthesized. FIG. 2 is a schematic representation of their structure. The figure shows adenosine triphosphate (ATP), with an "X" bound to the 6 position; and in the box below, schematic representations are provided for the twelve side chains that take the place of "X" in each of the orthogonal ATP analogs described in the examples (which are always referred to by the numbers 1–12 set forth in bold typeface). Those analogs are:

1. $N^6$(methoxy)ATP
2. $N^6$(ethoxy)ATP
3. $N^6$(acetyl)ATP
4. $N^6$(i-propoxy)ATP
5. $N^6$(benzyl)ATP I
6. $N^6$(benzyloxy)ATP
7. $N^6$(pyrolidino)ATP
8. $N^6$(cyclopentyl)ATP
9. $N^6$(cyclopentyloxy)ATP
10. $N^6$(pipperidino)ATP
11. $N^6$(cyclohexyl)ATP
12. $N^6$(cyclohexyloxy)ATP Analogs 1, 2, 4, 6, 9 & 12 were synthesized via Dimroth rearrangement of the corresponding $N^1$ alkoxy adenine derivatives in four steps starting from adenosine, according to the procedure of Fuji et al. (43). Analog 5 was synthesized similarly via Dimroth rearrangement of $N^1$ benzyladenosine (44). Analog 3 was prepared via in situ protection of the adenosine hydroxyl groups as trimethylsilyl ethers and subsequent treatment with acetyl chloride, according to McLaughlin et al. (45). Analogs 7, 8, 10 & 11 were synthesized via treatment of 6-chloropurine riboside (Aldrich) with pyrrolidine, cyclopentylamine, piperidine & cyclohexylamine, respectively (46).

Triphosphate synthesis was carried out according to the method of Ludwig (47) with the exception of the preparation of pyrophosphate. Accordingly, bis-tri-N-butyl ammonium pyrophosphate was prepared by mixing 1 equivalent of pyrophosphoric acid with two equivalents of tributyl amine in a (1:1) water: ethanol mixture until a homogenous solution was obtained. Solvent was removed under vacuum to dryness and the pyrophosphate was stored over $P_2O_5$ overnight.

All non-radioactive nucleotides were characterized by $^1$H-NMR, mass spectral analysis and strong anion exchange (SAX) HPLC (Rainin #83-E03-ETI).

[γ-$^{32}$P] N$^6$(cyclopentyl)ATP was synthesized according the method of Hecht & Kozarich, (48). The radiolabeled analog was purified by DEAE (A-25) Sephadex (Pharmacia) column chromatography and the triphosphate was identified by co-injection of the radiolabeled material with an authentic sample of N$^6$(cyclopentyl) ATP on an SAX-anion exchange HPLC column (Rainin) (linear gradient of 5–750 mM ammonium phosphate pH 3.9 in 10 minutes at 0.5 ml/min). The chemical yield of the reaction varied from 70–80%.

Example 2
Screening of Nucleotide Analogs

To identify compounds that would not be accepted as substrates by any existing cellular kinases (53), Applicant screened a panel of synthetic A*TP analogs in a murine lymphocyte lysate (CF) rich in protein tyrosine kinases (13).

The assays were performed using spleenocytes (8–30 week old male and female C57/B6 mice from the Princeton University Animal Facility) which were isolated and washed in RPMI-1640 medium containing 5% Bovine Calf Serum (BCS), 1% Hepes and DNaseI (1 μg/ml). Red cells were lysed at 4° C. by treatment with 17 mM Tris ammonium chloride (pH 7.2). The cells were hypotonically lysed on ice for ten minutes in 1 mM Hepes (pH 7.4), 5 mM $MgCl_2$, leupeptin (10 μg/ml), aprotinin (10 μg/ml) and 100 μM PMSF according to the method of Fukazawa et al. (51). After vortexing and centrifugation at 500×g, the supernatant was collected. Cells were stored at 4° C. for twenty minutes to attenuate the basal protein phosphorylation level, after which the buffer was adjusted to 20 mM Hepes (pH 7.4), 10 mM $MgCl_2$ and 1 mM NaF. Sodium vanadate (100 μM) was then added to inhibit the activity of phosphotyrosine phosphatases.

Each nucleotide triphosphate was added to a final concentration of 100 μM to 5×10$^6$ cell equivalents and incubated at 37° C. for five minutes after which 4×Laemmli gel loading buffer was added to the cell lysate to quench the reaction. Proteins were separated by 12.5% SDS-PAGE and transferred to Protran BA85 (Schleicher-Schuell). The blot was probed with the anti-phosphotyrosine monoclonal antibody 4G10 (Upstate Biotechnology) and the bound antibody was detected via enhanced chemiluminescence (Pierce) following treatment with HRP-coupled goat anti-mouse antibody (VWR catalog # 710133) according to the manufacturer's instructions.

Figure 3:
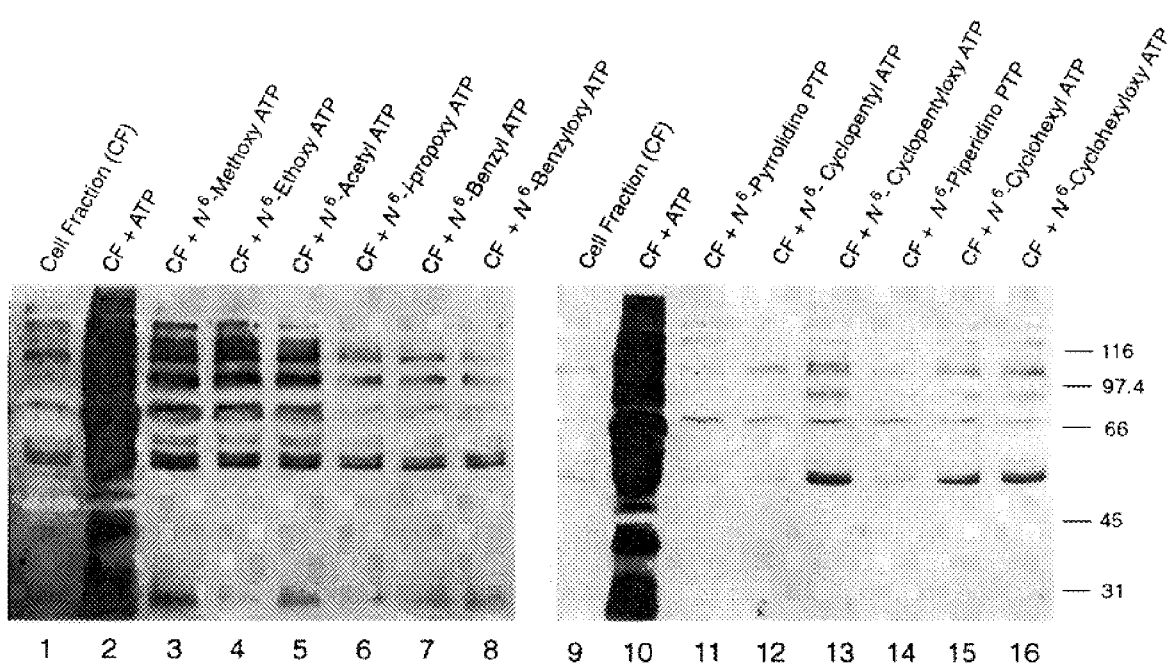
FIG. 3 is an anti-phosphotyrosine immunoblot showing the level of protein tyrosine phosphorylation following treatment of a murine lymphocyte cell lysate with ATP or one of the ATP analogs (A*TPs)

The results are shown in FIG. 3, which is an anti-phosphotyrosine protein immunoblot showing the level of protein tyrosine phosphorylation following treatment of a murine lymphocyte cell lysate (CF) with 100 μM of ATP or A*TPs (1–12). The cell lysate used includes the tyrosine kinases Src, Fyn, Lck, Lyn, Yes, Fgr, Hck, Zap, Syk, Btk, Blk, and other tyrosine kinases present in B and T lymphocytes, macrophages, and follicular dendritic cells (13). Molecular size standards (in kilodaltons) are indicated. The A*TPs containing the smallest N$^6$ substituents, (1) (methoxy), (2) (ethoxy), and (3) (acetyl) showed some ability to serve as cellular tyrosine kinase substrates (FIG. 3, lanes 3–5). The A*TPs with sterically demanding N$^6$ substituents, (4) (i-propoxy), (5) (benzyl), and (6) (benzyloxy), and all analogs containing cyclic aliphatic substituents (7–12) showed little or no protein phosphorylation (FIG. 3, lanes 6–8, 11–16).

To test for possible metathesis of orthogonal A*TPs (7–12) with cellular ADP to give A*DP and ATP, Applicant added 1mM ADP to cell lysate kinase reactions identical to those shown in FIG. 3; (data not shown); the pattern of phosphoproteins was the same, indicating that no significant metathesis of A*TP occurs in a complete cell lysate system.

Based upon these results, it appears that analogs (7–12) are "dead substrates" for wild type tyrosine kinases, i.e., the wild-type substrates do not substantially, or at all, accept these as phosphate donor substrate. These analogs thus were chosen as the most preferred targets for reengineering the nucleotide binding site of v-Src.

Example 3
Designing the Mutant v-Src

No crystal structures of any tyrosine kinases in an active conformation have been solved to date although several structures of inactive kinases have been solved (54,55). However, two crystal structures of catalytically active ser/thr kinases have been solved (56,57). There is a high degree of functional homology between the ser/thr and the tyrosine kinase catalytic domains as shown by affinity labeling of the identical catalytically active lysine residue in both kinase families (K72 in cAMP dependent kinase (PKA), K295 in v-Src) (58). Inspection of the PKA (56) and cyclin dependent kinase-2 (CDK2)-cyclinA (57) crystal structures revealed two amino acid side chains within a 4 Å sphere of the N$^6$ amino group of bound ATP: V104/M120 (PKA) and V64/F80 (CDK2) (60).

FIG. 4 shows a close-up view of the ATP binding site in cAMP dependent protein kinase (PKA), which is bound to ATP. Three residues within a 4 Å sphere of the N$^6$ amine of ATP (Val104, Met120 and Glu121) and the catalytically essential lysine residue (Lys72) are shown in ball-and-stick representation. The remainder of the protein is shown in ribbon format. This figure was created by feeding the output of Molscript into the Raster three-dimensional rendering program (68,69). Note that in the model, the side chain of Glu121 is pointed away from the adenine ring binding region, and therefore Glu121 was not a candidate for alteration.

The sequence alignment of the ATP binding regions of PKA (SEQ ID NO: 1), CDK2 (SEQ ID NO: 2), and v-Src (SEQ ID NO: 3) are shown below. The residues shown in bold correspond to the amino acids with side chains in a 5 Å sphere of the N$^6$ amino group of kinase bound ATP.

| Subdomain | IV | V | |
|---|---|---|---|
| PKA (SEQ ID NO: 1) | (99) | NFPFLVKLEFSFKDNSNLYMVMEYVPG | (125) |
| CDK2 (SEQ ID NO: 2) | (59) | NHPNIVKLLDVIHTENKLYLVFEFLHQ | (85) |
| v-Src (SEQ ID NO: 3) | (318) | RHEKLVQLYAVVSE-EPIYIVIEYMSK | (343) |

Based on the functional similarity between the above-described kinases, Applicant decided to mutate positions V323 and I338 in the v-Src catalytic domain, which correspond to V104/M120 in PKA & V64/F80 in CDK2. By mutating these residues to alanine, Applicant hoped to create an additional "pocket" in the nucleotide binding site of v-Src to allow binding of one of the preferred orthogonal A*TPs (4–12).

Example 4
Mutant Synthesis, Expression and Purification

The mutant (V323A, I338A) (SEQ ID NO: 12) was made as described below. Both the wild-type (SEQ ID NO: 3) and the double alanine mutant of the v-Src catalytic domain, (the XD4 fragment) were made as glutathione S-transferase (GST) fusion proteins (GST-XD4) (61,62). These were made in *E. coli*, which is a good expression host because it lacks any endogenous tyrosine kinases, as described in the following Example. Applicant used the XD4 fragment of v-Src because it contains an intact SH1 catalytic domain but lacks the non-catalytic regulatory SH3 and SH2 domains, and exhibits higher specific activity than full-length v-Src.

Overlap extension PCR was used to make GST-XD4 (V323A, I338A) (SEQ ID NO: 12) (49). Pfu polymerase (Stratagene) was used in the PCR reactions according to the manufacturer's protocol. Six synthetic oligonucleotides were used:

SEQ ID NO: 4 (5'-TTTGGATCCATGGGGAGTAGCAAGAGCAAG)
SEQ ID NO: 5 (5'-TTTGAATTCCTACTCAGCGACCTCCAACAC)
SEQ ID NO: 6 (5'-TGAGAAGCTGGCTCAACTGTACGCAG)
SEQ ID NO: 7 (5'-CTGCGTACAGTTGAGCCAGCTTCTCA)
SEQ ID NO: 8 (5'-CTACATCGTCGCTGAGTACATGAG)
SEQ ID NO: 9 (5'-CTCATGTACTCAGCGACGATGTAG)

Primer SEQ ID NO: 4 contains a BamH1 site and primer SEQ ID NO: 5 contains an EcoR1 site (shown in italics). Primers SEQ ID NO: 6 and SEQ ID NO: 7 contain the nucleotide sequence changes to introduce the V323A mutation (nucleotides encoding mutations are shown in bold). Primers SEQ ID NO: 8 and SEQ ID NO: 9 contain the I338A mismatch.

The XD4 gene from YEp51-XD4 plasmid (a gift of B. Cochran at Tufts Medical School) was amplified with primers SEQ ID NO: 4 and SEQ ID NO: 5. The PCR product was digested with BamH1 and EcoR1 and ligated into BamH1 and EcoR1 digested pGEX-KT and then transformed into the *E. coli* strain DH5α.

The GST-XD4 (V323A) (SEQ ID NO: 13) was constructed using primer SEQ ID NO: 4, SEQ ID NO: 5, SEQ ID NO: 6 and SEQ ID NO: 7 with the GST-XD4 plasmid as the template. The PCR product from the two step procedure was digested with BamH1 and EcoR1, ligated into BamH1 and EcoR1-digested pGEX-KT, and transformed into DH5α *E. coli* cells. GST-XD4 (V323A, I338A) (SEQ ID NO: 12) was made in the same manner using primers SEQ ID NO: 8 & SEQ ID NO: 9 with GST-XD4 (V323A) (SEQ ID NO: 13) as the template.

Expression and purification of the GST fusion kinases were carried out in *E. coli* strain DH5α as described by Xu et al. (50), with the exception that the cells were stored at 4° C. overnight prior to centrifugation and lysis by French press (overnight storage is essential for producing highly active kinases).

Expression of 6-His-XD4 and 6-His-XD4 (V323A, I338A) in Sf9 insect cells was accomplished using the Life Technologies BAC-to-BAC system. Briefly, the 6-His-XD4 and 6-His-XD4 (V323A, I338A) genes were generated by PCR using the corresponding pGEX vectors as templates with primers SEQ ID NO: 4 and SEQ ID NO: 5 followed by digestion with BamH1 and EcoR1. The resulting PCR fragment was cloned into pFASTBAC which had been digested with BamH1 and EcoR1. Transformation of HB1 OBAC cells and subsequent transfection of Sf9 cells with the Bacmid containing XD4 or XD4 (V323A, I338A) were carried out as suggested by the manufacturer.

In an alternate procedure performed herein, transfection of v-src or v-src (I338G) mutant kinase was performed by cloning the v-src gene from the pGEX-v-Src vector (4) into the pBabe vector (5) which contains the LTR promotor for high level of expression in NIH3T3 cells. The pBabe v-Src (I338G) plasmid was transfected into viral packaging cell line BOSC23 (6) and viral particles harvested after two days as described (6). NIH3T3 cells were infected as described (7) with these viral particles and stable transfectants were selected in puromycin containing media as described (5). Stable transfectants were maintained in media containing puromycin to ensure no loss of expression of v-Src.

Figure 1:
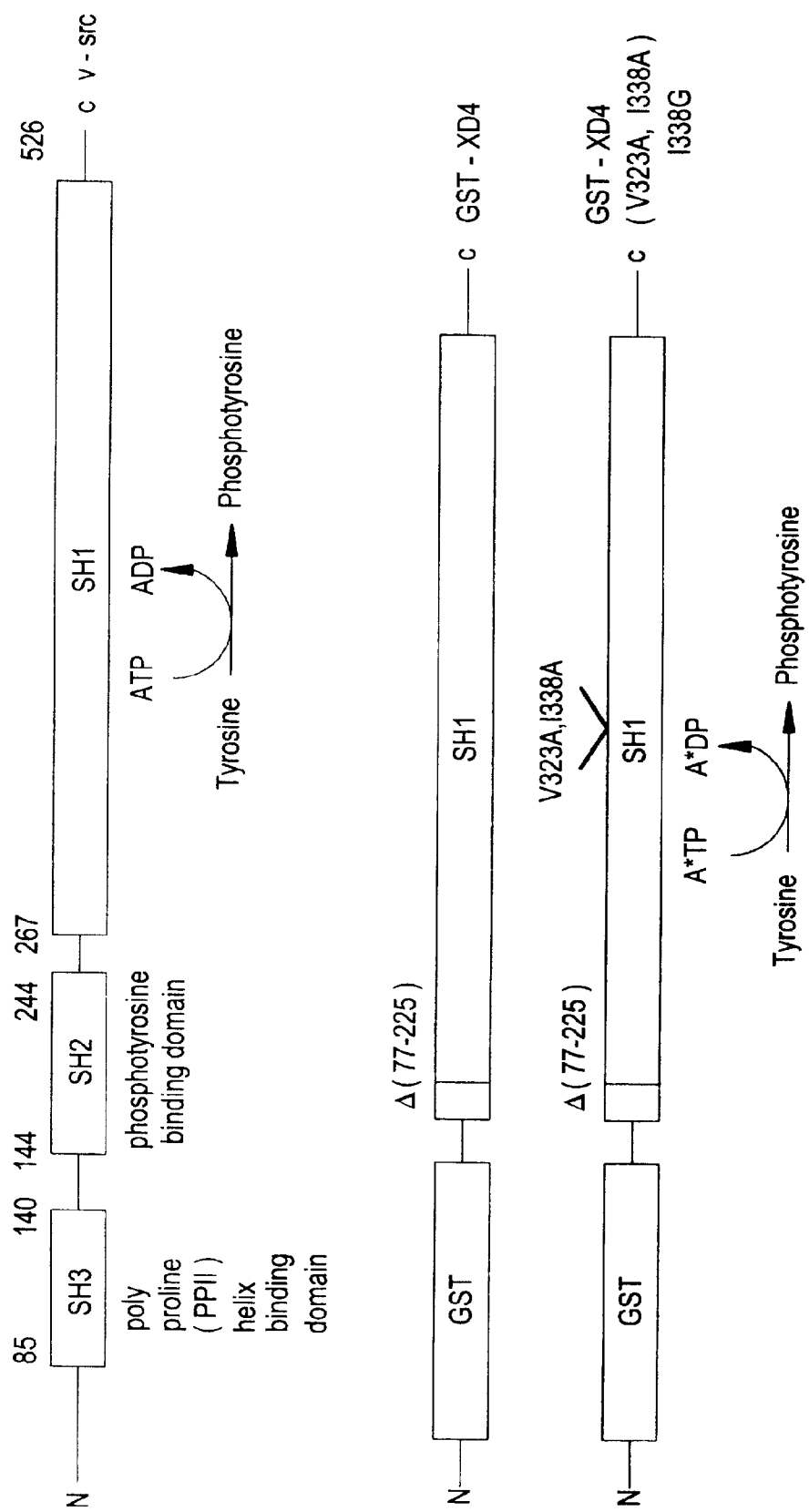
FIG. 1 is a schematic representation of the protein domain structures of v-Src, of XD4 (which has a deletion of residues 77–225), of the glutathione S-transferase (GST)-XD4 fusion protein, and of the GST-XD4 fusion protein double mutant (V323A, I338A) (SEQ ID NO: 12)

The final results are shown in FIG. 1, which is a diagram showing the domain structure of v-Src including the Src-homology 3, 2, and 1 (SH3, SH2 & SH1) domains, with the domain boundaries indicated by the amino acid residue numbers listed above each boxed domain. The domain structure of XD4 is also represented, which contains a deletion of residues 77–225 (Δ77–225). Domain organizations of the glutathione S-transferase (GST) fusion with XD4 (numbering from v-Src), and the doubly mutated GST-XD4 (representing both V323A, I338A and I338G) are also shown schematically.

Example 5
Testing the Mutant v-Src For Ability to Bind Orthogonal ATP Analogs Applicant next evaluated the ability of the $N^6$ substituted ATP analogs (1–12) to differentially inhibit wild-type and mutant kinase phosphorylation of RR-Src with [$\gamma$-$^{32}$P] ATP, which is a measure of their ability to bind to the respective ATP binding sites. Assays were carried out in triplicate at 37° C. in a final volume of 30 μL buffered at pH 8.0 containing 50 mM Tris, 10 mM $MgCl_2$, 1.6 mM glutathione, 1 mg/ml BSA, 1 mM RR-Src peptide with either GST-XD4 (100 nM) or GST XD4 (V323A, I338A) (100 nM) and 10 μM [$\gamma$-$^{32}$P]ATP (1000 cpm/pmol) (Dupont-NEN). Cold ATP or A*TP analogs (100 μM) (1–12) were added prior to addition of the kinase. After thirty minutes the reactions were quenched by spotting 25 μl of the reaction volume onto p81 phosphocellulose disks (Whattman) and these were immersed in 250 ml of 10% acetic acid for at least thirty minutes followed by washing and scintillation counting according to standard methods (52).

The results are shown in FIG. 6. Relative inhibition of GST-XD4 (SEQ ID NO: 3) is shown by solid bars, and relative inhibition by GST-XD4 (V323A, I338A) (SEQ ID NO: 12) is represented by the diagonal filled bars. Percent inhibition ($1-v_1/v_0$) is reported as a ratio of $v_1$ (cpm in the presence of 100 μM of the indicated triphosphate and 10 μM [$\gamma$-$^{32}$P] ATP (1000 cpm/pmol)/$v_o$ (cpm in the presence of 10 μM [$\gamma$-$^{32}$P] ATP (1000 cpm/pmol) alone background cpm due to non-specific 10 μM [$\gamma$-$^{32}$P] ATP binding to the phosphocellulose disks (<0.1% of total input counts). Error bars represent the S.D. determined from four separate experiments with three replicates.

The wild-type kinase GST-XD4 (SEQ ID NO: 3) displays poor binding affinity for most A*TP analogs (FIG. 6, solid bars) as expected from the lymphocyte kinase assay (FIG. 3). In contrast, the doubly mutated GST-XD4 (V323A, I338A) (SEQ ID NO: 12) shows excellent inhibition by more sterically demanding $N^6$ substituted ATP analogs (FIG. 6, shaded bars). Most significantly, the GST-XD4 (V323A, I338A) (SEQ ID NO: 12) mutant is inhibited from phosphorylating RR-Src with $^{32}$P-ATP by ATP analogs (5), (8), (9) and (11) almost as well as the wild-type kinase, GST- XD4 (SEQ ID NO: 3), is inhibited from phosphorylating RR-Src with $^{32}$P-ATP by its natural substrate ATP. Applicant has confirmed that GST-XD4 (V323A, I338A) (SEQ ID NO: 12) and the full length GST-v-Src (V323A, I338A) display the same inhibition pattern with A*TPs (1–12) (data not shown).

Four of the nine "dead" substrates identified in the screen of wild-type kinase specificity (FIG. 3) bind well to the mutant kinase. This high success rate in identifying new substrates for a mutant v-Src which are not accepted by wild-type kinases suggests that Applicant has identified a key feature of the v-Src nucleotide binding site, namely the residues which make a close fit around the $N^6$ amino group of ATP. It is worth noting that Applicant is not aware of any wild-type protein kinases which contain an alanine at the position corresponding to I338 in v-Src (position 120 in PKA). If a sterically demanding amino acid side chain at this position also plays a critical role in determining the specificity of other kinases, it should well be possible to engineer them to accept orthogonal substrates using an approach very similar to the one described here, and such engineered kinases would be well within the scope of the present invention.

Example 6

Determining Catalytic Efficiency of Mutant v-Src with the Most Preferred Orthogonal ATP Analog Applicant chose to test the ability of $N^6$(cyclopentyl)ATP, (8), to serve as a catalytically competent substrate of both wild-type GST-XD4 (SEQ ID NO: 3) and the GST-XD4 (V323A, I338A) (SEQ ID NO: 12) mutant over the other three ATP analogs (5), (9) and (11) because analog (8) exhibited a slightly lower level of phosphorylation with wild-type kinases (FIG. 3, lane 12).

ATP and $N^6$(cyclopentyl)ATP dependent RR-Src phosphorylation (1 mM) by GST-XD4 (V323.A, I338A) and GST-XD4 were carried out at low substrate conversion (<5%) in triplicate. Kinetic constants were determined by analysis of Lineweaver-Burk plots of the rate data (64). Assays were carried out in triplicate at 37° C. in a final volume of 30 μl buffered at pH 8.0 containing 50 mM Tris, 10 mM MgCl$_2$, 1.6 mM glutathione, 1 mg/ml BSA, 1 mM RR-Src peptide with either GST-XD4 (SEQ ID NO: 3) (100 nM) or GST-XD4 (V323A, I338A) (SEQ ID NO: 12) (100 nM) and 10 μM [γ-$^{32}$P] ATP (1000 cpm/pmol) or [γ-$^{32}$P] $N^6$(cyclopentyl)ATP (5000 cpm/pmol) as indicated.

not a significant substrate for the wild-type kinase. In contrast, GST-XD4 (V323A, I338A) (SEQ ID NO: 12) displayed Michaelis-Menten kinetics with the orthogonal A*TP, [γ-$^{32}$P] $N^6$(cyclopentyl)ATP. The $K_M$ of the mutant (SEQ ID NO: 12) for the orthogonal substrate is quite close to the $K_M$ of GST-XD4 (SEQ ID NO: 3) for ATP. On the other hand, the mutant (SEQ ID NO: 12) has a $K_M$ for ATP which is more than 10-fold higher than the $K_M$ of GST-XD4 (SEQ ID NO: 3) for ATP.

The parameter used to rank catalysts for competing substrates is the ratio of the turnover number to the Michaelis-Menten constant, $k_{cat}/K_M$ (the "specificity constant") (Fersht, (1985) Enzyme structure and mechanism, W. H. Freeman). The $k_{cat}/K_M$ of the engineered mutant GST-XD4 (V323A, I338A) (SEQ ID NO: 12) with the orthogonal substrate [γ-$^{32}$P] $N^6$(cyclopentyl)ATP is only 50-fold lower than the $k_{cat}/K_M$ value of the wild-type kinase (SEQ ID NO: 3) with its natural substrate, ATP. This catalytic efficiency with the orthogonal A*TP substrate, coupled with the mutant kinase's lower catalytic efficiency with ATP when compared to the wild-type, satisfy two of the design criteria discussed above.

It is even more significant that the new substrate, [γ-$^{32}$P] $N^6$(cyclopentyl)ATP, is not substantially utilized by wild-type GST-XD4 (SEQ ID NO: 3), as demonstrated by the apparent complete inability of GST-XD4 (SEQ ID NO: 3) to use this analog as a phosphodonor for autophosphorylation; this is illustrated in FIG. 5C, lane 3. FIG. 5C is an autoradiogram showing [γ-$^{32}$P]ATP dependent autophosphorylation of GST-XD4 (SEQ ID NO: 3), lane 1, or GST-XD4 (V323A, I338A) (SEQ ID NO: 12), lane 2; and [γ-$^{32}$P] $N^6$(cyclopentyl)ATP dependent phosphorylation of GST-XD4 (SEQ ID NO: 3), lane 3, or GST-XD4 (V323A, I338A) (SEQ ID NO: 12) phosphorylation, lane 4. Note that in contrast to GST-XD4 (SEQ ID NO: 3), the engineered kinase (SEQ ID NO: 12) is efficiently autophosphorylated with [γ-$^{32}$P] $N^6$(cyclopentyl)ATP (FIG. 5C, lane 4).

Example 7

Confirming Retention of Protein Substrate Specificity

As shown in Table 2 below, Applicant has found that the wild-type GST-XD4 kinase (SEQ ID NO: 3) phosphorylated a well characterized peptide substrate of v-Src, RR-Src, with kinetics consistent with literature reports (Czernilofsky et al.

TABLE 1

Kinetics for Phosphate Donor Substrates

| | GST-XD4 | | | GST-XD4 (V323A, I338A) | | |
|---|---|---|---|---|---|---|
| Nucleotide | $k_{cat}$ (min$^{-1}$) | $K_M$ (μM) | $k_{cat}/K_M$ (min$^{-1}$M$^{-1}$) | $k_{cat}$ (min$^{-1}$) | $K_M$ (μM) | $k_{cat}/K_M$ (min$^{-1}$M$^{-1}$) |
| ATP | 2 ± 0.5 | 12 ± 3 | 1.6 × 10$^5$ | 0.8 ± 0.2 | 150 ± 20 | 5.3 × 10$^3$ |
| $N^6$(cp)ATP | 2000 ($K_i$) | | | 0.05 ± 0.02 | 15 ± 3 | 3.3 × 10$^3$ |

As shown in Table 1 above, the wild-type kinase GST-XD4 (SEQ ID NO: 3) did not substantially phosphorylate the RR-Src peptide with [γ-$^{32}$P] $N^6$(cyclopentyl)ATP, confirming Applicant's previous observations that this analog is (1980) Nature 287:198–200). This indicates that the sequence engineering had not substantially affected the catalytic activity of the enzyme with respect to its protein substrates.

TABLE 2

Kinetics for Protein Substrate RR-Src

|  | GST-XD4 | GST-XD4 (V323A, I338A) |
|---|---|---|
| Nucleotide | $K_M$ (μM) | $K_M$ (μM) |
| ATP | 2.6 ± 0.9 | 3.1 ± 0.9 |
| $N^6$(cp)ATP |  | 2.1 ± 0.9 |

Assays of GST-XD4 (SEQ ID NO: 3) and GST-XD4 (V323A, I338A) (SEQ ID NO: 12) phosphorylation of RR-Src were carried out in triplicate at 37° C. in a final volume of 30 μl buffered at pH 8.0 containing 50 mM Tris, 10 MM $MgCl_2$, 1.6 mM glutathione, 1 mg/ml BSA, 1 mM RR-Src peptide with either GST-XD4 (SEQ ID NO: 3) (100 nM) or GST-XD4 (V323A, I338A) (SEQ ID NO: 12) (100 nM) and 10 μM [γ-$^{32}$P] ATP (1000 cpm/pmol).

To determine whether the alanine mutations have any effect on the protein substrate specificity, Applicant measured the $K_M$ of both the wild-type and the mutant fusion proteins for the RR-Src peptide. At saturating concentrations of [γ-$^{32}$P]ATP the wild-type and the mutant display essentially the same $K_M$ for RR-Src, 2.6±0.9 mM and 3.1±0.9 mM, respectively (63). In addition, the $K_M$ of the mutant for the protein substrate in the presence of saturating amounts of the orthogonal substrate was also essentially the same, 2.1±0.9 mM. These findings suggest that the alanine mutations in the ATP binding pocket, which is proximal to the adjacent phospho-acceptor binding site, do not affect the protein target specificity.

In support of this, the engineered kinase phosphorylates the same broad set of proteins that are phosphorylated by wild-type XD4 when each is expressed in Sf9 insect cells. This is shown in the FIG. 5A, which shows an anti-phosphotyrosine protein blot of cell lysates (10⁸ cell equivalents/lane) from Sf9 insect cells expressing 6-His-XD4, lane 2 or 6-His-XD4 (V323A, I338A), lane 3. These blots were carried out following lysis of $10^6$ cells in a buffer containing 0.1% Triton x-100, 50 mM Tris (pH 8.0) using a procedure similar to that of the-blots of Example 2.

The Sf9 insect cell system is a good host for expressing small amounts of tyrosine kinases because these cells contain most of the same machinery necessary to carry out post-translational modifications to proteins resulting in kinases which are more similar in activity to those found in mammalian cells. Furthermore, uninfected Sf9 cells lack endogenous tyrosine kinase activity, as shown in FIG. 5A, lane 1, and thus the phosphotyrosine containing proteins in lanes 2 and 3 of FIG. 5A are substrates of the expressed 6-His-XD4 or mutant 6-His-XD4 kinases. Applicant attributes the small differences in phosphorylation level of particular proteins to the lower catalytic activity of the mutant XD4 (V323A, I338A) compared to the wild-type kinase.

Taken together, these data show that the peptide specificity of the engineered kinase is virtually identical to that of wild-type v-Src.

Example 8
Confirmation that the Engineered Kinase Accepts the Preferred Orthogonal Substrate, but the Wild-Type Kinase Does Not Substantially Accept it The ultimate goal of this work is to use mutant kinases specific for synthetic substrate analogs to tag the direct protein substrates in whole cells or cell lysates. For this it is preferable that no wild-type kinase, including ser/thr specific kinases (which carry out the bulk of cellular phosphorylation, as only 0.03% of all phosphoamino acids are tyrosine) (65), substantially accept the synthetic substrate. To establish that [γ-$^{32}$P] $N^6$(cyclopentyl)ATP is essentially a "dead substrate" for all wild-type cellular kinases, in vitro kinase reactions with [γ-$^{32}$P] ATP or [γ-$^{32}$P] $N^6$(cyclopentyl)ATP were performed with murine lymphocyte lysates.

These assays were performed in a manner similar to the procedure set forth in Example 2, with the exception of the use of radiolabeled [γ-$^{32}$P] ATP or [γ-$^{32}$P] $N^6$(cyclopentyl) ATP (5000 cpm/pmole) added to a final concentration of 100 μM with 5×10⁶ cell equivalents and incubated at 37° C. for ten minutes, after which 4×Laemmli gel loading buffer was added to the cell lysate to quench the reaction. Proteins were separated by 12.5% SDS-PAGE. The gel was soaked in 10% acetic acid, 10% isopropanol for one hour after which it was dried in a gel dryer and exposed to Biomax MS film (Kodak) for one hour.

The results are shown in FIG. 5B, which is an autoradiogram showing the level of phosphorylation in hypotonically lysed murine lymphocytes with [γ-$^{32}$P] ATP, lane 1 or [γ-$^{32}$P] $N^6$(cyclopentyl)ATP, lane 2. There are no radiolabeled phosphoproteins in the cell lysate following addition of [γ-$^{32}$P] $N^6$(cyclopentyl)ATP, confirming the true orthogonal nature of $N^6$(cyclopentyl)ATP with respect to all wild type protein kinases. The same result was found when in vitro kinase reactions with [γ-$^{32}$P] ATP or [γ-$^{32}$P] $N^6$(cyclopentyl)ATP and NIH3T3 cell lysates were used instead of freshly isolated murine lymphocytes (not shown).

In principle, the ability to follow one protein kinase's activity in the presence of all other cellular kinases would allow for the identification of the direct kinase targets in a particular cell type. To accomplish this Applicant is currently using membrane permeabilization (66) and a cell permeable form of A*TP to introduce [γ-$^{32}$P] A*TP into cells (67).

Example 9
Construction and Analysis of Single Mutation v-Src Mutants

In order to determine whether a single mutation might be sufficient to allow $N^6$(cyclopentyl)ATP to be efficiently used as a substrate, three additional v-Src derived mutants were prepared, using methods comparable to those of Example 4. However, these had only single mutations, at position 338. These were again expressed as GST-XD4 fusion proteins. These mutants, GST-XD4 (I338A) (SEQ ID NO: 11), GST-XD4 (I338S) (SEQ ID NO: 14) and GST-XD4 (I338G) (SEQ ID NO: 10), were then tested as described in Example 8.

The results are shown in FIG. 7. The gel lanes shown on the top left of FIG. 7 show that the mutant with alanine at the 338 position (SEQ ID NO: 11) was able to utilize the natural substrate, ATP, more readily than the mutant with serine (SEQ ID NO: 14) at that same position. The gel lanes shown on the bottom left of FIG. 7 show that the mutant with alanine in position 338 (SEQ ID NO: 11) is also better able to use ATP as a substrate than is the mutant with glycine (SEQ ID NO: 10) at that position.

The panels on the right side of FIG. 7 tell an even more interesting story. From the top right panel, it is clear that the mutant with serine at position 338 (SEQ ID NO: 14) is not able to utilize $N^6$(cyclopentyl)ATP nearly as well as is the mutant with alanine (SEQ ID NO: 11) at that position. However, the bottom panel shows that the mutant with glycine at position 338 (SEQ ID NO: 10) is better able to use $N^6$(cyclopentyl)ATP as substrate than is the mutant with alanine (SEQ ID NO: 11) at that position.

These results are most promising. It appears that a single mutation is enough to allow the use of this orthogonal substrate. Notably, the mutant with glycine at position 338 (SEQ ID NO: 10) appears to be the best engineered v-Src mutant that Applicant has produced to date. Moreover, it is quite surprising that a glycine substitution would work here.

Generally, glycine substitution is usually not expected to work in such situations, because it introduces too much flexibility into the enzyme structure, and thus detrimentally affects the desired outcome.

Example 11

Identifying the Substrates of v-Src

A schematic representation of an experimental approach to identifying v-Src substrates is shown in FIG. 8. The engineered v-Src, such as GST-XD4 (V323A, I338A) (SEQ ID NO: 12), is added to cell extracts or permiablized cells, along with a radiolabeled orthogonal substrate, such as [$\gamma$-$^{32}$P] N$^6$(cyclopentyl)ATP. Typically, this would be done in triplicate. After incubation, the cells would be lysed (if not already lysed), and the resulting samples would be separated by polyacrylamide gel electrophoresis.

A western blot taken from the gel and labeled with anti-phosphotyrosine would show all phosphorylated proteins in the sample; and an autoradiogram of the gel would reveal which of those were phosphorylated by v-Src.

Example 12

Synthesis of Inhibitors

The pyrazolopyrimadine backbone for the first six inhibitors is shown in FIG. 11A. Synthesis of 4-amino-1-tert-butyl-3-phenylpyrazolo [3,4-d]pyrimidine, having a phenyl group in the "R" position, compound 1 (which is the same structure as PP1, shown on FIG. 10, but without the para-methyl group on the phenyl ring) was carried out according to the method of Hanefeld et al. (76). Compounds (2–6) (FIG. 11), having cyclobutoyl, cyclopentoyl, cyclohexoyl, benzoyl, and 2-furoyl substituents at the "R" position, respectively, were synthesized by treatment of (1) with cyclobutoyl chloride, cyclopentoyl chloride, cyclohexoyl chloride, benzoyl chloride, or furoyl chloride, respectively in dry pyridine for one hour at room temperature. The structures of each of the substituents are shown in FIG. 11B. Purification by silica gel chromatography afforded pure products in 6–84% yield. Compounds (1–6) were characterized by $^1$H-NMR and mass spectral methods.

Example 13

Screening of Inhibitors which are Orthogonal to Wild-type Kinases

To identify compounds that would not inhibit any existing cellular kinases, Applicant screened the panel of synthetic pyrazolo pyramidine analogs (1–6) against two closely related purified tyrosine kinases, v-Src and Fyn, in a peptide phosphorylation assay using [$\gamma$-$^{32}$P] ATP as the radiolabel tracer of kinase activity, as described in Shah et al. (79).

The results showed that each of the compounds (2–6) had $IC_{50}$ values of over 400 $\mu$M for inhibition of Src and compounds (3) and (5) showed at over 400 $\mu$M $IC_{50}$ values for inhibition of wild-type Fyn (SEQ ID NO: 19), indicating that these analogs (2) and (5) are orthogonal to (do not inhibit) these representative wild-type kinases.

Examples 14–16

Deconvoluting protein kinase signaling pathways using conventional genetic and biochemical approaches has been difficult due to the overwhelming number of closely related kinases. If cell permeable inhibitors of each individual kinase could be designed, the role of each protein kinase could be systematically assessed.

Results: Applicant has devised an approach combining chemistry and genetics to develop the first uniquely specific cell permeable inhibitor of the oncogenic protein tyrosine kinase, v-Src. A functionally silent active site mutation was made in v-Src in order to distinguish it from all other cellular kinases. A tight binding ($IC_5$=430 nM) cell permeable inhibitor of this mutant kinase was designed and synthesized which does not inhibit wild-type kinases. In vitro and whole cell assays established the unique specificity of the mutant v-Src/inhibitor pair. This inhibitor reverses the transforming effects of cellular expression of the engineered v-Src, but does not disrupt wild type v-Src mediated cellular transformation. These cell lines differ only by a single amino acid in a single protein kinase, establishing that dramatic changes in cellular signaling can be directly attributed to specific inhibition of the engineered kinase. The generality of this method was tested by engineering another tyrosine kinase, Fyn (SEQ ID NO: 20), to contain the corresponding silent mutation. The same compound was found to be a potent inhibitor ($IC_{50}$=830 nM) of this mutant kinase as well, confirming the generality of the strategy toward making allele specific inhibitors of multiple tyrosine kinases.

Conclusions: Allele specific cell permeable inhibitors of individual Src family kinases can be rapidly developed using a combined chemical and genetic approach.

Treatment of mutant v-Src transformed NIH3T3 fibroblasts with a uniquely specific v-Src reverts the morphological hallmarks of transformation. The inhibitor exhibits no effect on cells transformed by the wild-type v-Src allele strongly suggesting that the phenotype induced by inhibitor treatment is a result of a single inhibitory event.

The ability to rapidly generate kinase specific inhibitors in a generalizable way will be useful for deconvolution of kinase mediated cellular pathways and for validating novel kinases as good targets for drug discovery both in vitro and in vivo.

As stated earlier, a combined chemical and genetic strategy has been devised which allows for the generation of "chemical sensitive" mutant kinases which are uniquely inhibited by a rationally designed small molecule inhibitor. Applicant's approach involves engineering a unique pocket in the active site of the kinase of interest with a functionally silent mutation. A specific inhibitor of the engineered kinase is then synthesized by derivatizing a known kinase inhibitor with a bulky group designed to fit the novel active site pocket. The bulky group kills the potency of the inhibitor for wild type kinases. Successful complementary design, therefore, leads to favorable binding interactions that are only possible in the engineered kinase/inhibitor complex. Transfection of cells with the gene encoding the engineered kinase generates a cell in which only one kinase can be blocked by the designed inhibitor (see FIG. 14).

Importantly, since the mutant kinase serves the same function as the wild-type kinase, an inhibitor of the mutant will affect cell signaling in the same manner as a selective inhibitor of the wild-type kinase in non-transfected cells. The ability to observe the phenotype of cells after selective inhibition of any protein kinase provides a rapid method for determining the unique roles of individual kinases in signal transduction cascades.

Applicant has targeted the src family protein tyrosine kinases for specific inhibitor design because of their ubiquitous importance in mediating cell function. Despite intense investigation, the roles of individual src family members have been difficult to assess because of cellular co-localization and their high sequence identities. Although some potent inhibitors of Src family kinases are known, no molecules which can effectively discriminate (twenty-fold selectivity for one src family member) between these closely related enzymes have been identified.

Two functionally important src kinases, v-Src and Fyn, were chosen as the primary targets of Applicant's mutant kinase/inhibitor pair design. Src kinase has emerged as a leading drug target because of its implication in the oncogenesis of breast, lung, and colon cancers. Although v-Src is the prototype for oncogenic tyrosine kinases, no small molecule inhibitors which are highly selective for this kinase have been discovered. Fyn is an Src family tyrosine kinase which is important in T cell receptor mediated lymphocyte activation. Src and Fyn share a similar domain structure and have approximately 85% amino acid identity in their catalytic domains. The close structural relationship of the Src family members provides the ideal test of Applicant's ability to engineer enzyme/inhibitor specificity between highly homologous kinases. If one can discriminate between these closely related Src members using a cell permeable inhibitor, it is likely that specificity for members of other protein kinase families can also be achieved using a similar approach.

Results and Discussion

Enzyme Engineering

From Applicant's previous efforts to engineer kinases with novel ATP specificity, Applicant identified a functionally conserved residue in the ATP binding pocket of v-Src (Ile338) which could be mutated to glycine without altering the phosphoacceptor specificity or biological function of the kinase. The space creating mutation causes only a modest drop in $k_{cat}$ with a modest increase in the $K_M$ for ATP and no quantitative change in the level of fibroblast transformation (Shah, unpublished results). The biological substrates of the mutant v-Src are unchanged and I338G v-Src (SEQ ID NO: 10) carries out the same biological functions as wild type v-Src (SEQ ID NO: 3). All crystal structures of ATP bound protein kinases have revealed a close contact interaction between the residue corresponding to 338 (Src numbering) and ATP. Analysis of protein kinase sequence alignments confirmed that residue 338 contains a bulky side chain (usually Thr, Ile, Leu, Met, or Phe) in all known eukaryotic protein kinases. Thus, a glycine mutation at the 338 position should create a novel pocket that is not present in any wild type kinase. Due to the expanded ATP binding site, the glycine mutant kinases should accept bulky inhibitors that could not bind wild type kinases. Using standard methods Applicant cloned, expressed and purified the glutathione-S-transferase (GST) fusion protein of the wild type (WT) (SEQ ID NO: 3) and I338G v-Src (SEQ ID NO: 10) catalytic domains as described previously. WT Fyn (SEQ ID NO: 19), T339G Fyn (SEQ ID NO: 20) (Src numbering), and WT Abl were also expressed and purified as GST fusion proteins.

Inhibitor Design and Synthesis

To test Applicant's basic design strategy Applicant screened the WT and I338G v-Src SH1 domains against a previously synthesized panel of $N^6$ substituted adenosine molecules for selective inhibition of I338G v-Src over WT v-Src. Because adenosine is only a moderate inhibitor of src family tyrosine kinases, Applicant did not expect to discover a potent inhibitor of the engineered kinase. As expected, all of the $N^6$ adenosine analogues inhibited I338G v-Src more potently than WT v-Src (data not shown). The most potent inhibitor found in this screen was $N^6$ cyclopentyloxyadenosine ((1), FIG. 15A) with an $IC_{50}$ of 1 mM for I338G v-Src. Subsequent experiments to test for selectivity demonstrated that $N^6$ cyclopentyloxyadenosine showed no detectable in vitro inhibition of WT v-Src (SEQ ID NO: 3) or Fyn (SEQ ID NO: 19) at concentrations up to 400 mM. This first screen encouraged Applicant to pursue the strategy of developing novel inhibitors of I338G v-Src since Applicant's design had allowed Applicant to readily over come selectivity barriers which are major problems in conventional inhibitor discovery.

As inhibitors, adenosine analogues are not ideal because of the many cellular functions performed by adenosine as well as the large number of cellular proteins which bind adenosine. $N^6$ adenosine analogues have been shown to act as adenosine receptor agonists and antagonists, and one can imagine $N^6$ adenosine analogues acting as substrates for nucleoside kinases. For these reasons Applicant turned to a class of known tyrosine kinase inhibitors that are not direct analogues of biologically known molecules. Applicant's design strategy called for a core structure which exhibits potent inhibition of multiple wild type kinases and is easily synthesized. Also, the binding orientation of the molecule in the enzyme active site must be known or readily predictable. In addition, the molecule must bind in a manner in which the site pointing toward Ile338 can be easily modified. As Applicant's core inhibitor structure 4-amino-1-tert-butyl-3-phenylpyrazolo(3,4-d)pyrimidine was chosen ((2), FIG. 15B). This molecule is a derivative of 4-amino-1-tert-butyl-3-(p-methylphenyl)pyrazolo(3,4-d)pyrimidine (PP1) which was reported by Hanke and co-workers as a potent src family kinase inhibitor. Based on the co-crystal structure of the src family kinase, Hck, bound to the general kinase inhibitor, quercetin ((5), FIG. 16), Applicant postulated that (2) binds to src family kinases in a conformation similar to that of ATP. The predicted binding orientation of (2) in Hck is shown in an overlay with the known Hck co-crystal structures of AMP PNP (2) and quercetin (FIG. 16B). In this conformation the easily derivatizable $N^4$ position of (2) corresponds to the $N^6$ of ATP (close contact with residue 338, FIG. 16C) and the tert-butyl moiety roughly corresponds to the ribose ring of ATP. Applicant further hypothesized that in this orientation, the C-3 phenyl ring of (2) could bind in a pocket that surrounds the N-7 of ATP as seen in the Hck/quercetin co-crystal structure. This analysis lead Applicant to synthesize a small panel of $N^4$ derivatized analogues of (2) (FIG. 2).

Identification of a Uniquely Selective Inhibitor

The panel of pyrazolo(3,4-d)pyrimidines was screened against WT (SEQ ID NO: 3) and I338G (SEQ ID NO: 10) v-Src kinases (see FIG. 13). All of the analogues are better inhibitors of the engineered v-Src (SEQ ID NO: 10) as compared to wild type (SEQ ID NO: 3), confirming Applicant's prediction of the binding orientation of (2) in the kinase active site. Any derivatization of (2) at the $N^4$ position destroys the inhibitory activity against WT v-Src (SEQ ID NO: 3) (no detectable inhibition at the limit of solubility, 300 mM). All ten analogues demonstrated measurable inhibition of I338G v-Src (SEQ ID NO: 10) and several of the compounds have $IC_{50}$ in the low mM range. The $N^4$ (p-tert-butyl)benzoyl analogue (3 g) is the most potent inhibitor of I338G v-Src (SEQ ID NO: 10) in the panel ($IC_{50}$=430 nm). This molecule shows no inhibition of WT v-Src (SEQ ID NO: 3) at 300 mM suggesting that (3 g) is at least a thousand-fold better inhibitor of the mutant v-Src (SEQ ID NO: 10) as compared to wild type (SEQ ID NO: 3). The large size of the derivatization needed to achieve sub-micromolar potency for the I338G v-Src active site (SEQ ID NO: 10) was rather unexpected. Applicant removed only four carbon atoms from the ATP binding site and derivatized the parent molecule with eleven carbon atoms. This discrepancy may be due to an imperfection in Applicant's binding prediction. Also the Ile to Gly mutation may confer greater flexibility to the enzyme active site allowing the mutant kinase (SEQ ID NO: 10) to accept a larger inhibitor analogue than predicted. To confirm that (3 g) does inhibit I338G v-src (SEQ ID NO: 10) at the ATP binding site Applicant investigated its kinetics of inhibition at various ATP concentrations. Lineweaver-Burk analysis confirmed that (3 g) does inhibit I338G v-Src (SEQ ID NO: 10) competitively with respect to ATP with an inhibitory constant ($K_i$) of approximately 400 nM (data not shown).

The panel of inhibitor analogues was next screened against WT Fyn (SEQ ID NO: 19) to investigate their potential to cross react with this kinase. WT Fyn (SEQ ID NO: 19) was chosen as the "worst case" control of wild type kinases because the published parent molecule, PP1 and (2) are highly potent (low nM) Fyn inhibitors. Many of the ten synthetic analogues did not display high selectivity for the target kinase (see FIG. 13). The N-acyl analogues with saturated ring systems (3a–3c) effectively inhibit wild type Fyn (SEQ ID NO: 19). The N-methylene compounds (4b, 4d, 4e) are sufficiently orthogonal to WT Fyn (SEQ ID NO: 19) but show only poor to moderate inhibition of the engineered v-Src (SEQ ID NO: 10). Importantly, (3 g), the most potent inhibitor of the mutant v-Src (SEQ ID NO: 10) inhibited WT Fyn (SEQ ID NO: 19) very weakly ($IC_{50}$=300 mM). Thus, (3 g) inhibits the engineered v-Src (SEQ ID NO: 10) over 700 times more effectively than WT Fyn (SEQ ID NO: 19), which is likely to be the wild type cellular kinase which is most capable of binding the molecule.

Applicant also tested whether other non-src family kinases were fortuitously inhibited by (3 g) in vitro. The serine/threonine kinases, PKCδ and PKA (SEQ ID NO: 1), were not detectably inhibited at concentrations up to 300 mM. Likewise, (3 g) exhibited only weak inhibition ($IC_{50}$>300 mM) of the Abl tyrosine kinase. Therefore (3 g) satisfied all of Applicant's initial design requirements for potent selective inhibition of one engineered kinase.

Selectivity in Whole Cells

To further demonstrate that (3 g) does not inhibit wild type tyrosine kinases Applicant investigated the effects of (3 g) treatment on the B cell receptor (BCR) mediated phosphorylation cascade. Src family (Fyn, Lyn, Lck, Blk) and non-src family tyrosine kinases (Btk, Syk) are known to be activated upon BCR cross-linking. Due to the amplifying nature of the BCR mediated cascade, inhibition of any of these kinases would dramatically alter the distribution and intensity of post-activation cellular phosphotyrosine. Because (3 g) was designed to be sterically incompatible with the active sites of wild type kinases, it should not disrupt tyrosine phosphorylation dependent signaling in wild type B cells. FIG. 17 (lane 3) demonstrates that 100 μM (3 g) treatment of antigen receptor cross linked murine B cells has no effect on the phosphotyrosine pattern of B cell stimulation (compare to lane 2). The signal intensities of all the major bands are unchanged and only slight depletion of some minor bands is detectable, confirming that (3 g) does not appreciably inhibit the panel of tyrosine kinases that are activated by BCR cross linking. Treatment of B cells with 100 μM (2), however, causes a significant reduction in tyrosine phosphorylation (FIG. 17, lane 4) that is consistent with its potent inhibition of wild type src family kinases.

Selective inhibition of I338G v-Src in NIH3T3 Cells

In order to use Applicant's selective inhibitor to study a Src mediated pathway Applicant retrovirally introduced both WT and I338G v-Src into NIH3T3 fibroblasts. These cells acquire a transformed phenotype which is dependent on v-Src expression. Applicant sought to show that (3 g) could selectively disturb the Src dependent signal transduction pathway of I338G v-Src transformed cells while not affecting WT transformed cells. Treatment of WT v-Src infected cells (100 μM (3 g)) causes no loss of tyrosine phosphorylation compared to control DMSO treated lanes (FIG. 18), demonstrating that the designed inhibitor does not inhibit WT v-Src or any of the other tyrosine kinases that are activated by v-Src mediated cellular transformation. Equivalent treatment of I338G v-Src transformed cells gives rise to a dramatic diminution in the tyrosine phosphorylation of the putative v-Src substrate, p36, as well as a moderate overall decrease in the cellular level of phosphotyrosine. Previously, it has been shown that treatment of v-Src transformed cells with general tyrosine kinase inhibitors causes a reduction in the tyrosine phosphorylation of a 36 kDa protein. It is thought that p36 is associated with a specific phosphotyrosine phosphatase, possibly explaining its rapid dephosphorylation in inhibitor treated cells. The (3 g) $IC_{50}$ for p36 phosphotyrosine signal in I338G v-Src expressing cells (50 mM) is roughly one-hundred times the in vitro value (data not shown). This is presumably due to the fact that the inhibitor must compete with millimolar concentrations of ATP for the kinase active site in the cellular experiments.

Selective Inhibition of I338G Mutant v-Src Reverses Transformed Cell Morphology v-Src activity is required for Rous sarcoma virus transformation of mammalian cells. Treatment of the I338G v-Src expressing NIH3T3 cells with 100 μM (3 g) caused dramatic changes in cell morphology which are consistent with the reversal of transformation (FIG. 19). The mutant cells that were treated with inhibitor (3 g) appeared flat and did not exhibit growth characteristics of transformed cells (i.e., the ability to grow on top of one another). Under identical conditions, WT v-Src infected cells demonstrated the prototypical rounded morphology and overlapping growth patterns of transformed cells.

To further demonstrate the selective reversal of cell morphology Applicant used fluorescence microscopy to view (3 g) treated cells after staining the cellular polymerized actin with phalloidin-FITC (FIG. 19). Non-transformed NIH-3T3 cells show long actin spindles that form across the cells. v-Src transformed cells (both WT and I338G) appear rounded with no discernible pattern of actin formation. In agreement with the light microscopy data, inhibitor treated WT v-Src expressing cells appear indistinguishable from untreated WT cells. However, (3 g) treated I338G v-Src expressing cells have defined polymerized actin strings, strongly resembling the actin formations of non-transformed NIH-3T3 fibroblasts. These inhibitor treated cells have an exaggerated flattened morphology and show peripheral act-instaining that is not present in the non-transformed NIH3T3 cells. This data shows that (3 g) can uniquely induce morphological changes in cells which are engineered to contain a single amino acid change in the kinase of interest. This is the first demonstration that a small molecule inhibitor selective for a tyrosine kinase oncogene product can revert the morphological changes associated with cellular transformation. Previous examples of morphological reversion of transformation by herbimycin A (and other benzoquinone ansamycins) have recently been shown to operate via a mechanism unrelated to kinase inhibition consisting of heat shock protein (hsp90) mediated targeting of the oncogenic tyrosine kinase to the proteasome.

Generalization to other Kinases

The advantage of using mutagenesis to provide a unique molecular difference between the enzyme of interest and all others is that, due to the conserved kinase fold, the approach should be extendible across the kinase superfamily. Almost all known protein kinases contain a bulky side chain at the position corresponding to residue 338 of v-Src. Therefore a space creating mutation at this position should render multiple kinases susceptible to selective inhibition. To test this Applicant measured the inhibition of the analogues against T339G Fyn (SEQ ID NO: 20) (Table 1). There exists a striking similarity in the structure activity relationships of the analogues for I338G v-Src (SEQ ID NO: 10) and T339G Fyn (SEQ ID NO: 20). In agreement with the data for I338G v-Src (SEQ ID NO: 10), (3 g) was the most potent inhibitor analogue against T339G Fyn (SEQ ID NO: 20), exhibiting an $IC_{50}$ of 830 nM. This corresponds to greater than 300 fold selectivity for T339G Fyn (SEQ ID NO: 20) over WT Fyn (SEQ ID NO: 19). The implication of this data is that multiple tyrosine kinases can be systematically engineered to preferentially accept one inhibitor analogue without the need to screen large libraries of putative inhibitors.

Conclusion

In this report Applicant describes a novel approach to selective protein kinase inhibition through the complementary engineering of chemical sensitive kinases and rationally designed inhibitors. Applicant demonstrates that high selectivity for the target kinase can be achieved in whole cells, and that active site inhibition of an oncogenic tyrosine kinase can be sufficient for the disruption of a transformed cell morphology. Because the approach is easily generalized, it should have far reaching applications in deconvoluting signal transduction pathways as well as validation of kinases as targets for drug design. The pace of effective drug discovery is limited by the identification and validation of important drug targets. This is not a trivial problem in a milieu of 2000 homologous proteins. The use of chemical sensitive mutants of protein kinases expands the capability to probe the cellular and physiological effects of pharmacological kinase inhibition. Since transfected cell lines and even "knock-in" mice can now be generated rapidly, Applicant's approach should greatly expedite the process of testing the effects of selective inhibition of a given kinase in a whole cell or animal model. As more inhibitor-bound protein kinase crystal structures become available, this strategy will allow for the systematic investigation of the effects of time and dose dependent inhibition of any given kinase in the scope of an entire signal transduction cascade.

Materials and Methods

Chemical Synthesis

All starting materials and synthetic reagents were purchased from Aldrich unless otherwise noted. All compounds were characterized by $^1$H NMR and high resolution mass spectrometry. 4-amino-1-tert-butyl-3-phenylpyrazolo(3,4-d) pyrimidine (2) was synthesized according to Hanefeld et al. (85).

General procedure for $N^4$ acylation of (2) (3a–3 g). To a solution of (2) (100 mg) dissolved in 2 ml pyridine was added 10 equivalents of the desired acyl chloride at 0° C. The reaction mixture was allowed to warm to room temperature and stirred for twelve hours. The reaction was quenched by the addition of 25 ml water. The resulting mixture was extracted with $Et_2O$ and the combined $Et_2O$ extracts were washed with 1 N HCl and 5% $NaHCO_3$. The $Et_2O$ layer was dried over $MgSO_4$ and evaporated. The residue was purified by flash chromatography on 25 grams silica gel by elution with 1:1 $Et_2O$/hexanes to yield pure (3a–3g).

4-cyclobutylamido-1-tert-butyl-3-phenylpyrazolo-[3,4-d] pyrimidine (3a): yield 0.0116 grams (16%), white powder: HRMS (EI) molecular ion calcd. for $C_{70}H_{23}N_5O$ 349.19049, found 349.18762; $^1$H NMR (300 MHz, $CDCl_3$, ppm) d 1.86 (9H, s), 1.89–2.27 (6H, m), 3.58 (1H, m), 7.26–7.67 (5H, m), 8.69 (1H, s).

4-cyclopentylamido-1tert-butyl-3-phenylpyrazolo[3,4-d] pyrimidine (3b): yield 0.0456 grams (68%), white powder: HRMS (EI) molecular ion calcd. for $C_{21}H_{25}N_{25}N_5O$ 363.20615, found 363.20398; $^1$H NMR (270 MHz, $CDCl_3$, ppm) d 1.41–1.91 (8H, m), 1.87 (9H, s), 2.97 (1H, m), 7.51–7.67(5H, m), 8.70 (1H, s).

4-cyclohexylamido-1-tert-butyl-3-phenylpyrazolo[3,4-d] pyrimidine (3c): yield 0.0575 grams (84%), white powder; HRMS (EI) molecular ion calcd. for $C_{22}H_{27}N_5O$; $^1$H NMR (270 MHz, $CDCl_3$, ppm) d 1.21–1.93 (10H, m), 1.86 (9H, s), 2.43 (1H, m), 7.51–7.67 (5H, m), 8.70 (1H, s).

4-2'-furylamido-1-tert-butyl-3-phenylpyrazolo[3,4-d] pyrimidine (3d) yield 0.0342 grams (60%) white powder; HRMS (EI) molecular ion calcd. for $C_{20}H_{19}N_5O_2$ 361.15407, found:361.15254; $^1$H NMR (270 MHz, $CDCl_3$, ppm) d 1.87 (911, s), 6.52 (1H, d), 7.23 (1H, d), 7.43–7.53 (5H, m), 7.95(1H, s), 8.59(1H, s).

4-benzamido-1-tert-butyl-3-phenylpyrazolo[3,4-d] pyrmidine (3e): yield 0.1309 grams (56%) white powder, HRMS (EI) molecular ion calcd. for $C_{23}H_{21}N_5O$ 371.17933, found 371.17324; $^1$H NMR(279 MHz, $CDCl_3$, ppm) d 1.41–1.91 (8H, m), 7.22–8.11 (10H, m), 8.48 (1H, s).

4-(p-methyl)benzamido-1-tert-butyl-3-phenylpyrazolo [3,4-d]pyrimidine (3f): yield 0.0751 grams (33%), white powder; HRMS (EI) molecular ion calcd. for $C_{23}H_{23}N_5O$ 385.19499, found 385.18751; $^1$H NMR (270 MHz, $CDCl_3$, ppm) d 1.88 (911, s), 2.42 (3H, s), 7.19 (2H, d), 7.41–8.11 (7H, m), 8.49 (1H, s,).

4-(p-tert-butyl)benzamido-1-tert-butyl-3-phenylpyrazolo [3,4-d]pyrimidine (3g): yield 0.1050 grams (42%), white powder; HRMS (EI) molecular ion calcd. for $C_{26}H_{29}N_5O$ 427.23747, found 427.23474; $^1$H NMR (270 MHz, $CDCl_3$, ppm) d 1.35 (9H, s), 1.88 (9H, s), 7.38–7.99 (9H, m), 8.50 (1H, s).

General Procedure for the Reduction of $N^4$Acyl Compounds to $N^4$ Methylene Compounds (4b, 4d, 4e).

A round bottom flask was charged with 30 mg $LiAlH_4$. The flask was equipped with a pressure equalizing dropping funnel and flushed with dry argon. The $LiAlH_4$ was suspended in 3 ml THF over an ice bath. Approximately 100 mg of the corresponding $N^4$ acyl (2) analogue was dissolved in 5 ml THF and added dropwise to the suspension of $LiAlH_4$. The reaction mixture was stirred for thirty minutes on the ice bath and subsequently heated to reflux for thirty minutes. The reaction was quenched by the sequential, dropwise additions of 1 ml EtOAc, 1 ml water, and 1 ml 6 N NaOH. After stirring for five minutes, the reaction mixture was filtered through a celite pad, diluted with water and extracted with $Et_2O$. The $Et_2O$ extracts were combined, dried over $MgSO_4$, and evaporated. The residue was purified by flash chromatography on 10 g silica gel by elution with 4:1 hexanes/EtOAc.

4-cyclopentylmethylamino-1-tert-butyl-3-phenylpyrazolo[3,4-d]pyrimidine (4b): yield 0.0649 grams (75%), clear oil; HRMS (EI) molecular ion calcd. for $C_{21}H_{27}N_5$ 349.22691, found 349.22420; $^1$H NMR (270 MHz, $CDCl_3$, ppm) d 1.16–2.14 (9H, m), 1.84 (9H, s), 3.54 (2H, d), 5.51(1H, s), 7.46–7.67 (5H, m), 8.43 (1H, s).

4-2'-furylmethylamino-1-tert-butyl-3-phenylpyrazolol[3, 4-d]pyrimidine (4d): yield 0.0620 grams (66%), beige powder; HRMS (EI) molecular ion calcd. for $C_{20}H_{21}N_5O$ 347.17483, found 347.17330; $^1$H NMR (270 MHz, $CDCl_3$, ppm) d 1.83 (9H, s), 4.75 (2H, d), 5.64 (1H, s), 6.25 (2H, d), 7.34–7.63 (6H, m), 8.45 (1H, s).

4-benzylamino-1-tert-butyl-3-phenylpyrazolo[3,4-d] pyrimidine (4e): yield 0.0520 grams (54%), white powder; HRMS (EI) molecular ion calcd. for $C_{22}H_{23}N_5$ 357.19559, found 357.19303; $^1$H NMR (270 MHz, $CDCl_3$, ppm) d 1.82 (9H, s), 4.76 (2H, d), 5.63 (1H, s), 7.28–7.63 (10H, m), 8.44 (1H, s).

Protein Expression and Purification

Site directed mutagenesis and cloning of the genes for the glutathione-S-transferase fusion proteins of WT v-Src SH1 domain, I338G v-Src SH1, WT Fyn, T339G Fyn, and WT Ab1 into the pGEX-KT plasmid was carried out as described previously. These kinases were expressed in DH5α *E. Coli* and purified on immobilized glutathione beads (Sigma). PKA was purchased (Pierce) and used without further purification. PKCδ was expressed as the 6-His construct using the Bac-to-Bac (expression system (pFastBac B vector). PKCδ was purified using a QlAexpress Ni-NTA agarose column.

In vitro Kinase Inhibition Assay $IC_{50}$ for putative kinase inhibitors were determined by measuring the counts per minute (cpm) of [$^{32}$P] transferred to an optimized peptide substrate for src family kinases-IYGEFKKK (SEQ ID NO: 17). Various concentrations of inhibitor were incubated with 50 mM Tris (pH 8.0), 10 mM $MgCl_2$, 1.6 mM glutathione, 1 mg/ml BSA, 133 mM IYGEFKKK (SEQ ID NO: 17), 3.3% DMSO, 0.05 mM kinase and 11 nM (2 mCi) [γ-$^{32}$P]ATP (6000 Ci/mmol, NEN) in a total volume of 30 ml for thirty minutes. Reaction mixtures (25 ml) were spotted onto a phosphocellulose disk, immersed in 10% HOAc, and washed with 0.5% $H_3PO_4$. The transfer of [$^{32}$P] was measured by standard scintillation counting. $IC_{50}$ was defined to be the concentration of inhibitor at which the cpm was 50% of the control disk. When the $IC_{50}$ fell between two measured concentrations it was calculated based on the assumption of an inversely proportional relationship between inhibitor concentration and cpm between the two data points. Because the solubility limit of the inhibitor analogues in aqueous solutions is (300 μM, $IC_{50}$ values of 250 μM are approximate as full titrations to the upper limit of inhibition could not be tested). $IC_{50}$'s for non-src family kinases were measured equivalently with the following exceptions. Kemtide (Pierce, 133 mg/ml) was used as the substrate for PKA. An optimized AbI substrate, EAIYAAPFAKKK (SEQ ID NO: 18), 133 mg/ml) was used for Ab1 assays. PKC assays were performed in the presence of 17 ng/ml diacyl glycerol Sigma) and 17 ng/ml phosphatidyl serine (Sigma) with 170 ng/ml histone (Sigma) as the kinase substrate.

Murine B Cell Assay

Splenic lymphocytes were isolated from 6–20 week old Balb/c or C57/B6 mice. The cells were washed out of the spleen into RPMI media containing 1 mg/ml DNase I and the red blood cells were lysed in 17 mM tris-ammonium chloride (pH 7.2). Approximately 4×10$^6$ cells were incubated at 37° C. for thirty minutes with 100 μM of (3 g) or (2) in 1.1% DMSO. B cell stimulation was initiated by the addition of 2 mg of goat anti-mouse IgM (Jackson ImmunoResearch) and subsequent incubation for five minutes at 37° C. The cells were isolated by centrifugation (13,000 rpm, two minutes) and lysed (lysis buffer: 1% Triton x-100, 50 mM Tris (pH 7.4), 2 mM EDTA, 150 mM NaCl, 100 mM PMSF, 2 mM sodium orthovanadate, 10 mg/ml leupeptin, 10 mg/ml apoprotin). The cellular debris was then pelleted at 13,000 rpm for fifteen minutes. Cellular proteins were separated by 10% polyacrylamide gel electrophoresis and transferred to a nitrocellulose membrane by Western blotting. Phosphotyrosine containing proteins were visualized by immunoblotting with anti-phosphotyrosine antibody (Upstate Biotechnology).

Retroviral Infection of NIH3T3 Fibroblasts

Genes encoding WT and I338G v-Src were transfected into a packaging cell line and NIH3T3 fibroblasts were retrovirally infected using the pBabe retroviral vector and a puromycin (2.5 mg/ml) selectable marker as described (86). WT and I338G v-Src transformed cells were cultured in DMEM supplemented with 10% BCS containing 2.5 mg/ml puromycin.

Inhibition of v-Src in NIH3T3 Fibroblasts

Non-transformed NIH3T3 cells, WT v-Src transformed NIH3T3 cells, and I338G v-Src transformed NIH3T3 cells were incubated at 37° C. with 1.1% DMSO or 100 μM (3 g) in 1.1% DMSO. After twelve hours, the cells were washed with PBS and lysed (lysis buffer: 1% Triton x-100, 50 mM tris (pH 7.4), 2 mM EDTA, 150 mM NaCl, 100 mM phenylmethylsulphonyl fluoride, 2 mM sodium orthovanadate, 10 mg/ml leupeptin, 10 mg/ml apoprotin). The lysate was clarified by centrifugation at 13,000 rpm for fifteen minutes. Lysate protein concentrations were normalized and equal volumes of the lysate were resolved electrophoretically and analyzed for phosphotyrosine content as described above.

Microscopy

Non-transformed, WT v-Src transformed, and I338G v-Src transformed NIH-3T3 fibroblasts were grown in DMEM/10% BCS on tissue culture treated slides. v-Src expressing cells were treated with either 1.1% DMSO or 100 μM (3g) in 1.1% DMSO. After forty-eight hours cells were photographed at 400×magnification on an Nikon TMS light microscope. Immediately following light microscopy, the cells were fixed for twenty minutes in 3.7% formaldehyde/PBS and permeabilized for sixty seconds in 0.2% Triton x-100 in PBS. Permeabilized cells were incubated with 200 ng/ml phalloidin-FITC/PBS for twenty minutes. Slides were rinsed with PBS and polymerized actin was visualized by fluorescence microscopy at 600×magnification on a Zeiss fluorescence microscope.

Example 17

Confirming Retention of Protein Substrate Specificity and Biological Activity

This could be carried out as described in (86). Further, the stereo typed role of v-Src in the oncogenic transformation of NIH-3T3 cells can be determined by observing the morphological change in cells expressing v-Src. The NIH-3T3 cells expressing mutant I338G v-Src display the identical morphological features of cells expressing wild-type v-Src which are dramatically distinct from NIH-3T3 cells which do not express either v-Src kinase, confirming that the I338G mutation does not lead to any loss or gain of biological function of normal v-Src. Further, an assay for the ability of NIH-3T3 cells to grow without "contact inhibition" can be measured in a cell culture based assay containing agarose, a viscous growth medium. The wild-type v-Src and mutant v-Src expressing NIH3T3 cells display the exact same ability to form large growth colonies in this stereotyped assay as well, further confirming their identical functions (including substrate specificity, kinetics, cell distribution, etc.) in fibroblasts.

Example 18

Confirmation that the Orthogonal Inhibitor Does not Inhibit Wild-type Kinases in Cells which Express Multiple Tyrosine Kinases To confirm Applicant's initial assays regarding the orthogonal nature of compound (3) in purified kinases described in Example 2 Applicant conducted inhibition experiments using whole cells (see FIG. 12, two left lanes). Anti-phosphotyrosine blots of pyrazolo pyrimidine (2–6) (25 μM) treated NIH3T3 cells expressing v-Src kinase were performed by lysing cells in modified RIPA buffer according to the method of Coussens et al. (1985) Biol. 2753–2763. Cells were also treated for various times before lysis and antiphosphotyrosine detection. Proteins were separated by 12.5% SDS-PAGE and transferred to Protran BA85 (Schleicher-Schuell). The blot was probed with the antiphosphotyrosine monoclonal antibody 4G10 (obtained from Dr. Brian Druker, Oregon Health Sciences Center) and the bound antibody was detected via enhanced chemiluminescence (Pierce) following treatment with HRP-coupled goat anti-mouse antibody (VWR) according to the manufacturer's instructions.

Example 19
Identifying the Substrates

A schematic representation of an experimental approach to identifying v-Src substrates is outlined in FIG. 8 and the data showing experimental validation is in FIG. 12. The assays were performed by making anti-phosphotyrosine blots of pyrazolopyrimidine (2–6) (25 μM) treated NIH3T3 cells expressing either v-Src or v-Src (I338G) kinases were performed by lysing cells in modified RIPA buffer according to the method of Coussens et al. (1985) Biol. 2753–2763. Cells were also treated for various times (in a cell culture $CO_2$ incubator) before lysis and anti-phosphotyrosine detection. Proteins were separated by 12.5% SDS-PAGE and transferred to Protran BA85 (Schleicher-Schuell).

The blot was probed with the anti-phosphotyrosine monoclonal antibody 4G10 and the bound antibody was detected via enhanced chemiluminescence (Pierce) following treatment with HRP-coupled goat-anti-mouse antibody (VWR) according to the manufacturer's instructions. As discussed in Example 7, the two left lanes in FIG. 12B show the same phosphoprotein band pattern indicating that the orthogonal inhibitor (3) does not inhibit wild type v-Src kinase. The series of lanes in the right gel show a prominent band in the bottom of the gel (corresponding to protein molecular weight 3 kDa) which is lost after treatment with 100 μM of compound (3). This specific inhibition of one phosphoprotein is a hallmark of a specific kinase inhibitor. The specificity of the inhibition is confirmed in the last lanes of the gel where the inhibitor is diluted and the phosphorylation of the 36 kDa band reappears when the inhibitor concentration is lower that 5 pM (the measured $IC_{50}$ in vitro is 5 pM, see text). This protein has been tentatively identified based on its unique molecular weight, as a protein called annexin II, an actin binding protein, of unknown function.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

REFERENCES

1. Mustelin, T. 1994. T Cell antigen receptor signaling: Three families of tyrosine kinases and a phosphatase. Immunity. 1: 351–356.
2. Renshaw, M. W., E. T. Kipreos, M. R. Albrecht & J. Y. J. Wang 1992. Oncogenic v-Ab1 tyrosine kinase can inhibit or stimulate growth, depending on the cell context. EMBO J. 11: 3941–3951.
3. Cohen, G. B., R. Ren & D. Baltimore 1995. Modular Binding Domains in Signal Transduction Proteins. Cell. 80: 237–248.
4. Hunter, T. 1987. A Thousand and One Protein Kinases. Cell. 50: 823–829.
5. Eiseman, E. & J. B. Bolen 1992. Engagement of the high-affinity IgE receptor activates src protein-related tyrosine kinases. Nature. 355: 78–80.
6. Murray, A. W. 1994. Cyclin-dependent kinases: regulators of the cell cycle and more. Chem. & Bio. 1: 191–195.
7. White, M. F. 1991. Mini-Review: Structure and Function of Tyrosine Kinase Receptors. J. Bioenergetics Biomem. 23: 63–83.
8. Hunter, T. 1995. Protein Kinases and Phosphatases: The Yin and Yang of Protein Phosphorylation and Signaling. Cell. 80: 225–236.
9. Sawyers, C. L. 1992. The bcr-ab1 gene in chronic myelogenous leudaemia. Cancer Surveys. 15: 37–51.
10. Crabtree, G. R. & N. A. Clipstone 1994. Signal Transmission between the plasma membrane and nucleus of T lymphocytes. Annu. Rev. Biochem. 63: 1045–1083.
11. Kurzrock, R., J. U. Gutternan & M. Talpaz 1988. The molecular genetics of Philadelphia chromosome-positive leukemias. New Engl. J. Med. 319: 990–998.
12. Ullrich, A. & J. Schlessinger 1990. Signal transduction by receptors with tyrosine kinase activity. Cell. 61: 203–212.
13. Bolen, J. B., R. B. Rowley, C. Spana & A. Y. Tsygankov 1992. The Src family of tyrosine protein kinases in hemopoietic signal transduction FASEB J. 6: 3403–3409.
14. Cicchetti, P., B. J. Mayer, G. Thiel & D. Baltimore 1992. Identification of a Protein that binds to the SH3 region of Ab1 and is similar to Bcr and GAP-rho. Science. 257: 803–806.
15. Sawyers, C. L., J. McLaughlin, A. Goga, M. Havlik & O. Witte 1994. The nuclear tyrosine kinase c-Ab1 negatively regulates cell growth Cell. 77: 121–131.
16. Kipreos, E. T. & J. Y. J. Wang 1992. Cell Cycle-regulated binding of c-ab1. Tyrosine kinase to DNA. Science. 256: 382–385.
17. Velazquez, L., M. Fellous, G. R. Stark & S. Pellegrini 1992. Cell. 70: 313–320.
18. Duyster, J., R. Baskaran & J. Y. J. Wang 1995. Src homology 2 domain as a specificity determinant in the c-Ab1-mediated tyrosine phosphorylation of the RNA polymerase II carboxyl-terminal repeated domain Proc. Natl. Acad. Sci. USA. 92: 1555–1559.
19. Mayer, B. J., P. K. Jackson & D. Baltimore 1991. The noncatalytic src homology region 2 segment of abl tyrosine kinase binds to tyrosine-phosphorylated cellular proteins with high affinity. Proc. Natl. Acad. Sci. USA. 88: 627–631.
20. Kamps, M. P., J. E. Buss & B. M. Sefton 1986. Rous Sarcoma Virus Transforming protein lacking myristic acid phosphorylates known polypeptide substrates without inducing transformation. Cell. 45: 105–112.
21. Muller, A. J., A.-M. Pendergast, K. Parmar, M. H. Havlik, N. Rosenberg & O. N. Witte 1993. En Bloc substitution of the Src homology region 2 domain activates the transforming potential of the c-abl protein tyrosine kinase. Proc. Natl. Acad. Sci. USA. 90: 3457–3461.

22. Mayer, B. J. & D. Baltimore 1994. Mutagenic analysis of the roles of SH2 and SH3 domains in regulation of the ab1 tyrosine kinase. Mol. Cell. Biol. 14: 2883–2894.
23. Mayer, B. J., P. K. Jackson, R. A. Van Etten & D. Baltimore 1992. Point Mutations in the ab1 SH2 domain coordinately impair phosphotyrosine binding in vitro and transforming activity in vivo. Mol. Cell. Biol. 12: 609–618.
24. Koyama, S., H. Yu, D. C. Dalgarno, T. B. Shin, L. D. Zydowsky & S. L. Schreiber 1993. Structure of the P13K SH3 domain and analysis of the SH3 Family. Cell. 72: 945–952.
25. Yu, H., M. K. Rosen, T. B. Shin, C. Seidel-Dugan, J. S. Brugge & S. L. Schreiber 1992. Solution Structure of the SH3 domain of Src and identification of its ligand-binding site. Science. 258: 1665–1668.
26. Kohda, D., H. Hatanaka, M. Odaka, V. Mandiyan, A. Ullrich, J. Schlessinger & F. Inagaki 1993. Solution Structure of the SH3 domain of phospholipase-C gamma Cell. 72: 953–960.
27. Waksman, G., S. E. Shoelson, N. Pant, D. Cowburn & J. Kuriyan 1993. Crystal structure/NMR of SH2. Cell. 72: 779–790.
28. Eck, M. J., S. E. Shoelson & S. C. Harrison 1993. SH2 crystal structure. Nature. 362: 87–91.
29. Wang, J. Y. J., C. Queen & D. Baltimore 1982. Expression of an Abelson Murine Leukemia Virus-encoded protein in *Escherichia coli* Causes Extensive Phosphorylation of Tyrosine Residues. J. Biol. Chem. 257: 13181–13184.
30. Schwartzerg, P. L., A. M. Stall, J. D. Hardin, K. S. Bowdish, T. Humaran, S. Boast, M. L. Harbison, E. J. Robertson & S. P. Goff 1991. Mice homozygous for the ab1 mu mutation show poor viability and depletion of selected B and T cell populations. Cell. 65: 1165–1175.
31. Tybulewicz, V. L., C. E. Crawford, P. K. Jackson, R. T. Bronson & R. C. Mulligan 1991. Neonatal lethality and lymphopenia in mice with a homozygous disruption of the c-ab1 proto-oncogene. Cell. 65: 1153–1163.
32. Brugge, J. S. & R. L. Erikson 1977. Nature 269: 346–348.
33. Jove, R. & H. Hanafusa 1987. Ann. Rev. Cell Biol. 3: 31–56.
34. Erpel, T. & S. A. Courtneidge 1995. Curr. Opin. Cell Biology 7: 176–182.
35. Pawson, T. 1995. Nature 373: 573–580.
36. Waksman, G., D. Kominos, S. C. Robertson, N. Pant, D. Baltimore, R. B. Birge, D. Cowbum, H. Hanafusa, B. J. Mayer, M. Overduin, M. D. Resh, C. B. Rios, L. Silverman, & J. Kuriyan 1992. Nature 358: 646–653.
37. Taylor, S. J. & D. Shalloway 1993. Curr. Opin. Genet. Dev. 3: 26–34.
38. Brown, M. T. & J. A. Cooper 1996. Biochemica et Biophysica Acta 1287: 121–149.
39. Songyang, Z., K. L. I. Carraway, M. J. Eck, S. C. Harrison, R. A. Feldman, M. Mohammadi, J. Schlessinger, S. R. Hubbard, D. P. Smith, C. Eng, M. J. Lorenzo, B. A. J. Ponder, B. J. Mayer & L. C. Cantley 1995. Nature 373: 536–539.
40. M. P. Kamps & B. M. Sefton 1988. Oncogene Res. 3: 105–115.
41. Weijland, A. & A. Parmeggiani 1993. Science 259: 1311–1314.
42. Belshaw, P. J., J. G. Schoepfer, K.-Q. Liu, K. L. Morrison & S. L. Schreiber 1995. Angew. Chem. Int. Ed. Engl. 34: 2129–2132.
43. Fujii, T., C. C. Wu, T. Itaya, S. Moro & T. Saito 1973. Chem. Pharm. Bull. 21: 1676–1682.
44. Robins, M. J. & E. M. Trip 1973. Biochemistry 12: 2179–2187.
45. McLaughlin, L. W., N. Piel & T. Hellmann 1985. Synthesis, 00: 322–323.
46. Kikugawa, K., K. Iizuka & M. Ichino 1973. J. Med. Chem. 16: 358–364.
47. Ludwig, J. 1981. Acta Biochim. et Biophys. Acad. Sci Hung. 16: 131–133.
48. Hecht, S. M. & J. W. Kozarich 1973. Biochim. Biophy. Acta 331: 307–309.
49. Reikofski, J. & B. Y. Tao 1992. Biotech. Adv. 10: 535–554.
50. Xu, B., G. V. Bird & T. W. Miller 1995. J. Biol. Chem. 270: 29825–29830.
51. Fukazawa, H., P. Li, S. Mizuno & Y. Uehara 1993. Analytical Biochemistry, 212: 106–110.
52. Lee, T. R., J. Niu & D. S. Lawrence 1995. J. Biol. Chem. 270: 5375–5380.
53. Kwiatkowski, A. P. & M. M. King 1987. Biochemistry 26: 7636–7640.
54. Hubbard, S. R., L. Wei, L. Ellis & W. A. Hendrickson 1994. Nature 372: 746–754.
55. Mohammadi, M., J. Schlessinger & S. R. Hubbard 1996. Cell 86: 577–587.
56. Zheng, J., D. R. Knighton, L. F. Ten Eyck, R. Karlsson, N.-H. Zuong, S. S. Taylor & J. M. Sowadski 1993. Biochemistry 32: 2154–2161.
57. Jeffrey, P. D., A. A. Russo, K. Polyak, E. Gibbs, J. Hurwitz, J. Massague & N. P. Pavletich 1995. Nature 376: 313–320.
58. Kamps, M. P., S. S. Taylor & B. M. Sefton 1984. Nature 310: 589–592.
59. Zoller, M. J., N. C. Nelson & S. S. Taylor 1981. J. Biol. Chem. 256: 10837–10842.
60. Taylor, S. S. & E. Radzio-Andzelm. 1995. Structure 2: 345–355.
61. DeClue, J. E. & G. S. Martin 1989. J. Virol. 63: 542–554.
62. Seidel-Dugan, C., B. E. Meyer, S. M. Thomas & J. S. Brugge 1992. Mol. Cell Biol. 12: 1835–1845.
63. Czernilofsky, A. D., A. D. Levison, H. E. Varmus, J. M. Bishop, E. Tischer & H. M. Goodman 1980. Nature 287: 198–200.
64. Fersht, A., Enzyme Structure and Mechanism. Second ed. 1985, New York: W. H. Freeman.
65. Hunter, T. & B. M. Sefton 1980. Proc. Natl. Acad. Sci. USA 77: 1311–1315.
66. Ozawa, K., Z. Szallasi, M. G. Kazanietz, P. M. Blumberg, H. Mischak, J. F. Mushinski & M. A. Beaven 1993. J. Biol. Chem. 268: 1749–1756.
67. Schultz, C., M. Vajanaphanich, H.-G. Genieser, B. Jastorff, K. E. Barret & R. Y. Tsien 1994. Mol. Pharmacol. 46: 702–708.
68. Merritt, E. A. & M. E. P. Murphy. 1994. Acta Cryst. 50: 869–873.
69. Bacon, D. J. & W. F. Anderson 1988. J. Mol. Graphics 6: 219–220.

70. Schluckebeir, G., M. O'Gara, W. Saenger & X. Chen 1995. Universal Catalytic Domain Structure of AdoMet-dependent Methyltransferases. Mol. Biol. 247: 16–20.
71. Hardie, G., & S. Hanks 1995. Protein Kinase Facts Book. Academic Press
72. Lehninger, P.A., D. Nelson & M. Cox 1993. Principles of Biochemistry. Worth Publishers.
73. Faltynek, C. R., et al. 1995. Biochemistry 34: 12404–12410.
74. Hanke, J., et al. 1996. J. Biol. Chem. 271: 695–701.
75. Druker, B. J., et al. 1996. Nat. Med. 5: 561–566.
76. Hanefeld, U., C. W. Rees, A. J. P. White & D. J. Williams 1996. One-pot synthesis of tetrasubstituted pyrazoles—proof of regiochemistry. J. Chem. Soc. Perkin Trans. 1: 1545–1552.
77. Reikofski J. & B. Y. Tao 1992. Polymerase chain reaction (PCR) techniques for site-directed mutagenesis. Biotech. Adv. 10: 535–554.
78. Xu, B., G. V. Bird & T. W. Miller 1995. Substrate specificities of the insulin and insulin-like growth factor 1 receptor tyrosine kinase catalytic domains. J. Biol. Chem. 270: 29825–29830.
79. Shah, K., Y. Liu, C. Deirnengian & K. M. Shokat 1997. Engineering unnatural nucleotide specificity for Rous Sarcoma virus tyrosine kinase to uniquely label its direct substrates. Proc. Natl. Acad. Sci. USA, 94: 3565–3570.
80. Morgenstern, J. P. & H. Land 1990. Advanced mammalian gene transfer: high titre retroviral vectors with multiple drug selection markers and a complementary helper-free packaging cell line. Nucleic Acids Res. 18: 3587–3596.
81. Pear W. S., G. P. Nolan, M. L. Scott & D. Baltimore 1993. Production of high-titer helper-free retroviruses by transient transfection Proc. Natl. Acad. Sci. USA 90: 8392–8396.
82. Danos, O. & R. C. Mulligan 1988. Safe and efficient generation of recombinant retroviruses with amphotropic and ecotropic host ranges. Proc. Natl. Acad. Sci. USA 85: 6460–6464.
83. Lee, T. R., J. Niu & D. S. Lawrence 1995. The extraordinary active site substrate specificity of pp60c-src. A multiple specificity protein kinase. J. Biol. Chem. 270: 5375–5380.
84. Coussens, P. M., J. A. Cooper, T. Hunter & D. Shalloway 1985. Restriction of the in vitro and in vivo tyrosine kinase activities of pp60c-Src relative to pp60v-Src. Mol. Cell. Biol. 5: 2753–2763.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A method of identifying protein substrates for a mutant protein kinase comprising incubating permeabilized cells expressing the mutant protein kinase with a radiolabeled analog for an appropriate amount of time, lysing the cells, separating the lysate by SDS-PAGE, and identifying the protein substrates, wherein said analog is a gamma-$P^{32}$ radiolabeled $N^6$-substituted ATP analog that is a substrate for a mutant form of a wild-type protein kinase, wherein the analog does not serve as a substrate for the wild-type protein kinase; and, wherein said mutant protein kinase is selected from the group consisting of:
   a mutant protein kinase which comprises an alanine or a glycine as the amino acid which corresponds to position 21 of SEQ ID NO: 3, which is position 338 of v-Src; and,
   a mutant protein kinase which comprises an alanine or a glycine as the amino acid which corresponds to position 21 of SEQ ID NO: 3, which is position 338 of v-Src and which further comprises an alanine or glycine as the amino acid which corresponds to position 6 of SEQ ID NO. 3 which is position 323 of v-Src.

2. The method of claim 1, wherein the analog comprises at least three carbons at the $N^6$ position.

3. The method of claim 1, wherein the analog is selected from the group consisting of $N^6$-(benzyl)ATP and $N^6$-(cyclopentyl)ATP.

4. The method of claim 1, wherein the protein substrates are identified by autoradiography.

5. A method of identifying protein substrates for a mutant protein kinase comprising incubating cell extracts with a radiolabeled analog for an appropriate amount of time, separating the lysate by SDS-PAGE, and identifying the protein substrates, wherein said analog is a gamma-$P^{32}$ radiolabeled $N^6$-substituted ATP analog that is a substrate for a mutant form of a wild-type protein kinase, wherein the analog does not serve as a substrate for the wild-type protein kinase; and, wherein said mutant protein kinase is selected from the group consisting of:
   a mutant protein kinase which comprises an alanine or a glycine as the amino acid which corresponds to position 21 of SEQ ID NO: 3, which is position 338 of v-Src; and,
   a mutant protein kinase which comprises an alanine or a glycine as the amino acid which corresponds to position 21 of SEQ ID NO: 3, which is position 338 of v-Src and which further comprises an alanine or glycine as the amino acid which corresponds to position 6 of SEQ ID NO. 3 which is position 323 of v-Src.

6. The method of claim 5, wherein the analog comprises at least three carbons at the $N^6$ position.

7. The method of claim 5, wherein the analog is selected from the group consisting of $N^6$-(benzyl)ATP and $N^6$-(cyclopentyl)ATP.

8. The method of claim 5, wherein the protein substrates are identified by autoradiography.

* * * * *